(12) United States Patent
Kvitek et al.

(10) Patent No.: US 10,395,760 B2
(45) Date of Patent: Aug. 27, 2019

(54) METHODS, SYSTEMS AND PROCESSES OF IDENTIFYING GENETIC VARIATION IN HIGHLY SIMILAR GENES

(71) Applicant: INVITAE CORPORATION, San Francisco, CA (US)

(72) Inventors: Daniel J. Kvitek, San Francisco, CA (US); Erik Gafni, San Francisco, CA (US)

(73) Assignee: INVITAE CORPORATION, San Francisco, CA (US)

( * ) Notice: Subject to any disclaimer, the term of this patent is extended or adjusted under 35 U.S.C. 154(b) by 399 days.

(21) Appl. No.: 15/098,272

(22) Filed: Apr. 13, 2016

(65) Prior Publication Data

US 2016/0300014 A1    Oct. 13, 2016

Related U.S. Application Data

(60) Provisional application No. 62/146,936, filed on Apr. 13, 2015.

(51) Int. Cl.
| | |
|---|---|
| *G01N 33/48* | (2006.01) |
| *G01N 33/50* | (2006.01) |
| *G16B 30/00* | (2019.01) |
| *G16B 20/00* | (2019.01) |

(52) U.S. Cl.
CPC ............ *G16B 30/00* (2019.02); *G16B 20/00* (2019.02)

(58) Field of Classification Search
None
See application file for complete search history.

(56) References Cited

U.S. PATENT DOCUMENTS

| | | |
|---|---|---|
| 2008/0124712 A1 | 5/2008 | Hantash et al. |
| 2009/0087846 A1 | 4/2009 | Radtkey et al. |
| 2013/0332081 A1 | 12/2013 | Reese et al. |
| 2014/0011861 A1 | 1/2014 | McClelland et al. |
| 2014/0093913 A1 | 4/2014 | Cost et al. |
| 2014/0274738 A1 | 9/2014 | Amorese et al. |
| 2015/0094212 A1 | 4/2015 | Gottimukkala et al. |

OTHER PUBLICATIONS

Liu et al. Comparison of Next-Generation Sequencing systems. Journal of Biomedicine and Biotechnology, article ID 251364, 11 pages. (Year: 2012).*
Clendenning, Mark et al., "Long-range PCR Facilitates the Identification of PMS2-Specific Mutations", Human Mutation, May 2006, vol. 27, pp. 490-495.
Gargis, Amy S. et al., "Assuring the Quality of Next-generation Sequencing in Clinical Laboratory Practice", Nature Biotechnology, Nov. 2012, vol. 30, pp. 1033-10366.
Gill, Sharlene et al., "Isolated Loss of PMS2 Expression in Colorectal Cancers: Frequency, Patient Age, and Familial Aggregation", Clinical Cancer Research, Sep. 15, 2005, vol. 11, pp. 6466-6471.
(Continued)

*Primary Examiner* — Russell S Negin
(74) *Attorney, Agent, or Firm* — Pillsbury Winthrop Shaw Pittman, LLP

(57) ABSTRACT

Provided herein are novel methods, systems and processes for mapping sequence reads to a modified reference genome and determining the presence or absence of a genetic variation, or the likelihood thereof, in a gene of interest in a subject.

35 Claims, 6 Drawing Sheets

(56) References Cited

OTHER PUBLICATIONS

Hayward, Bruce E. et al., "Extensive Gene Conversion at the PMS2 DNA Mismatch Repair Locus", Human Mutation, May 2007, vol. 28, pp. 424-430.

Lynch, H. T. et al., "Review of the Lynch Syndrome: History, Molecular Genetics, Screening, Differential Diagnosis, and Medicolegal Ramifications", Clinical Genetics, Jul. 2009, vol. 76, pp. 1-18.

Truninger, Kaspar et al., "Immunohistochemical Analysis Reveals High Frequency of PMS2 Defects in Colorectal Cancer", Gastroenterology, May 2005, vol. 128, pp. 1160-1171.

Vaughn, Cecily P. et al, "The Frequency of Previously Undetectable Deletions Involving 3' Exons of the PMS2 Gene", Genes, Chromosomes and Cancer, Dec. 2012, vol. 52, pp. 107-112.

Donner, Kati et al., "Complete Genomic Structure of the Human Nebulin Gene and Identification of Alternatively Spliced Transcripts", European Journal of Human Genetics, published online Jul. 21, 2004. vol. 12, pp. 744-751.

Rehm, Heidi L. et al., "ACMG Clinical Laboratory Standards for Next-generation Sequencing", Genetics in Medicine, Sep. 2013, vol. 15, pp. 733-747.

International Preliminary Report on Patentability dated Oct. 26, 2017 for PCT/US2016/027379.

International Search Report and Written Opinion dated Jul. 15, 2016 in International Patent Application No. PCT/US2016/027379 (14 Pages).

Carvalho, Claudia M. B. et al. "Structural Variation and Missense Mutation in SBDS Associated with Shwachman-Diamond Syndrome," BMC Medical Genetics, Jun. 14, 2014, vol. 15, pp. 1-10.

Harismendy, Olivier et al. "Method for Improving Sequence Coverage Uniformity of Targeted Genomic Intervals Amplified by LR-PCR Using Illumina GA Sequencing-by-Synthesis Technology," Biotechniques, Mar. 1, 2009, vol. 46, pp. 229-231.

\* cited by examiner

METHODS, SYSTEMS AND PROCESSES OF IDENTIFYING GENETIC VARIATION IN HIGHLY SIMILAR GENES

RELATED PATENT APPLICATIONS

This patent application claims the benefit of U.S. Provisional Patent Application No. 62/146,936 filed on Apr. 13, 2015, entitled METHODS, SYSTEMS AND PROCESSES OF IDENTIFYING GENETIC VARIATION IN HIGHLY SIMILAR GENES, naming Dan Kvitek and Erik Gafni as inventors. The entire content of the foregoing application is incorporated herein by reference, including all text, tables and drawings.

FIELD

The technology relates in part to methods and processes of nucleic acid manipulation, analysis and high-throughput sequencing.

BACKGROUND

Genetic information of living organisms (e.g., animals, plants, microorganisms, viruses) is encoded in deoxyribonucleic acid (DNA) or ribonucleic acid (RNA). Genetic information is a succession of nucleotides or modified nucleotides representing the primary structure of nucleic acids. The nucleic acid content (e.g., DNA) of an organism is often referred to as a genome. In most humans, the complete genome typically contains about 30,000 genes located on twenty-three pairs of chromosomes. Most genes encode a specific protein, which after expression via transcription and translation fulfills one or more biochemical functions within a living cell.

Many medical conditions are caused by, or its risk of occurrence is influenced by, one or more genetic variations within a genome. Some genetic variations may predispose an individual to, or cause, any of a number of diseases such as, for example, diabetes, arteriosclerosis, obesity, various autoimmune diseases and cancer (e.g., colorectal, breast, ovarian, lung). Such genetic variations can take the form of an addition, substitution, insertion or deletion of one or more nucleotides within a genome.

Genetic variations can be identified by analysis of nucleic acids. Nucleic acids of a genome can be analyzed by various methods including, for example, methods that involve massively parallel sequencing. Massively parallel sequencing (MPS) techniques often generate thousands, millions or even billions of small sequencing reads. To determine genomic sequences, each read is often mapped to a reference genome and collections of reads are assembled into a sequence representation of an individual's genome, or portions thereof. The process of mapping and assembly of reads is carried out by one or more computers (e.g., microprocessors and memory) and is driven by a set of instructions (e.g., software instructions, code and/or algorithms). Such mapping and assembly processes often fail when a genetic variation is encountered in a genome of a subject. For example, existing software and programs sometimes incorrectly map reads, fail to map reads and/or fail to correctly assemble regions of a gene of interest where another highly similar gene exists in the same genome, thereby diminishing the ability to successfully identify genetic variations in such a gene of interest. This is especially problematic where it is desired to quickly and accurately detect the presence or absence of known variants in highly similar genes using data generated by high throughput MPS methods that can rapidly generate thousands, millions or even billions of small sequencing reads from multiple subjects.

Methods, systems and processes herein offer significant advances and improvements to current nucleic acid analysis techniques. Such advances and improvements can help expedite screening of MPS-generated data for genetic variations that may exist in one or more genes of a set of two or more highly similar genes.

SUMMARY

A genome often comprises two or more genes that are highly similar. For example a genome of a subject often comprises a gene of interest and one or more counterpart genes that comprise regions of nucleic acid sequence that are identical or nearly identical to nucleic acid sequences in the gene of interest. A counterpart gene, or a portion thereof, is often highly similar in sequence to a gene of interest, or portion thereof. In some embodiments the counterpart gene is highly similar or nearly identical to the gene of interest in the exons where the variation(s) of interest are located even if it is not highly homologous to other regions of the gene of interest. In some embodiments, such highly similar genes refer to a gene of interest and a pseudogene (where the pseudogene is the counterpart), or in certain embodiments such highly similar genes refer to a gene of interest and one or more gene family members of the gene of interest (where the other gene family member or members are counterparts). In certain embodiments a counterpart gene is a pseudogene or a gene family member of a gene of interest. In some embodiments a gene of interest is any gene in a genome that is suspected of having a genetic variation where the genome also comprises another gene that is highly similar to the gene of interest (e.g., a counterpart gene).

In certain embodiments, a reference genome is modified by substantially altering one or more counterpart genes such that reads derived from a counterpart gene of a subject cannot map to the substantially altered counterpart gene of the modified reference genome. In some embodiments, a reference genome is modified by substantially altering one or more counterpart genes of a gene of interest such that reads derived from a counterpart gene of a subject are forced to map to the gene of interest in the modified reference genome instead of mapping to the counterpart gene.

In some aspects provided herein is a computer-implemented method for determining a likelihood of a presence or absence of a genetic variation in a gene of interest for a subject where the subject's genome also contains one or more counterpart genes to the gene of interest such that the counterpart genes have a high degree of homology to the gene of interest, comprising the steps of (a) providing a modified reference genome comprising a gene of interest where one or more counterpart genes to the gene of interest are substantially altered such that sequence reads for such counterpart gene or genes map to the gene of interest instead of the counterpart genes; (b) mapping sequence reads to the modified reference genome, wherein 1) the sequence reads are obtained from a sample obtained from a diploid subject using a massively parallel sequencing method, and 2) the sequence reads obtained from the gene of interest and the at least one counterpart gene of the subject map to the gene of interest of the modified reference genome and not to the counterpart gene, thereby providing sequence reads mapped to the gene of interest of the modified reference genome; and (c) determining the likelihood of a presence or absence of a genetic variation in the gene of interest of the subject according to the sequence reads mapped to the gene of interest of the modified reference genome, wherein the absence of a variation indicates the absence of a variation in either the gene of interest or the counterpart and the presence of a variation indicates that the variation is present in the gene of interest or the counterpart gene or both. In some aspects, the counterpart gene of the modified reference genome is substantially altered by deleting the counterpart gene or changing the nucleotides of the counterpart gene to a non-natural sequence or otherwise preventing sequencing reads from the counterpart gene from being mapped to the counterpart gene. In some aspects the mapping comprises an expectation that at least 4 alleles of the gene of interest of the subject map to the gene of interest of the modified reference genome. In certain aspects a ploidy of at least 4 is expected for the gene of interest of the subject. In some aspects the counterpart gene of the subject is at least 80% identical to the gene of interest of the subject In some aspects provided herein is a computer-implemented method for determining a presence or absence of a genetic variation in a subject, or a likelihood thereof, comprising (a) mapping sequence reads to a modified reference genome comprising a gene of interest and at least one counterpart gene of the gene of interest, wherein 1) the at least one counterpart gene of the modified reference genome is substantially altered, 2) the sequence reads are obtained from a sample obtained from a diploid subject using a massively parallel sequencing method, and 3) the sequence reads obtained from the gene of interest and the at least one counterpart gene of the subject map to the gene of interest of the modified reference genome, and (b) determining the likelihood of a presence or absence of a genetic variation in the gene of interest of the subject according to the sequence reads mapped to the gene of interest of the reference genome. In some aspects the mapping comprises an expectation that at least 4 alleles of the gene of interest of the subject map to the gene of interest of the modified reference genome. In certain aspects a ploidy of at least 4 is expected for the gene of interest of the subject. In some aspects the counterpart gene of the subject is at least 80% identical to the gene of interest of the subject.

In some aspects provided herein is a non-transitory computer-readable storage medium with an executable program stored thereon, which program is configured to instruct a microprocessor to (a) map sequence reads to a modified reference genome comprising a gene of interest and at least one counterpart gene of the gene of interest, wherein 1) the at least one counterpart gene of the modified reference genome is substantially altered, 2) the sequence reads are obtained from a sample obtained from a diploid subject using a massively parallel sequencing method, and 3) the sequence reads obtained from the gene of interest and the at least one counterpart gene of the subject are mapped to the gene of interest of the modified reference genome, thereby providing sequence reads mapped to the gene of interest of the modified reference genome; and (b) determine the presence or absence, or likelihood of thereof, of a genetic variation in the gene of interest of the subject according to the sequence reads mapped to the gene of interest of the modified reference genome.

In some aspects provided herein is a system for determining the presence or absence, or the likelihood thereof, of a genetic variation in a subject, the system comprising one or more processors configured to execute computer program modules, the computer program modules comprising (a) a mapping module configured to map sequence reads to a modified reference genome comprising a gene of interest and at least one counterpart gene of the gene of interest, wherein 1) the at least one counterpart gene of the modified reference genome is substantially altered, 2) the sequence reads are obtained from a sample obtained from a diploid subject using a massively parallel sequencing method, and 3) the sequence reads obtained from the gene of interest and the at least one counterpart gene of the subject are mapped to the gene of interest of the modified reference genome, thereby providing sequence reads mapped to the gene of interest of the modified reference genome, and (b) an outcome module configured to determine the likelihood of a presence or absence of a genetic variation in the gene of interest of the subject according to the sequence reads mapped to the gene of interest of the modified reference genome.

In some aspects samples are obtained from one or more human subjects.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

DETAILED DESCRIPTION

Figure 1:
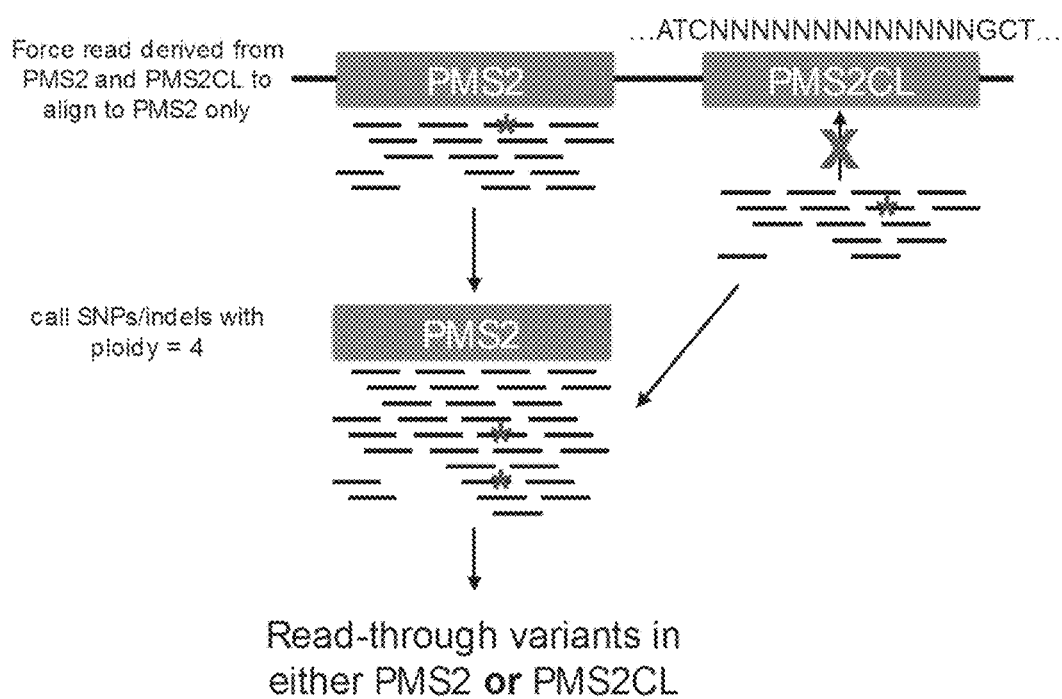
FIG. 1 shows an embodiment of a bioinformatics screening strategy where the PMS2CL gene of the reference genome (where the PMS2CL gene is a counterpart gene to the PMS2 gene, the gene of interest) is substantially altered by substituting all nucleotides of the counterpart gene with Ns in lieu of the As, Ts, Gs and Cs of the natural sequence of the counterpart gene.

Next generation sequencing (NGS) allows for sequencing nucleic acids on a genome-wide scale by methods that are faster and cheaper than traditional methods of sequencing. Methods, systems and processes herein provide for improvements of analytical methods used to evaluate large amounts of sequence data derived from NGS methods. Such methods can be used to determine the presence or absence of a genetic variation, or likelihood thereof, and/or the presence or absence of associated diseases and disorders. In some embodiments, provided herein are methods that comprise, in part, manipulation and analysis of sequence reads that are often obtained by MPS methods such as NGS.

Traditional mappers and aligners often fail to correctly map reads derived from a gene of interest where another highly similar gene, such as a pseudogene, exists in the same genome. Such genes of interest sometimes contain a genetic variation (e.g., polymorphisms, single nucleotide polymorphisms (SNP), short tandem repeats (STRs), deletions, insertions, etc.). Calling a genetic variation that is present in a gene of interest, where a second highly similar gene (e.g., a pseudogene) exists in the same genome, is a difficult problem for most aligners and mappers and therefore existing algorithms and software packages often fail to correctly and unambiguously map and align reads to such highly similar genes. There is a great need for new and improved systems and methods (e.g., microprocessor dependent methods) that can correctly and routinely identify genetic variations in genes that comprise highly similar counterparts in a genome. Provided herein are novel methods, systems and processes for mapping sequence reads to a modified reference genome and determining the presence or absence of a genetic variation, or the likelihood thereof, in a gene of interest in a genome of a subject, which genome contains one or more genes that are highly similar to a gene of interest.

NGS methods often produce large databases of genomic sequence data comprising sequence reads from multiple subjects. Traditional gold standard techniques such as LR-PCR/Sanger are often comparatively too slow, too laborious and too expensive to screen hundreds or thousands of subjects for a genetic variation such as a rare known polymorphism. Provided herein, in some embodiments, are methods and systems to rapidly screen patient genomic data in an effort to quickly screen for the absence of a genetic variation in a gene of interest where there is a counterpart gene for the gene of interest which may confound the ability to interpret NGS sequencing reads using conventional mappers and aligners and an unmodified reference genome. For example, where a known polymorphism that is associated with a disease is present in a small percentage of the population (e.g., <15%, <10%, or <5% of the population), methods and systems presented herein can rapidly screen large NGS databases or data sets derived from tens, hundreds, or thousands of subjects and quickly identify individuals that do not have such a polymorphism in a gene of interest (e.g., where a counterpart gene of the gene of interest exists in a genome). Such methods and systems can also quickly identify the relatively small portion of subjects in the data set with a likelihood of having the rare disease associated polymorphism. Gold standard techniques (e.g., such as long-range PCR (LR-PCR) followed by Sanger sequencing) can then be used to confirm the presence or absence of the disease associated polymorphism in the gene of interest (as opposed to the counterpart gene) in the small number of subjects determined to have a likelihood of having the disease associated polymorphism.

For example, Lynch syndrome (or hereditary non-polyposis colon cancer) is characterized by familial predisposition to cancers of the colon, endometrium, ovary stomach and urinary tract. Most cases of Lynch syndrome are caused by variants in MLH1, MSH2, and MSH6, however 4-11% of cases are caused by variants in the PMS2 gene. In Lynch Syndrome, testing for inherited variants in the PMS2 gene is hampered by the presence of a pseudogene, PMS2CL, which has nearly identical homology to PMS2 in the last four exons of the gene (exons 12-15). Thus, sequence reads obtained using NGS methods cannot be unambiguously aligned to PMS2 or PMS2CL. Gene conversion between exons 12-15 of PMS2 & PMS2CL further complicates this issue. Methods or systems described herein, in certain embodiments, utilize a first screen where NGS-derived sequence reads derived from both PMS2 and the paralogous PMS2CL gene are forced to map to PMS2 of a modified reference genome comprising a substantially altered PMS2CL gene. Subjects having only reads that lack the disease-causing variants in PMS2 can be quickly identified. Subjects having reads that contain a known PMS2 variant for Lynch syndrome are often determined to have a likelihood of having Lynch syndrome (a likelihood of having a PMS2 variant associated with Lynch syndrome) since the location of such variants cannot be unambiguous localized to the PMS2 or PMS2CL gene. Since variants in the PMS2 gene that cause Lynch syndrome are rare, the remaining number of subjects identified to have a likelihood of having Lynch syndrome is often relatively small. Therefore, nucleic acid obtained from the remaining subjects can be further analyzed by a suitable sequencing method, thereby reducing costs and turn around time. For example, in some embodiments, Sanger sequencing of LR-PCR amplicon products of PMS2 and/or PMS2CL is used to confirm the presence or absence of non-benign variants associated with Lynch syndrome. This approach was validated with samples known to have specific variants in these exons for both genes (see Example 1).

Subjects

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

Samples

Provided herein are methods and compositions for analyzing a sample. A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

Nucleic Acids & Genes

The terms "nucleic acid" refers to one or more nucleic acids (e.g., a set or subset of nucleic acids) of any composition from, such as DNA (e.g., complementary DNA (cDNA), genomic DNA (gDNA) and the like), RNA (e.g., message RNA (mRNA), short inhibitory RNA (siRNA), ribosomal RNA (rRNA), tRNA, microRNA, and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. In some embodiments nucleic acid refers to genomic DNA.

Unless specifically limited, the term encompasses nucleic acids comprising deoxyribonucleotides, ribonucleotides and known analogs of natural nucleotides. A nucleic acid may include, as equivalents, derivatives, or variants thereof, suitable analogs of RNA or DNA synthesized from nucleotide analogs, single-stranded ("sense" or "antisense", "plus" strand or "minus" strand, "forward" reading frame or "reverse" reading frame) and double-stranded polynucleotides. Nucleic acids may be single or double stranded. A nucleic acid can be of any length of 2 or more, 3 or more, 4 or more or 5 or more contiguous nucleotides. A nucleic acid can comprise a specific 5' to 3' order of nucleotides known in the art as a sequence (e.g., a nucleic acid sequence, e.g., a sequence).

A nucleic acid may be naturally occurring and/or may be synthesized, copied or altered (e.g., by a technician, scientist or one of skill in the art). For, example, a nucleic acid may be an amplicon. A nucleic acid may be from a nucleic acid library, such as a gDNA, cDNA or RNA library, for example. A nucleic acid can be synthesized (e.g., chemically synthesized) or generated (e.g., by polymerase extension in vitro, e.g., by amplification, e.g., by PCR). A nucleic acid may be, or may be from, a plasmid, phage, virus, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. Nucleic acids (e.g., a library of nucleic acids) may comprise nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples). Nucleic acid provided for processes or methods described herein may comprise nucleic acids from 1 to 1000, 1 to 500, 1 to 200, 1 to 100, 1 to 50, 1 to 20 or 1 to 10 samples. Oligonucleotides are relatively short nucleic acids. Oligonucleotides can be from about 2 to 150, 2 to 100, 2 to 50, or 2 to about 35 nucleic acids in length. In some embodiments oligonucleotides are single stranded. In certain embodiments, oligonucleotides are primers. Primers are often configured to hybridize to a selected complementary nucleic acid and are configured to be extended by a polymerase after hybridizing.

The genetic material of a subject often comprises one or more genes. In certain embodiments a gene comprises or consists of one or more nucleic acids. The term "gene" means the segment of DNA involved in producing a polypeptide chain and can include coding regions (e.g., exons), regions preceding and following the coding region (leader and trailer) involved in the transcription/translation of the gene product and the regulation of the transcription/translation, as well as intervening sequences (introns) between individual coding segments (exons). A gene may not necessarily produce a peptide or may produce a truncated or non-functional protein due to genetic variation in a gene sequence (e.g., mutations in coding and non-coding portions of a gene). For example, a non-functional gene can be a pseudogene. A gene, whether functional or non-functional, can often be identified by homology to a gene in a reference genome. For example, any specific gene (e.g., a gene of interest, a counterpart gene, a pseudogene and the like) of a subject can be identified in another subject, genome or in a reference genome by one of skill in the art. In a diploid subject, a gene often comprises a pair of alleles (e.g., two alleles). Thus a method, system or process herein can be applied to one or both alleles of a gene. In some embodiments a method, system or process herein is applied to each allele of a gene.

In some embodiments a gene is a gene of interest. In certain embodiment a subject comprises a gene of interest. In certain embodiment a genome comprises a gene of interest. In certain embodiment a reference genome and/or a modified reference genome comprises a gene of interest. In some embodiments, a gene of interest is a gene having one or more counterpart genes that exist in the same subject and/or genome. In certain embodiments a gene of interest is a gene having or suspected of having a genetic variation. In certain embodiments a gene of interest comprises a known genetic variation or is suspected of comprising a known genetic variation (e.g., a known polymorphism). In certain embodiments a gene of interest comprises, or is suspected of having, a genetic variation associated with a disease, condition or disorder. In certain embodiments a gene of interest comprises, or is suspected of having a genetic variation associated with a subjects predisposed to a disease, condition or disorder.

In some embodiments a gene is a counterpart gene and/or a pseudogene. A counterpart gene is a nucleic acid that is highly similar to a corresponding gene of interest where both the counterpart gene and gene of interest are in the same genome (e.g., a genome of a subject). A gene of interest can have one or more corresponding counterpart genes. In certain embodiments a gene of interest has 1, 2, 3, 4, 5, or more counterpart genes. In some embodiments a gene of interest has 1 to 20, 1 to 10, or 1 to 5 counterpart genes in the same genome. Highly similar means at least 70% identical, at least 75% identical, at least 80% identical, at least 85% identical, at least 90% identical, or at least 91%, 92%, 93%, 94%, 95%, 96%, 97%, 98%, or at least 99% identical to a gene of interest. In some embodiments a gene of interest and its counterpart gene are highly similar, but are not 100% identical to each other. In some embodiments a gene of interest, or portions thereof, are 100% identical to its counterpart gene, or portions thereof. In certain embodiments a counterpart gene, or portion thereof, is 70% to 99% identical, 80% to 99% identical, 80% to 95% identical, 70% to 95% identical, 80% to 90% identical, or 85% to 99% to a gene of interest, or portion thereof. In some embodiments, a counterpart gene is a gene family member of a gene of interest. In some embodiments, a gene of interest and one or more counterpart genes of the gene of interest are members of the same clustered gene family. In certain embodiments a gene of interest is a member of a gene family that includes one or more counterparts (counterpart genes) of the gene of interest. A counterpart gene may be functional or non-functional (e.g., a pseudogene). In some embodiments a counterpart gene of a gene of interest is a pseudogene of a gene of interest. In some embodiments a counterpart gene of a gene of interest is not a pseudogene of a gene of interest. For example, in certain embodiments a counterpart gene of a gene of interest is a paralog (e.g., a functional paralog). A multitude of genes of interest (e.g., genes having one or more counterpart genes) are known and are readily available and accessible from a suitable source (e.g., a suitable website or database). In a diploid subject, a gene of interest consists of two alleles and each counterpart gene of the gene of interest comprises two alleles. Any gene can be a gene of interest. Non-limiting examples of a gene of interest include human genes A2M, AACS, AARSD1, ABCA10, ABCA12, ABCA3, ABCA8, ABCA9, ABCB1, ABCB10, ABCB4, ABCC11, ABCC12, ABCC6, ABCD1, ABCE1, ABCF1, ABCF2, ABT1, ACAA2, ACCSL, ACER2, ACO2, ACOT1, ACOT4, ACOT7, ACP1, ACR, ACRC, ACSBG2, ACSM1, ACSM2A, ACSM2B, ACSM4, ACSM5, ACTA1, ACTA2, ACTB, ACTG1, ACTG2, ACTN1, ACTN4, ACTR1A, ACTR2, ACTR3, ACTR3C, ACTRT1, ADAD1, ADAL, ADAM18, ADAM20, ADAM21, ADAM32, ADAMTS7, ADAMTSL2, ADAT2, ADCY5, ADCY6, ADCY7, ADGB, ADH1A, ADH1B, ADH1C, ADH5, ADORA2B, ADRBK2, ADSS, AFF3, AFF4, AFG3L2, AGAP1, AGAP10, AGAP11, AGAP4, AGAP5, AGAPE, AGAP7, AGAPE, AGAP9, AGER, AGGF1, AGK, AGPAT1, AGPAT6, AHCTF1, AHCY, AHNAK2, AHRR, AIDA, AIF1, AIM1L, AIMP2, AK2, AK3, AK4, AKAP13, AKAP17A, AKIP1, AKIRIN1, AKIRIN2, AKR1B1, AKR1B10, AKR1B15, AKR1C1, AKR1C2, AKR1C3, AKR1C4, AKR7A2, AKR7A3, AKTIP, ALDH3B1, ALDH3B2, ALDH7A1, ALDOA, ALG1, ALG10, ALG10B, ALG1L, ALG1L2, ALG3, ALKBH8, ALMS1, ALOX15, ALOX15B, ALOXE3, ALPI, ALPP, ALPPL2, ALYREF, AMD1, AMELX, AMELY, AMMECR1L, AMY1A, AMY1B, AMY1C, AMY2A, AMY2B, AMZ2, ANAPC1, ANAPC10, ANAPC15, ANKRD11, ANKRD18A, ANKRD18B, ANKRD20A1, ANKRD20A19P, ANKRD20A2, ANKRD20A3, ANKRD20A4, ANKRD30A, ANKRD30B, ANKRD36, ANKRD36B, ANKRD49, ANKS1B, ANO10, ANP32A, ANP32B, ANXA2, ANXA2R, ANXA8, ANXA8L1, ANXA8L2, AOC2, AOC3, AP1B1, AP1S2, AP2A1, AP2A2, AP2B1, AP2S1, AP3M2, AP3S1, AP4S1, APBA2, APBB1IP, APH1B, API5, APIP, APOBEC3A, APOBEC3B, APOBEC3C, APOBEC3D, APOBEC3F, APOBEC3G, APOC1, APOL1, APOL2, APOL4, APOM, APOOL, AQP10, AQP12A, AQP12B, AQP7, AREG, AREGB, ARF1, ARF4, ARF6, ARGFX, ARHGAP11A, ARHGAP11B, ARHGAP20, ARHGAP21, ARHGAP23, ARHGAP27, ARHGAP42, ARHGAP5, ARHGAP8, ARHGEF35, ARHGEF5, ARID2, ARID3B, ARIH2, ARL14EP, ARL16, ARL17A, ARL17B, ARL2BP, ARL4A, ARL5A, ARL6IP1, ARL6IP6, ARL8B, ARMC1, ARMC10, ARMC4, ARMC8, ARMCX6, ARPC1A, ARPC2, ARPC3, ARPP19, ARSD, ARSE, ARSF, ART3, ASAH2, ASAH2B, ASB9, ASL, ASMT, ASMTL, ASNS, ASS1, ATAD1, ATAD3A, ATAD3B, ATAD3C, ATAT1, ATF4, ATF6B, ATF7IP2, ATG4A, ATM, ATMIN, ATP13A4, ATP13A5, ATP1A2, ATP1A4, ATP1B1, ATP1B3, ATP2B2, ATP2B3, ATP5A1, ATP5C1, ATP5F1, ATP5G1, ATP5G2, ATP5G3, ATP5H, ATP5J, ATP5J2, ATP5J2-PTCD1, ATP5O, ATP6AP2, ATP6V0C, ATP6V1E1, ATP6V1F, ATP6V1G1, ATP6V1G2, ATP7B, ATP8A2, ATP9B, ATXN1L, ATXN2L, ATXN7L3, AURKA, AURKAIP1, AVP, AZGP1, AZI2, B3GALNT1, B3GALT4, B3GAT3, B3GNT2, BAG4, BAG6, BAGE2, BAK1, BANF1, BANP, BCAP31, BCAR1, BCAS2, BCL2A1, BCL2L12, BCL2L2-PABPN1, BCLAF1, BCOR, BCR, BDH2, BDP1, BEND3, BET1, BEX1, BHLHB9, BHLHE22, BHLHE23, BHMT, BHMT2, BIN2, BIRC2, BIRC3, BLOC1S6, BLZF1, BMP2K, BMP8A, BMP8B, BMPR1A, BMS1, BNIP3, BOD1, BOD1L2, BOLA2, BOLA2B, BOLA3, BOP1, BPTF, BPY2, BPY2B, BPY2C, BRAF, BRCA1, BRCC3, BRD2, BRD7, BRDT, BRI3, BRK1, BRPF1, BRPF3, BRWD1, BTBD10, BTBD6, BTBD7, BTF3, BTF3L4, BTG1, BTN2A1, BTN2A2, BTN3A1, BTN3A2, BTN3A3, BTNL2, BTNL3, BTNL8, BUB3, BZW1, C10orf129, C10orf88, C11orf48, C11orf58, C11or174, C11or175, C12orf29, C12orf42, C12orf49, C12orf71, C12or176, C14orf119, C14orf166, C14orf178, C15orf39, C15orf40, C15orf43, C16orf52, C16orf88, C17orf51, C17orf58, C17orf61, C17orf89, C17orf98, C18orf21, C18orf25, C1D, C1GALT1, C1QBP, C1QL1, C1QL4, C1QTNF9, C1QTNF9B, C1QTNF9B-AS1, C1orf100, C1orf106, C1orf114, C2, C22orf42, C22orf43, C2CD4A, C2orf16, C2orf27A, C2orf27B, C2orf69, C2orf78, C2orf81, C4A, C4B, C4BPA, C4orf27, C4orf34, C4orf46, C5orf15, C5orf43, C5orf52, C5orf60, C5orf63, C6orf10, C6orf106, C6orf136, C6orf15, C6orf203, C6orf25, C6orf47, C6orf48, C7orf63, C7orf73, C8orf46, C9orf123, C9orf129, C9orf172, C9orf57, C9orf69, C9orf78, CA14, CA15P3, CA5A, CA5B, CABYR, CACNA1C, CACNA1G, CACNA1H, CACNA1I, CACYBP, CALCA, CALCB, CALM1, CALM2, CAMSAP1, CAP1, CAPN8, CAPZA1, CAPZA2, CARD16, CARD17, CASC4, CASP1, CASP3, CASP4, CASP5, CATSPER2, CBR1, CBR3, CBWD1, CBWD2, CBWD3, CBWD5, CBWD6, CBWD7, CBX1, CBX3, CCDC101, CCDC111, CCDC121, CCDC127, CCDC14, CCDC144A, CCDC144NL, CCDC146, CCDC150, CCDC174, CCDC25, CCDC58, CCDC7, CCDC74A, CCDC74B, CCDC75, CCDC86, CCHCR1, CCL15, CCL23, CCL3, CCL3L1, CCL3L3, CCL4, CCL4L1, CCL4L2, CCNB1IP1, CCNB2, CCND2, CCNG1, CCNJ, CCNT2, CCNYL1, CCR2, CCR5, CCRL1, CCRN4L, CCT4, CCT5, CCT6A, CCT7, CCT8, CCT8L2, CCZ1, CCZ1B, CD177, CD1A, CD1B, CD1C, CD1D, CD1E, CD200R1, CD200R1L, CD209, CD276, CD2BP2, CD300A, CD300C, CD300LD, CD300LF, CD33, CD46, CD83, CD8B, CD97, CD99, CDC14B, CDC20, CDC26, CDC27, CDC37, CDC42, CDC42EP3, CDCA4, CDCA7L, CDH12, CDK11A, CDK11B, CDK2AP2, CDK5RAP3, CDK7, CDK8, CDKN2A, CDKN2AIPNL, CDKN2B, CDON, CDPF1, CDRT1, CDRT15, CDRT15L2, CDSN, CDV3, CDY1, CDY2A, CDY2B, CEACAM1, CEACAM18, CEACAM21, CEACAM3, CEACAM4, CEACAM5, CEACAM6, CEACAM7, CEACAM8, CEL, CELA2A, CELA2B, CELA3A, CELA3B, CELSR1, CEND1, CENPC1, CENPI, CENPJ, CENPO, CEP170, CEP19, CEP192, CEP290, CEP57L1, CES1, CES2, CES5A, CFB, CFC1, CFC1B, CFH, CFHR1, CFHR2, CFHR3, CFHR4, CFHR5, CFL1, CFTR, CGB, CGB1, CGB2, CGB5, CGB7, CGB8, CHAF1B, CHCHD10, CHCHD2, CHCHD3, CHCHD4, CHD2, CHEK2, CHIA, CHMP4B, CHMP5, CHORDC1, CHP1, CHRAC1, CHRFAM7A, CHRNA2, CHRNA4, CHRNB2, CHRNB4, CHRNE, CHST5, CHST6, CHSY1, CHTF8, CIAPIN1, CIC, CIDEC, CIR1, CISD1, CISD2, CKAP2, CKMT1A, CKMT1B, CKS2, CLC, CLCN3, CLCNKA, CLCNKB, CLDN22, CLDN24, CLDN3, CLDN4, CLDN6, CLDN7, CLEC17A, CLEC18A, CLEC18B, CLEC18C, CLEC1A, CLEC1B, CLEC4G, CLEC4M, CLIC1, CLIC4, CLK2, CLK3, CLK4, CLNS1A, CMPK1, CMYA5, CNEP1R1, CNN2, CNN3, CNNM3, CNNM4, CNOT6L, CNOT7, CNTNAP3, CNTNAP3B, CNTNAP4, COA5, COBL, COIL, COL11A2, COL12A1, COL19A1, COL25A1, COL28A1, COL4A5, COL6A5, COL6A6, COMMD4, COMMD5, COPRS, COPS5, COPSE, COQ10B, CORO1A, COX10, COX17, COX20, COX5A, COX6A1, COX6B1, COX7B, COX7C, COX8C, CP, CPAMD8, CPD, CPEB1, CPSF6, CR1, CR1L, CRADD, CRB3, CRCP, CREBBP, CRHR1, CRLF2, CRLF3, CRNN, CROCC, CRTC1, CRYBB2, CRYGB, CRYGC, CRYGD, CS, CSAG1, CSAG2, CSAG3, CSDA, CSDE1, CSF2RA, CSF2RB, CSGALNACT2, CSH1, CSH2, CSHL1, CSNK1A1, CSNK1D, CSNK1E, CSNK1G2, CSNK2A1, CSNK2B, CSPG4, CSRP2, CST1, CST2, CST3, CST4, CST5, CST9, CT45A1, CT45A2, CT45A3, CT45A4, CT45A5, CT45A6, CT47A1, CT47A10, CT47A11, CT47A12, CT47A2, CT47A3, CT47A4, CT47A5, CT47A6, CT47A7, CT47A8, CT47A9, CT47B1, CTAG1A, CTAG1B, CTAG2, CTAGE1, CTAGE5, CTAGE6P, CTAGE9, CTBP2, CTDNEP1, CTDSP2, CTDSPL2, CTLA4, CTNNA1, CTNND1, CTRB1, CTRB2, CTSL1, CTU1, CUBN, CUL1, CUL7, CUL9, CUTA, CUX1, CXADR, CXCL1, CXCL17, CXCL2, CXCL3, CXCL5, CXCL6, CXCR1, CXCR2, CXorf40A, CXorf40B, CXorf48, CXorf49, CXorf49B, CXorf56, CXorf61, CYB5A, CYCS, CYP11B1, CYP11B2, CYP1A1, CYP1A2, CYP21A2, CYP2A13, CYP2A6, CYP2A7, CYP2B6, CYP2C18, CYP2C19, CYP2C8, CYP2C9, CYP2D6, CYP2F1, CYP3A4, CYP3A43, CYP3A5, CYP3A7, CYP3A7-CYP3AP1, CYP46A1, CYP4A11, CYP4A22, CYP4F11, CYP4F12, CYP4F2, CYP4F3, CYP4F8, CYP4Z1, CYP51A1, CYorf17, DAP3, DAPK1, DAXX, DAZ1, DAZ2, DAZ3, DAZ4, DAZAP2, DAZL, DBF4, DCAF12L1, DCAF12L2, DCAF13, DCAF4, DCAF4L1, DCAF4L2, DCAF6, DCAF8L1, DCAF8L2, DCLRE1C, DCTN6, DCUN1D1, DCUN1D3, DDA1, DDAH2, DDB2, DDR1, DDT, DDTL, DDX10, DDX11, DDX18, DDX19A, DDX19B, DDX23, DDX26B, DDX39B, DDX3X, DDX3Y, DDX50, DDX55, DDX56, DDX6, DDX60, DDX60L, DEF8, DEFB103A, DEFB103B, DEFB104A, DEFB104B, DEFB105A, DEFB105B, DEFB106A, DEFB106B, DEFB107A, DEFB107B, DEFB108B, DEFB130, DEFB131, DEFB4A, DEFB4B, DENND1C, DENR, DEPDC1, DERL2, DESI2, DEXI, DGCR6, DGCR6L, DGKZ, DHFR, DHFRL1, DHRS2, DHRS4, DHRS4L1, DHRS4L2, DHRSX, DHX16, DHX29, DHX34, DHX40, DICER1, DIMT1, DIS3L2, DKKL1, DLEC1, DLST, DMBT1, DMRTC1, DMRTC1B, DNAH11, DNAJA1, DNAJA2, DNAJB1, DNAJB14, DNAJB3, DNAJB6, DNAJC1, DNAJC19, DNAJC24, DNAJC25-GNG10, DNAJC5, DNAJC7, DNAJC8, DNAJC9, DND1, DNM1, DOCK1, DOCK11, DOCK9, DOK1, DOM3Z, DONSON, DPCR1, DPEP2, DPEP3, DPF2, DPH3, DPM3, DPP3, DPPA2, DPPA3, DPPA4, DPPA5, DPRX, DPY19L1, DPY19L2, DPY19L3, DPY19L4, DPY30, DRAXIN, DRD5, DRG1, DSC2, DSC3, DSE, DSTN, DTD2, DTWD1, DTWD2, DTX2, DUOX1, DUOX2, DUSP12, DUSP5, DUSP8, DUT, DUXA, DYNC1I2, DYNC1LI1, DYNLT1, DYNLT3, E2F3, EBLN1, EBLN2, EBPL, ECEL1, EDDM3A, EDDM3B, EED, EEF1A1, EEF1B2, EEF1D, EEF1E1, EEF1G, EFCAB3, EFEMP1, EFTUD1, EGFL8, EGLN1, EHD1, EHD3, EHMT2, EI24, EIF1, EIF1AX, EIF2A, EIF2C1, EIF2C3, EIF2S2, EIF2S3, EIF3A, EIF3C, EIF3CL, EIF3E, EIF3F, EIF3J, EIF3L, EIF3M, EIF4A1, EIF4A2, EIF4B, EIF4E, EIF4E2, EIF4EBP1, EIF4EBP2, EIF4H, EIF5, EIF5A, EIF5A2, EIF5AL1, ELF2, ELK1, ELL2, ELMO2, EMB, EMC3, EMR1, EMR2, EMR3, ENAH, ENDOD1, ENO1, ENO3, ENPEP, ENPP7, ENSA, EP300, EP400, EPB41L4B, EPB41L5, EPCAM, EPHA2, EPHB2, EPHB3, EPN2, EPN3, EPPK1, EPX, ERCC3, ERF, ERP29, ERP44, ERVV-1, ERVV-2, ESCO1, ESF1, ESPL1, ESPN, ESRRA, ETF1, ETS2, ETV3, ETV3L, EVA1C, EVPL, EWSR1, EX005, EXOC8, EXOG, EXOSC3, EXOSC6, EXTL2, EYS, EZR, F5, F8A1, F8A2, F8A3, FABP3, FABP5, FAF2, FAHD1, FAHD2A, FAHD2B, FAM103A1, FAM104B, FAM108A1, FAM108C1, FAM111B, FAM115A, FAM115C, FAM120A, FAM120B, FAM127A, FAM127B, FAM127C, FAM131C, FAM133B, FAM136A, FAM149B1, FAM151A, FAM153A, FAM153B, FAM154B, FAM156A, FAM156B, FAM157A, FAM157B, FAM163B, FAM165B, FAM175A, FAM177A1, FAM185A, FAM186A, FAM18B1, FAM18B2, FAM190B, FAM192A, FAM197Y1, FAM197Y3, FAM197Y4, FAM197Y6, FAM197Y7, FAM197Y8, FAM197Y9, FAM203A, FAM203B, FAM204A, FAM205A, FAM206A, FAM207A, FAM209A, FAM209B, FAM20B, FAM210B, FAM213A, FAM214B, FAM218A, FAM21A, FAM21B, FAM21C, FAM220A, FAM22A, FAM22D, FAM22F, FAM22G, FAM25A, FAM25B, FAM25C, FAM25G, FAM27E4P, FAM32A, FAM35A, FAM3C, FAM45A, FAM47A, FAM47B, FAM47C, FAM47E-STBD1, FAM58A, FAM60A, FAM64A, FAM72A, FAM72B, FAM72D, FAM76A, FAM83G, FAM86A, FAM86B2, FAM86C1, FAM89B, FAM8A1, FAM90A1, FAM91A1, FAM92A1, FAM96A, FAM98B, FAM9A, FAM9B, FAM9C, FANCD2, FANK1, FAR1, FAR2, FARP1, FARSB, FASN, FASTKD1, FAT1, FAU, FBLIM1, FBP2, FBRSL1, FBXL12, FBXO25, FBXO3, FBXO36, FBXO44, FBXO6, FBXW10, FBXW11, FBXW2, FBXW4, FCF1, FCGBP, FCGR1A, FCGR2A, FCGR2B, FCGR3A, FCGR3B, FCN1, FCN2, FCRL1, FCRL2, FCRL3, FCRL4, FCRL5, FCRL6, FDPS, FDX1, FEM1A, FEV1, FER, FFAR3, FGD5, FGF7, FGFR1OP2, FH, FHL1, FIGLA, FKBP1A, FKBP4, FKBP6, FKBP8, FKBP9, FKBPL, FLG, FLG2, FLI1, FLJ44635, FLNA, FLNB, FLNC, FLOT1, FLT1, FLYWCH1, FMN2, FN3K, FOLH1, FOLH1B, FOLR1, FOLR2, FOLR3, FOSL1, FOXA1, FOXA2, FOXA3, FOXD1, FOXD2, FOXD3, FOXD4L2, FOXD4L3, FOXD4L6, FOXF1, FOXF2, FOXH1, FOXN3, FOXO1, FOXO3, FPR2, FPR3, FRAT2, FREM2, FRG1, FRG2, FRG2B, FRG2C, FRMD6, FRMD7, FRMD8, FRMPD2, FSCN1, FSIP2, FTH1, FTHL17, FTL, FTO, FUNDC1, FUNDC2, FUT2, FUT3, FUT5, FUT6, FXN, FXR1, FZD2, FZD5, FZD8, G2E3, G3BP1, GABARAP, GABARAPL1, GABBR1, GABPA, GABRP, GABRR1, GABRR2, GAGE1, GAGE10, GAGE12C, GAGE12D, GAGE12E, GAGE12F, GAGE12G, GAGE12H, GAGE12I, GAGE12J, GAGE13, GAGE2A, GAGE2B, GAGE2C, GAGE2D, GAGE2E, GAPDH, GAR1, GATS, GATSL1, GATSL2, GBA, GBP1, GBP2, GBP3, GBP4, GBP5, GBP6, GBP7, GCAT, GCDH, GCNT1, GCOM1, GCSH, GDI2, GEMIN7, GEMIN8, GFRA2, GGCT, GGT1, GGT2, GGT5, GGTLC1, GGTLC2, GH1, GH2, GINS2, GJA1, GJC3, GK, GK2, GLB1L2, GLB1L3, GLDC, GLOD4, GLRA1, GLRA4, GLRX, GLRX3, GLRX5, GLTP, GLTSCR2, GLUD1, GLUL, GLYATL1, GLYATL2, GLYR1, GM2A, GMCL1, GMFB, GMPS, GNA11, GNAQ, GNAT2, GNG10, GNG5, GNGT1, GNL1, GNL3, GNL3L, GNPNAT1, GOLGA2, GOLGA4, GOLGA5, GOLGA6A, GOLGA6B, GOLGA6C, GOLGA6D, GOLGA6L1, GOLGA6L10, GOLGA6L2, GOLGA6L3, GOLGA6L4, GOLGA6L6, GOLGA6L9, GOLGA7, GOLGA8H, GOLGA8J, GOLGA8K, GOLGA8O, GON4L, GOSR1, GOSR2, GOT2, GPAA1, GPANK1, GPAT2, GPATCH8, GPC5, GPCPD1, GPD2, GPHN, GPN1, GPR116, GPR125, GPR143, GPR32, GPR89A, GPR89B, GPR89C, GPS2, GPSM3, GPX1, GPX5, GPX6, GRAP, GRAPL, GRIA2, GRIA3, GRIA4, GRK6, GRM5, GRM8, GRPEL2, GSPT1, GSTA1, GSTA2, GSTA3, GSTA5, GSTM1, GSTM2, GSTM4, GSTM5, GSTO1, GSTT1, GSTT2, GSTT2B, GTF2A1L, GTF2H1, GTF2H2, GTF2H2C, GTF2H4, GTF2I, GTF2IRD1, GTF2IRD2, GTF2IRD2B, GTF3C6, GTPBP6, GUSB, GXYLT1, GYG1, GYG2, GYPA, GYPB, GYPE, GZMB, GZMH, H1FOO, H2AFB1, H2AFB2, H2AFB3, H2AFV, H2AFX, H2AFZ, H2BFM, H2BFWT, H3F3A, H3F3B, H3F3C, HADHA, HADHB, HARS, HARS2, HAS3, HAUS1, HAUS4, HAUS6, HAVCR1, HAX1, HBA1, HBA2, HBB, HBD, HBG1, HBG2, HBS1L, HBZ, HCAR2, HCAR3, HCN2, HCN3, HCN4, HDAC1, HDGF, HDHD1, HEATR7A, HECTD4, HERC2, HIATL1, HIBCH, HIC1, HIC2, HIGD1A, HIGD2A, HINT1, HIST1H1B, HIST1H1C, HIST1H1D, HIST1H2AA, HIST1H2AB, HIST1H2AC, HIST1H2AD, HIST1H2AE, HIST1H2AG, HIST1H2AH, HIST1H2AI, HIST1H2AL, HIST1H2BB, HIST1H2BD, HIST1H2BE, HIST1H2BF, HIST1H2BH, HIST1H2BI, HIST1H2BK, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AB, HIST2H2AC, HIST2H2BE, HIST2H2BF, HIST2H3A, HIST2H3D, HIST2H4A, HIST2H4B, HIST3H2BB, HIST3H3, HIST4H4, HK2, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB5, HLA-E, HLA-F, HLA-G, HMGA1, HMGB1, HMGB2, HMGB3, HMGCS1, HMGN1, HMGN2, HMGN3, HMGN4, HMX1, HMX3, HNRNPA1, HNRNPA3, HNRNPAB, HNRNPC, HNRNPCL1, HNRNPD, HNRNPF, HNRNPH1, HNRNPH2, HNRNPH3, HNRNPK, HNRNPL, HNRNPM, HNRNPR, HNRNPU, HNRPDL, HOMER2, HORMAD1, HOXA2, HOXA3, HOXA6, HOXA7, HOXB2, HOXB3, HOXB6, HOXB7, HOXD3, HP, HPR, HPS1, HRG, HS3ST3A1, HS3ST3B1, HS6ST1, HSD1781, HSD17812, HSD1784, HSD1786, HSD1787, HSD1788, HSD3B1, HSD3B2, HSF2, HSFX1, HSFX2, HSP90AA1, HSP90AB1, HSP90B1, HSPA1A, HSPA1B, HSPA1L, HSPA2, HSPA5, HSPA6, HSPA8, HSPA9, HSPB1, HSPD1, HSPE1, HSPE1-MOB4, HSPG2, HTN1, HTN3, HTR3C, HTR3D, HTR3E, HTR7, HYDIN, HYPK, IARS, ID2, IDH1, IDI1, IDS, IER3, IFI16, IFIH1, IFIT1, IFIT1B, IFIT2, IFIT3, IFITM3, IFNA1, IFNA10, IFNA14, IFNA16, IFNA17, IFNA2, IFNA21, IFNA4, IFNA5, IFNA6, IFNA7, IFNA8, IFT122, IFT80, IGBP1, IGF2BP2, IGF2BP3, IGFL1, IGFL2, IGFN1, IGLL1, IGLL5, IGLONS, IGSF3, IHH, IK, IKBKG, IL17RE, IL18, IL28A, IL28B, IL29, IL32, IL3RA, ILEST, IL9R, IMMP1L, IMMT, IMPA1, IMPACT, IMPDH1, ING5, INIP, INTS4, INTS6, IPMK, IP07, IPPK, IQCB1, IREB2, IRX2, IRX3, IRX4, IRX5, IRX6, ISCA1, ISCA2, ISG20L2, ISL1, ISL2, IST1, ISY1-RAB43, ITFG2, ITGAD, ITGAM, ITGAX, ITGB1, ITGB6, ITIH6, ITLN1, ITLN2, ITSN1, KAL1, KANK1, KANSL1, KARS, KAT7, KATNBL1, KBTBD6, KBTBD7, KCNA1, KCNAS, KCNA6, KCNC1, KCNC2, KCNC3, KCNH2, KCNH6, KCNJ12, KCNJ4, KCNMB3, KCTD1, KCTDS, KCTD9, KDELC1, KDM5C, KDM5D, KDM6A, KHDC1, KHDC1L, KHSRP, KIAA0020, KIAA0146, KIAA0494, KIAA0754, KIAA0895L, KIAA1143, KIAA1191, KIAA1328, KIAA1377, KIAA1462, KIAA1549L, KIAA1551, KIAA1586, KIAA1644, KIAA1671, KIAA2013, KIF1C, KIF27, KIF4A, KIF4B, KIFC 1, KIR2DL1, KIR2DL3, KIR2DL4, KIR2DS4, KIR3DL1, KIR3DL2, KIR3DL3, KLF17, KLF3, KLF4, KLF7, KLF8, KLHL12, KLHL13, KLHL15, KLHL2, KLHLS, KLHL9, KLK2, KLK3, KLRC1, KLRC2, KLRC3, KLRC4, KNTC1, KPNA2, KPNA4, KPNA7, KPNB1, KRAS, KRT13, KRT14, KRT15, KRT16, KRT17, KRT18, KRT19, KRT25, KRT27, KRT28, KRT3, KRT31, KRT32, KRT33A, KRT33B, KRT34, KRT35, KRT36, KRT37, KRT38, KRT4, KRT5, KRT6A, KRT6B, KRT6C, KRT71, KRT72, KRT73, KRT74, KRT75, KRT76, KRT8, KRT80, KRT81, KRT82, KRT83, KRT85, KRT86, KRTAP1-1, KRTAP1-3, KRTAP1-5, KRTAP10-10, KRTAP10-11, KRTAP10-12, KRTAP10-2, KRTAP10-3, KRTAP10-4, KRTAP10-7, KRTAP10-9, KRTAP12-1, KRTAP12-2, KRTAP12-3, KRTAP13-1, KRTAP13-2, KRTAP13-3, KRTAP13-4, KRTAP19-1, KRTAP19-5, KRTAP2-1, KRTAP2-2, KRTAP2-3, KRTAP2-4, KRTAP21-1, KRTAP21-2, KRTAP23-1, KRTAP3-2, KRTAP3-3, KRTAP4-12, KRTAP4-4, KRTAP4-6, KRTAP4-7, KRTAP4-9, KRTAP5-1, KRTAP5-10, KRTAP5-3, KRTAP5-4, KRTAP5-6, KRTAP5-8, KRTAP5-9, KRTAP6-1, KRTAP6-2, KRTAP6-3, KRTAP9-2, KRTAP9-3, KRTAP9-6, KRTAP9-8, KRTAP9-9, L1TD1, LAGE3, LAIR1, LAIR2, LAMTOR3, LANCL3, LAP3, LAPTM4B, LARP1, LARP1B, LARP4, LARP7, LCE1A, LCE1B, LCE1C, LCE1D, LCE1E, LCE1F, LCE2A, LCE2B, LCE2C, LCE2D, LCE3C, LCE3D, LCE3E, LCMT1, LCN1, LDHA, LDHAL6B, LDHB, LEFTY1, LEFTY2, LETM1, LGALS13, LGALS14, LGALS16, LGALS7, LGALS7B, LGALS9, LGALS9B, LGALS9C, LGMN, LGR6, LHB, LILRA1, LILRA2, LILRA3, LILRA4, LILRA5, LILRA6, LILRB1, LILRB2, LILRB3, LILRB4, LILRB5, LIMK2, LIMS1, LIN28A, LIN28B, LIN54, LLPH, LMLN, LNX1, LOC100129083, LOC100129216, LOC100129307, LOC100129636, LOC100130539, LOC100131107, LOC100131608, LOC100132154, LOC100132202, LOC100132247, LOC100132705, LOC100132858, LOC100132859, LOC100132900, LOC100133251, LOC100133267, LOC100133301, LOC100286914, LOC100287294, LOC100287368, LOC100287633, LOC100287852, LOC100288332, LOC100288646, LOC100288807, LOC100289151, LOC100289375, LOC100289561, LOC100505679, LOC100505767, LOC100505781, LOC100506248, LOC100506533, LOC100506562, LOC100507369, LOC100507607, LOC100652777, LOC100652871, LOC100652953, LOC100996256, LOC100996259, LOC100996274, LOC100996301, LOC100996312, LOC100996318, LOC100996337, LOC100996356, LOC100996369, LOC100996394, LOC100996401, LOC100996413, LOC100996433, LOC100996451, LOC100996470, LOC100996489, LOC100996541, LOC100996547, LOC100996567, LOC100996574, LOC100996594, LOC100996610, LOC100996612, LOC100996625, LOC100996631, LOC100996643, LOC100996644, LOC100996648, LOC100996675, LOC100996689, LOC100996701, LOC100996702, LOC377711, LOC388849, LOC391322, LOC391722, LOC401052, LOC402269, LOC440243, LOC440292, LOC440563, L00554223, LOC642441, LOC642643, LOC642778, LOC642799, LOC643802, LOC644634, LOC645202, LOC645359, LOC646021, LOC646670, LOC649238, LOC728026, LOC728715, LOC728728, LOC728734, LOC728741, LOC728888, LOC729020, LOC729159, LOC729162, LOC729264, LOC729458, LOC729574, LOC729587, LOC729974, LOC730058, LOC730268, LOC731932, LOC732265, LONRF2, LPA, LPCAT3, LPGAT1, LRP5, LRP5L, LRRC16B, LRRC28, LRRC37A, LRRC37A2, LRRC37A3, LRRC37B, LRRC57, LRRC59, LRRC8B, LRRFIP1, LSM12, LSM14A, LSM2, LSM3, LSP1, LTA, LTB, LUZP6, LY6G5B, LY6G5C, LY6G6C, LY6G6D, LY6G6F, LYPLA1, LYPLA2, LYRM2, LYRM5, LYST, LYZL1, LYZL2, LYZL6, MAD1L1, MAD2L1, MAGEA10-MAGEA5, MAGEA11, MAGEA12, MAGEA2B, MAGEA4, MAGEA5, MAGEA6, MAGEA9, MAGEB2, MAGEB4, MAGEB6, MAGEC1, MAGEC3, MAGED1, MAGED2, MAGED4, MAGED4B, MAGIX, MALL, MAMDC2, MAN1A1, MAN1A2, MANBAL, MANEAL, MAP1LC3B, MAP1LC3B2, MAP2K1, MAP2K2, MAP2K4, MAP3K13, MAP7, MAPK1IP1L, MAPK6, MAPK8IP1, MAPRE1, MAPT, MARC1, MARC2, MAS1L, MASP1, MAST1, MAST2, MAST3, MAT2A, MATR3, MBD3L2, MBD3L3, MBD3L4, MBD3L5, MBLAC2, MCCD1, MCF2L2, MCFD2, MCTS1, MDC 1, ME1, ME2, MEAF6, MED13, MED15, MED25, MED27, MED28, MEF2A, MEF2BNB, MEIS3, MEMO1, MEP1A, MESP1, MEST, METAP2, METTL1, METTL15, METTL21A, METTL21D, METTL2A, METTL2B, METTL5, METTL7A, METTLE, MEX3B, MEX3D, MFAP2, MFF, MFN1, MFSD2B, MGAM, MICA, MICB, MINOS1, MIPEP, MKI67, MKI67IP, MKNK1, MKRN1, MLF1IP, MLL3, MLLT10, MLLT6, MMADHC, MMP10, MMP23B, MMP3, MOB4, MOCS1, MOCS3, MOG, MORF4L1, MORF4L2, MPEG1, MPHOSPH10, MPHOSPH8, MPO, MPP7, MPPE1, MPRIP, MPV17L, MPZL1, MR1, MRC1, MRE11A, MRFAP1, MRFAP1L1, MRGPRX2, MRGPRX3, MRGPRX4, MRPL10, MRPL11, MRPL19, MRPL3, MRPL32, MRPL35, MRPL36, MRPL45, MRPL48, MRPL50, MRPL51, MRPS10, MRPS16, MRPS17, MRPS18A, MRPS18B, MRPS18C, MRPS21, MRPS24, MRPS31, MRPS33, MRPS36, MRPS5, MRRF, MRS2, MRTO4, MS4A4A, MS4A4E, MS4A6A, MS4A6E, MSANTD2, MSANTD3, MSANTD3-TMEFF1, MSH5, MSL3, MSN, MST1, MSTO1, MSX2, MT1A, MT1B, MT1E, MT1F, MT1G, MT1H, MT1M, MT1X, MT2A, MTAP, MTCH1, MTFR1, MTHFD1, MTHFD1L, MTHFD2, MTIF2, MTIF3, MTMR12, MTMR9, MTRF1L, MTRNR2L1, MTRNR2L5, MTRNR2L6, MTRNR2L8, MTX1, MUC12, MUC16, MUC19, MUC20, MUC21, MUC22, MUC5B, MUC6, MX1, MX2, MXRA5, MXRA7, MYADM, MYEOV2, MYH1, MYH11, MYH13, MYH2, MYH3, MYH4, MYH6, MYH7, MYH8, MYH9, MYL12A, MYL12B, MYL6, MYL6B, MYLK, MYO5B, MZT1, MZT2A, MZT2B, NAA40, NAALAD2, NAB1, NACA, NACA2, NA CAD, NACC2, NAGK, NAIP, NAMPT, NANOG, NANOGNB, NANP, NAP1L1, NAP1L4, NAPEPLD, NAPSA, NARG2, NARS, NASP, NAT1, NAT2, NAT8, NAT8B, NBAS, NBEA, NBEAL1, NBPF1, NBPF10, NBPF11, NBPF14, NBPF15, NBPF16, NBPF4, NBPF6, NBPF7, NBPF9, NBR1, NCAPD2, NCF1, NCOA4, NCOA6, NCOR1, NCR3, NDEL1, NDST3, NDST4, NDUFA4, NDUFA5, NDUFA9, NDUFAF2, NDUFAF4, NDUFB1, NDUFB3, NDUFB4, NDUFB6, NDUFB8, NDUFB9, NDUFS5, NDUFV2, NEB, NEDD8, NEDD8-MDP1, NEFH, NEFM, NEIL2, NEK2, NETO2, NEU1, NEUROD1, NEUROD2, NF1, NFE2L3, NFIC, NFIX, NFKBIL1, NFYB, NFYC, NHLH1, NHLH2, NHP2, NHP2L1, NICN1, NIF3L1, NIP7, NIPA2, NIPAL1, NIPSNAP3A, NIPSNAP3B, NKAP, NKX1-2, NLGN4X, NLGN4Y, NLRP2, NLRP5, NLRP7, NLRP9, NMD3, NME2, NMNAT1, NOB1, NOC2L, NOL11, NOLC1, NOMO1, NOMO2, NOMO3, NONO, NOP10, NOP56, NOS2, NOTCH2, NOTCH2NL, NOTCH4, NOX4, NPAP1, NPEPPS, NPIP, NPIPL3, NPM1, NPSR1, NR2F1, NR2F2, NR3C1, NRBF2, NREP, NRM, NSA2, NSF, NSFL1C, NSMAF, NSRP1, NSUN5, NT5C3, NT5DC1, NTM, NTPCR, NUBP1, NUDC, NUDT10, NUDT11, NUDT15, NUDT16, NUDT19, NUDT4, NUDT5, NUFIP1, NUP210, NUP35, NUP50, NUS1, NUTF2, NXF2, NXF2B, NXF3, NXF5, NXPE1, NXPE2, NXT1, OAT, OBP2A, OBP2B, OBSCN, OCLN, OCM, OCM2, ODC1, OFD1, OGDH, OGDHL, OGFOD1, OGFR, OLA1, ONECUT1, ONECUT2, ONECUT3, OPCML, OPN1LW, OPN1MW, OPN1MW2, OR10A2, OR10A3, OR10A5, OR10A6, OR10C1, OR10G2, OR10G3, OR10G4, OR10G7, OR10G8, OR10G9, OR10H1, OR10H2, OR10H3, OR10H4, OR10H5, OR10J3, OR10J5, OR10K1, OR10K2, OR10Q1, OR11A1, OR11G2, OR11H1, OR11H12, OR11H2, OR12D2, OR12D3, OR13C2, OR13C4, OR13C5, OR13C9, OR13D1, OR14J1, OR1A1, OR1A2, OR1D2, OR1D5, OR1E1, OR1E2, OR1F1, OR1J1, OR1J2, OR1J4, OR1L4, OR1L6, OR1M1, OR1S1, OR1S2, OR2A1, OR2A12, OR2A14, OR2A2, OR2A25, OR2A4, OR2A42, OR2A5, OR2A7, OR2AG1, OR2AG2, OR2B2, OR2B3, OR2B6, OR2F1, OR2F2, OR2H1, OR2H2, OR2J2, OR2J3, OR2L2, OR2L3, OR2L5, OR2L8, OR2M2, OR2M5, OR2M7, OR2S2, OR2T10, OR2T2, OR2T27, OR2T29, OR2T3, OR2T33, OR2T34, OR2T35, OR2T4, OR2T5, OR2T8, OR2V1, OR2V2, OR2W1, OR3A1, OR3A2, OR3A3, OR4A15, OR4A47, OR4C12, OR4C13, OR4C46, OR4D1, OR4D10, OR4D11, OR4D2, OR4D9, OR4F16, OR4F21, OR4F29, OR4F3, OR4K15, OR4M1, OR4M2, OR4N2, OR4N4, OR4N5, OR4P4, OR4Q3, OR51A2, OR51A4, OR52E2, OR52E6, OR52E8, OR52H1, OR5211, OR5212, OR52J3, OR52K1, OR52K2, OR52L1, OR56A1, OR56A3, OR56A4, OR56A5, OR56B4, OR5AK2, OR5B2, OR5B3, OR5D16, OR5F1, OR5H14, OR5H2, OR5H6, OR5J2, OR5L1, OR5L2, OR5M1, OR5M10, OR5M3, OR5M8, OR5P3, OR5T1, OR5T2, OR5T3, OR5V1, OR6B2, OR6B3, OR6C6, OR7A10, OR7A5, OR7C1, OR7C2, OR7G3, OR8A1, OR8B12, OR8B2, OR8B3, OR8B8, OR8G2, OR8G5, OR8H1, OR8H2, OR8H3, OR8J1, OR8J3, OR9A2, OR9A4, OR9G1, ORC3, ORM1, ORM2, OSTC, OSTCP2, OTOA, OTOP1, OTUD4, OTUD7A, OTX2, OVOS, OXCT2, OXR1, OXT, P2RX6, P2RX7, P2RY8, PA2G4, PAAF1, PABPC1, PABPC1L2A, PABPC1L2B, PABPC3, PABPC4, PABPN1, PAEP, PAFAH1B1, PAFAH1B2, PAGE1, PAGE2, PAGE2B, PAGE5, PAICS, PAIP1, PAK2, PAM, PANK3, PARG, PARL, PARN, PARP1, PARP4, PARP8, PATL1, PBX1, PBX2, PCBD2, PCBP1, PCBP2, PCDH11X, PCDH11Y, PCDH8, PCDHA1, PCDHA11, PCDHA12, PCDHA13, PCDHA2, PCDHA3, PCDHAS, PCDHA6, PCDHA7, PCDHA8, PCDHA9, PCDHB10, PCDHB11, PCDHB12, PCDHB13, PCDHB15, PCDHB16, PCDHB4, PCDHB8, PCDHGA1, PCDHGA11, PCDHGA12, PCDHGA2, PCDHGA3, PCDHGA4, PCDHGA5, PCDHGA7, PCDHGA8, PCDHGA9, PCDHGB1, PCDHGB2, PCDHGB3, PCDHGB5, PCDHGB7, PCGF6, PCMTD1, PCNA, PCNP, PCNT, PCSK5, PCSK7, PDAP1, PDCD2, PDCD5, PDCD6, PDCD6IP, PDCL2, PDCL3, PDE4DIP, PDIA3, PDLIM1, PDPK1, PDPR, PDSS1, PDXDC1, PDZD11, PDZK1, PEBP1, PEF1, PEPD, PERP, PEX12, PEX2, PF4, PF4V1, PFDN1, PFDN4, PFDN6, PFKFB1, PFN1, PGA3, PGA4, PGA5, PGAM1, PGAM4, PGBD3, PGBD4, PGD, PGGT1B, PGK1, PGK2, PGM5, PHAX, PHB, PHC1, PHF1, PHF10, PHF2, PHF5A, PHKA1, PHLPP2, PHOSPH01, PI3, PI4K2A, PI4KA, PIEZ02, PIGA, PIGF, PIGH, PIGN, PIGY, PIK3CA, PIK3CD, PILRA, PIN1, PIN4, PIP5K1A, PITPNB, PKD1, PKM, PKP2, PKP4, PLA2G10, PLA2G12A, PLA2G4C, PLACE, PLAC9, PLAGL2, PLD5, PLEC, PLEKHA3, PLEKHA8, PLEKHM1, PLG, PLGLB1, PLGLB2, PLIN2, PLIN4, PLK1, PLLP, PLSCR1, PLSCR2, PLXNA1, PLXNA2, PLXNA3, PLXNA4, PM20D1, PMCH, PMM2, PMPCA, PMS2, PNKD, PNLIP, PNLIPRP2, PNMA6A, PNMA6B, PNMA6C, PNMA6D, PN01, PNPLA4, PNPT1, POLD2, POLE3, POLH, POLR2E, POLR2J, POLR2J2, POLR2J3, POLR2M, POLR3D, POLR3G, POLR3K, POLRMT, POM121, POM121C, POMZP3, PO TEA, POTEC, POTED, PO TEE, POTEF, POTEH, POTEI, POTEJ, POTEM, POU3F1, POU3F2, POU3F3, POU3F4, POU4F2, POU4F3, POU5F1, PPA1, PPAT, PPBP, PPCS, PPEF2, PPFIBP1, PPIA, PPIAL4C, PPIAL4D, PPIAL4E, PPIAL4F, PPIE, PPIG, PPIL1, PPIP5K1, PPIP5K2, PPM1A, PPP1R11, PPP1R12B, PPP1R14B, PPP1R18, PPP1R2, PPP1R26, PPP1R8, PPP2CA, PPP2CB, PPP2R2D, PPP2R3B, PPP2R5C, PPP2R5E, PPP4R2, PPP5C, PPP5D1, PPP6R2, PPP6R3, PPT2, PPY, PRADC1, PRAMEF1, PRAMEF10, PRAMEF11, PRAMEF12, PRAMEF13, PRAMEF14, PRAMEF15, PRAMEF16, PRAMEF17, PRAMEF18, PRAMEF19, PRAMEF20, PRAMEF21, PRAMEF22, PRAMEF23, PRAMEF25, PRAMEF3, PRAMEF4, PRAMEF5, PRAMEF6, PRAMEF7, PRAMEF8, PRAMEF9, PRB1, PRB2, PRB3, PRB4, PRDM7, PRDM9, PRDX1, PRDX2, PRDX3, PRDX6, PRELID1, PRG4, PRH1, PRH2, PRKAR1A, PRKCI, PRKRA, PRKRIR, PRKX, PRMT1, PRMT5, PRODH, PROKR1, PROKR2, PROS 1, PRPF3, PRPF38A, PRPF4B, PRPS1, PRR12, PRR13, PRR20A, PRR20B, PRR20C, PRR20D, PRR20E, PRR21, PRR23A, PRR23B, PRR23C, PRR3, PRR5-ARHGAP8, PRRC2A, PRRC2C, PRRT1, PRSS1, PRSS21, PRSS3, PRSS41, PRSS42, PRSS48, PRUNE, PRY, PRY2, PSAT1, PSG1, PSG11, PSG2, PSG3, PSG4, PSG5, PSG6, PSG8, PSG9, PSIP1, PSMA6, PSMB3, PSMB5, PSMB8, PSMB9, PSMC1, PSMC2, PSMC3, PSMC5, PSMC6, PSMD10, PSMD12, PSMD2, PSMD4, PSMD7, PSMD8, PSME2, PSORS1C1, PSORS1C2, PSPH, PTBP1, PTCD2, PTCH1, PTCHD3, PTCHD4, PTEN, PTGES3, PTGES3L-AARSD1, PTGR1, PTMA, PTMS, PTOV1, PTP4A1, PTP4A2, PTPN11, PTPN2, PTPN20A, PTPN20B, PTPRD, PTPRH, PTPRM, PTPRN2, PTPRU, PTTG1, PTTG2, PVRIG, PVRL2, PWWP2A, PYGB, PYGL, PYHIN1, PYROXD1, PYURF, PYY, PZP, QRSL1, R3HDM2, RAB11A, RAB11FIP1, RAB13, RAB18, RAB1A, RAB1B, RAB28, RAB31, RAB40AL, RAB40B, RAB42, RAB43, RAB5A, RAB5C, RAB6A, RAB6C, RAB9A, RABGEF1, RABGGTB, RABL2A, RABL2B, RABL6, RAC1, RACGAP1, RAD1, RAD17, RAD21, RAD23B, RAD51AP1, RAD54L2, RAET1G, RAET1L, RALA, RALBP1, RALGAPA1, RAN, RANBP1, RANBP17, RANBP2, RANBP6, RAP1A, RAP1B, RAP1GDS1, RAP2A, RAP2B, RARS, RASA4, RASA4B, RASGRP2, RBAK, RBAK-LOC389458, RBBP4, RBBP6, RBM14-RBM4, RBM15, RBM17, RBM39, RBM4, RBM43, RBM48, RBM48, RBM7, RBM8A, RBMS1, RBMS2, RBMX, RBMX2, RBMXL1, RBMXL2, RBMY1A1, RBMY1B, RBMY1D, RBMY1E, RBMY1F, RBMY1J, RBPJ, RCBTB1, RCBTB2, RCC2, RCN1, RCOR2, RDBP, RDH16, RDM1, RDX, RECQL, REG1A, REG1B, REG3A, REG3G, RELA, RERE, RETSAT, REV1, REXO4, RFC3, RFESD, RFK, RFPL1, RFPL2, RFPL3, RFPL4A, RFTN1, RFWD2, RGL2, RGPD1, RGPD2, RGPD3, RGPD4, RGPD5, RGPD6, RGPD8, RGS17, RGS19, RGS9, RHBDF1, RHCE, RHD, RHEB, RHOQ, RHOT1, RHOXF2, RHOXF2B, RHPN2, RIMBP3, RIMBP3B, RIMBP3C, RIMKLB, RING1, RLIM, RLN1, RLN2, RLTPR, RMND1, RMND5A, RNASE2, RNASE3, RNASE7, RNASE8, RNASEH1, RNASET2, RNF11, RNF123, RNF126, RNF13, RNF138, RNF14, RNF141, RNF145, RNF152, RNF181, RNF2, RNF216, RNF39, RNF4, RNF5, RNF6, RNFT1, RNMTL1, RNPC3, RNPS1, ROBO2, ROCK1, ROPN1, ROPN1B, RORA, RP9, RPA2, RPA3, RPAP2, RPE, RPF2, RPGR, RPL10, RPL10A, RPL10L, RPL12, RPL13, RPL14, RPL15, RPL17, RPL17-C18ORF32, RPL18A, RPL19, RPL21, RPL22, RPL23, RPL23A, RPL24, RPL26, RPL26L1, RPL27, RPL27A, RPL29, RPL3, RPL30, RPL31, RPL32, RPL35, RPL35A, RPL36, RPL36A, RPL36A-HNRNPH2, RPL36AL, RPL37, RPL37A, RPL39, RPL4, RPL41, RPL5, RPL6, RPL7, RPL7A, RPL7L1, RPL8, RPL9, RPLP0, RPLP1, RPP21, RPS10, RPS10-NUDT3, RPS11, RPS13, RPS14, RPS15, RPS15A, RPS16, RPS17, RPS17L, RPS18, RPS19, RPS2, RPS20, RPS23, RPS24, RPS25, RPS26, RPS27, RPS27A, RPS28, RPS3, RPS3A, RPS4X, RPS4Y1, RPS4Y2, RPS5, RPS6, RPS6KB1, RPS7, RPS8, RPS9, RPSA, RPTN, RRAGA, RRAGB, RRAS2, RRM2, RRN3, RRP7A, RSL24D1, RSPH10B, RSPH10B2, RSPO2, RSRC1, RSU1, RTEL1, RTN3, RTN4IP1, RTN4R, RTP1, RTP2, RUFY3, RUNDC1, RUVBL2, RWDD1, RWDD4, RXRB, RYK, S100A11, S100A7L2, SAA1, SAA2, SAA2-SAA4, SAE1, SAFB, SAFB2, SAGE1, SALL1, SALL4, SAMD12, SAMD9, SAMD9L, SAP18, SAP25, SAP30, SAPCD1, SAPCD2, SAR1A, SATL1, SAV1, SAYSD1, SBDS, SBF1, SCAMPI, SCAND3, SCD, SCGB1D1, SCGB1D2, SCGB1D4, SCGB2A1, SCGB2A2, SCGB2B2, SCN10A, SCN1A, SCN2A, SCN3A, SCN4A, SCN5A, SCN9A, SCOC, SCXA, SCXB, SCYL2, SDAD1, SDCBP, SDCCAG3, SDHA, SDHB, SDHC, SDHD, SDR42E1, SEC11A, SEC14L1, SEC14L4, SEC14L6, SEC61B, SEC63, SELT, SEMA3E, SEMG1, SEMG2, SEPHS1, SEPHS2, SEPT14, SEPT7, SERBP1, SERF1A, SERF1B, SERF2, SERHL2, SERPINB3, SERPINB4, SERPINH1, SET, SETD8, SF3A2, SF3A3, SF3B14, SF3B4, SFR 1, SFRP4, SFTA2, SFTPA1, SFTPA2, SH2D1B, SH3BGRL3, SH3GL1, SHANK2, SHC1, SHCBP1, SHFM1, SHH, SHISA5, SHMT1, SHOX, SHQ 1, SHROOM2, SIGLEC10, SIGLEC11, SIGLEC12, SIGLEC14, SIGLEC5, SIGLEC6, SIGLEC7, SIGLEC8, SIGLEC9, SIMC1, SIN3A, SIRPA, SIRPB1, SIRPG, SIX1, SIX2, SKA2, SKIV2L, SKOR2, SKP1, SKP2, SLAIN2, SLAMF6, SLC10A5, SLC16A14, SLC16A6, SLC19A3, SLC22A10, SLC22A11, SLC22A12, SLC22A24, SLC22A25, SLC22A3, SLC22A4, SLC22A5, SLC22A9, SLC25A13, SLC25A14, SLC25A15, SLC25A20, SLC25A29, SLC25A3, SLC25A33, SLC25A38, SLC25A47, SLC25A5, SLC25A52, SLC25A53, SLC25A6, SLC29A4, SLC2A13, SLC2A14, SLC2A3, SLC31A1, SLC33A1, SLC35A4, SLC35E1, SLC35E2, SLC35E2B, SLC35G3, SLC35G4, SLC35G5, SLC35G6, SLC36A1, SLC36A2, SLC39A1, SLC39A7, SLC44A4, SLC4A1AP, SLC52A1, SLC52A2, SLC5A6, SLC5A8, SLC6A14, SLC6A6, SLC6A8, SLC7A5, SLC8A2, SLC8A3, SLC9A2, SLC9A4, SLC9A7, SLCO1B1, SLCO1B3, SLCO1B7, SLFN11, SLFN12, SLFN12L, SLFN13, SLFN5, SLIRP, SLMO2, SLX1A, SLX1B, SMARCE1, SMC3, SMC5, SMEK2, SMG1, SMN1, SMN2, SMR3A, SMR3B, SMS, SMU1, SMURF2, SNAI1, SNAPC4, SNAPC5, SNF8, SNRNP200, SNRPA1, SNRPB2, SNRPC, SNRPD1, SNRPD2, SNRPE, SNRPG, SNRPN, SNW1, SNX19, SNX25, SNX29, SNX5, SNX6, SOCS5, SOCS6, SOGA1, SOGA2, SON, SOX1, SOX10, SOX14, SOX2, SOX30, SOX5, SOX9, SP100, SP140, SP140L, SP3, SPS, SP8, SP9, SPACA5, SPACA5B, SPACA7, SPAG11A, SPAG11B, SPANXA1, SPANXB1, SPANXD, SPANXN2, SPANXN5, SPATA16, SPATA20, SPATA31A1, SPATA31A2, SPA TA31A3, SPATA31A4, SPA TA31A5, SPATA31A6, SPA TA31A7, SPATA31C1, SPATA31C2, SPATA31D1, SPATA31D3, SPATA31D4, SPATA31E1, SPCS2, SPDYE1, SPDYE2, SPDYE2L, SPDYE3, SPDYE4, SPDYE5, SPDYE6, SPECC1, SPECC1L, SPHAR, SPIC, SPIN1, SPIN2A, SPIN2B, SPOPL, SPPL2A, SPPL2C, SPR, SPRR1A, SPRR1B, SPRR2A, SPRR2B, SPRR2D, SPRR2E, SPRR2F, SPRY3, SPRYD4, SPTLC1, SRD5A1, SRD5A3, SREK1IP1, SRGAP2, SRP14, SRP19, SRP68, SRP72, SRP9, SRPK1, SRPK2, SRRM1, SRSF1, SRSF10, SRSF11, SRSF3, SRSF6, SRSF9, SRXN1, SS18L2, SSB, SSBP2, SSBP3, SSBP4, SSNA1, SSR3, SSX1, SSX2, SSX2B, SSX3, SSX4, SSX4B, SSX5, SSX7, ST13, ST3GAL1, STAG3, STAR, STAT5A, STAT5B, STAU1, STAU2, STBD1, STEAP1, STEAP1B, STH, STIP1, STK19, STK24, STK32A, STMN1, STMN2, STMN3, STRADB, STRAP, STRC, STRN, STS, STUB1, STX18, SUB1, SUCLA2, SUCLG2, SUDS3, SUGP1, SUGT1, SULT1A1, SULT1A2, SULT1A3, SULT1A4, SUMF2, SUMO1, SUMO2, SUPT16H, SUPT4H1, SUSD2, SUZ12, SVIL, SWI5, SYCE2, SYNCRIP, SYNGAP1, SYNGR2, SYT14, SYT15, SYT2, SYT3, SZRD1, TAAR6, TAAR8, TACC1, TADA1, TAF1, TAF15, TAF1L, TAF4B, TAF5L, TAF9, TAF9B, TAGLN2, TALDO1, TANC2, TAP1, TAP2, TAPBP, TARBP2, TARDBP, TARP, TAS2R19, TAS2R20, TAS2R30, TAS2R39, TAS2R40, TAS2R43, TAS2R46, TAS2R50, TASP1, TATDN1, TATDN2, TBC1D26, TBC1D27, TBC1D28, TBC1D29, TBC1D2B, TBC1D3, TBC1D3B, TBC1D3C, TBC1D3F, TBC1D3G, TBC1D3H, TBCA, TBCCD1, TBL1X, TBL1XR1, TBL1Y, TBPL1, TBX20, TC2N, TCEA1, TCEAL2, TCEAL3, TCEAL5, TCEB1, TCEB2, TCEB3B, TCEB3C, TCEB3CL, TCEB3CL2, TCERG1L, TCF19, TCF3, TCHH, TCL1B, TCOF1, TCP1, TCP10, TCP10L, TCP10L2, TDG, TDGF1, TDRD1, TEAD1, TEC, TECR, TEKT4, TERF1, TERF2IP, TET1, TEX13A, TEX13B, TEX28, TF, TFB2M, TFDP3, TFG, TGIF1, TGIF2, TGIF2LX, TGIF2LY, THAP3, THAP5, THEM4, THOC3, THRAP3, THSD1, THUMPD1, TIMM17B, TIMM23B, TIMM8A, TIMM8B, TIMP4, TIPIN, TJAP1, TJP3, TLE1, TLE4, TLK1, TLK2, TLL1, TLR1, TLR6, TMA16, TMA7, TMC6, TMCC1, TMED10, TMED2, TMEM126A, TMEM128, TMEM132B, TMEM132C, TMEM14B, TMEM14C, TMEM161B, TMEM167A, TMEM183A, TMEM183B, TMEM185A, TMEM185B, TMEM189-UBE2V1, TMEM191B, TMEM191C, TMEM230, TMEM231, TMEM236, TMEM242, TMEM251, TMEM254, TMEM30B, TMEM47, TMEM69, TMEM80, TMEM92, TMEM97, TMEM98, TMLHE, TMPRSS11E, TMSB10, TMSB15A, TMSB15B, TMSB4X, TMSB4Y, TMTC1, TMTC4, TMX1, TMX2, TNC, TNF, TNFRSF10A, TNFRSF10B, TNFRSF10C, TNFRSF10D, TNFRSF13B, TNFRSF14, TNIP2, TNN, TNPO1, TNRC18, TNXB, TOB2, TOE1, TOMM20, TOMM40, TOMM6, TOMM7, TOP1, TOP3B, TOR1B, TOR3A, TOX4, TP53TG3, TP53TG3B, TP53TG3C, TPD52L2, TPI1, TPM3, TPM4, TPMT, TPRKB, TPRX1, TPSAB1, TPSB2, TPSD1, TPT1, TPTE, TPTE2, TRA2A, TRAF6, TRAPPC2, TRAPPC2L, TREH, TREML2, TREML4, TRIM10, TRIM15, TRIM16, TRIM16L, TRIM26, TRIM27, TRIM31, TRIM38, TRIM39, TRIM39-RPP21, TRIM40, TRIM43, TRIM43B, TRIM48, TRIM49, TRIM49B, TRIM49C, TRIM49DP, TRIM49L1, TRIM50, TRIM51, TRIM51GP, TRIM60, TRIM61, TRIM64, TRIM64B, TRIM64C, TRIM73, TRIM74, TRIM77P, TRIP11, TRMT1, TRMT11, TRMT112, TRMT2B, TRNT1, TRO, TRPA1, TRPC6, TRPV5, TRPV6, TSC22D3, TSEN15, TSEN2, TSPAN11, TSPY1, TSPY10, TSPY2, TSPY3, TSPY4, TSPY8, TSPYL1, TSPYL6, TSR 1, TSSK1B, TSSK2, TTC28, TTC3, TTC30A, TTC30B, TTC4, TTL, TTLL12, TTLL2, TTN, TUBA1A, TUBA1B, TUBA1C, TUBA3C, TUBA3D, TUBA3E, TUBA4A, TUBAE, TUBB, TUBB2A, TUBB2B, TUBB3, TUBB4A, TUBB4B, TUBB6, TUBB8, TUBE1, TUBG1, TUBG2, TUBGCP3, TUBGCP6, TUFM, TWF1, TWIST2, TXLNG, TXN2, TXNDC2, TXNDC9, TYR, TYRO3, TYW1, TYW1B, U2AF1, UAP1, UBA2, UBA5, UBD, UBE2C, UBE2D2, UBE2D3, UBE2D4, UBE2E3, UBE2F, UBE2H, UBE2L3, UBE2M, UBE2N, UBE2Q2, UBE2S, UBE2V1, UBE2V2, UBE2W, UBE3A, UBFD1, UBQLN1, UBQLN4, UBTFL1, UBXN2B, UFD1L, UFM1, UGT1A10, UGT1A3, UGT1A4, UGT1A5, UGT1A7, UGT1A8, UGT1A9, UGT2A1, UGT2A2, UGT2A3, UGT2B10, UGT2B11, UGT2B15, UGT2B17, UGT2B28, UGT2B4, UGT2B7, UGT3A2, UHRF1, UHRF2, ULBP1, ULBP2, ULBP3, ULK4, UNC93A, UNC93B1, UPF3A, UPK3B, UPK3BL, UQCR10, UQCRB, UQCRFS1, UQCRH, UQCRQ, USP10, USP12, USP13, USP17L10, USP17L11, USP17L12, USP17L13, USP17L15, USP17L17, USP17L18, USP17L19, USP17L1P, USP17L2, USP17L20, USP17L21, USP17L22, USP17L24, USP17L25, USP17L26, USP17L27, USP17L28, USP17L29, USP17L3, USP17L30, USP17L4, USP17L5, USP17L7, USP17L8, USP18, USP22, USP32, USP34, USP6, USPS, USP9X, USP9Y, UTP14A, UTP14C, UTP18, UTP6, VAMPS, VAMP7, VAPA, VARS, VARS2, VCX, VCX2, VCX3A, VCX3B, VCY, VCY1B, VDAC1, VDAC2, VDAC3, VENTX, VEZF1, VKORC1, VKORC1L1, VMA21, VN1R4, VNN1, VOPP1, VPS26A, VPS35, VPS37A, VPS51, VPS52, VSIG10, VTCN1, VTI1B, VWA5B2, VWA7, VWA8, VWF, WARS, WASF2, WASF3, WASH1, WBP1, WBP11, WBP1L, WBSCR16, WDR12, WDR45, WDR45L, WDR46, WDR49, WDR59, WDR70, WDR82, WDR89, WFDC10A, WFDC10B, WHAMM, WHSC1L1, WIPI2, WIZ, WNT3, WNT3A, WNT5A, WNT5B, WNT9B, WRN, WTAP, WWC2, WWC3, WWP1, XAGE1A, XAGE1B, XAGE1C, XAGE1D, XAGE1E, XAGE2, XAGE3, XAGE5, XBP1, XCL1, XCL2, XG, XIAP, XKR3, XKR8, XKRY, XKRY2, XPO6, XPOT, XRCC6, YAP1, YBX1, YBX2, YES1, YME1L1, YPEL5, YTHDC1, YTHDF1, YTHDF2, YWHAB, YWHAE, YWHAQ, YWHAZ, YY1, YY1AP1, ZAN, ZBED1, ZBTB10, ZBTB12, ZBTB22, ZBTB44, ZBTB45, ZBTB8OS, ZBTB9, ZC3H11A, ZC3H12A, ZCCHC10, ZCCHC12, ZCCHC17, ZCCHC18, ZCCHC2, ZCCHC7, ZCCHC9, ZCRB1, ZDHHC11, ZDHHC20, ZDHHC3, ZDHHC8, ZEB2, ZFAND5, ZFAND6, ZFP106, ZFP112, ZFP14, ZFP57, ZFP64, ZFP82, ZFR, ZFX, ZFY, ZFYVE1, ZFYVE9, ZIC1, ZIC2, ZIC3, ZIC4, ZIK1, ZKSCAN3, ZKSCAN4, ZMIZ1, ZMIZ2, ZMYM2, ZMYM5, ZNF100, ZNF101, ZNF107, ZNF114, ZNF117, ZNF12, ZNF124, ZNF131, ZNF135, ZNF14, ZNF140, ZNF141, ZNF146, ZNF155, ZNF160, ZNF167, ZNF17, ZNF181, ZNF185, ZNF20, ZNF207, ZNF208, ZNF212, ZNF221, ZNF222, ZNF223, ZNF224, ZNF225, ZNF226, ZNF229, ZNF230, ZNF233, ZNF234, ZNF235, ZNF248, ZNF253, ZNF254, ZNF257, ZNF259, ZNF26, ZNF264, ZNF266, ZNF267, ZNF280A, ZNF280B, ZNF282, ZNF283, ZNF284, ZNF285, ZNF286A, ZNF286B, ZNF300, ZNF302, ZNF311, ZNF317, ZNF320, ZNF322, ZNF323, ZNF324, ZNF324B, ZNF33A, ZNF33B, ZNF341, ZNF347, ZNF35, ZNF350, ZNF354A, ZNF354B, ZNF354C, ZNF366, ZNF37A, ZNF383, ZNF396, ZNF41, ZNF415, ZNF416, ZNF417, ZNF418, ZNF419, ZNF426, ZNF429, ZNF43, ZNF430, ZNF431, ZNF433, ZNF439, ZNF44, ZNF440, ZNF441, ZNF442, ZNF443, ZNF444, ZNF451, ZNF460, ZNF468, ZNF470, ZNF479, ZNF480, ZNF484, ZNF486, ZNF491, ZNF492, ZNF506, ZNF528, ZNF532, ZNF534, ZNF543, ZNF546, ZNF547, ZNF548, ZNF552, ZNF555, ZNF557, ZNF558, ZNF561, ZNF562, ZNF563, ZNF564, ZNF57, ZNF570, ZNF578, ZNF583, ZNF585A, ZNF585B, ZNF586, ZNF587, ZNF587B, ZNF589, ZNF592, ZNF594, ZNF595, ZNF598, ZNF605, ZNF607, ZNF610, ZNF613, ZNF614, ZNF615, ZNF616, ZNF620, ZNF621, ZNF622, ZNF625, ZNF626, ZNF627, ZNF628, ZNF646, ZNF649, ZNF652, ZNF655, ZNF658, ZNF665, ZNF673, ZNF674, ZNF675, ZNF676, ZNF678, ZNF679, ZNF680, ZNF681, ZNF682, ZNF69, ZNF700, ZNF701, ZNF705A, ZNF705B, ZNF705D, ZNF705E, ZNF705G, ZNF706, ZNF708, ZNF709, ZNF710, ZNF714, ZNF716, ZNF717, ZNF718, ZNF720, ZNF721, ZNF726, ZNF727, ZNF728, ZNF729, ZNF732, ZNF735, ZNF736, ZNF737, ZNF746, ZNF747, ZNF749, ZNF75A, ZNF75D, ZNF761, ZNF763, ZNF764, ZNF765, ZNF766, ZNF770, ZNF773, ZNF775, ZNF776, ZNF777, ZNF780A, ZNF780B, ZNF782, ZNF783, ZNF791, ZNF792, ZNF799, ZNF805, ZNF806, ZNF808, ZNF812, ZNF813, ZNF814, ZNF816, ZNF816-ZNF321P, ZNF823, ZNF829, ZNF83, ZNF836, ZNF84, ZNF841, ZNF844, ZNF845, ZNF850, ZNF852, ZNF878, ZNF879, ZNF880, ZNF90, ZNF91, ZNF92, ZNF93, ZNF98, ZNF99, ZNRD1, ZNRF2, ZP3, ZRSR2, ZSCAN5A, ZSCAN5B, ZSCAN5D, ZSWIM5, ZXDA, ZXDB, and ZXDC.

In some embodiments a gene of interest is selected from the group of NEB, PMS2, HBA1, HBA2, HBG1, HBG2, HBB, HBD, SBDS, VWF, CYP2D6, CYP21A2, PKD1, PRSS1, GBA, SMN1, NF1, MYH6, MYH7, CALM1, CALM2, CALM3, HYDN, and PTEN.

In some embodiments a gene of interest of a subject is selected from PMS2, HBA1, HBG1, HBB, SBSD, and VWF. In certain embodiments, a gene of interest of a subject is PMS2 and the counterpart gene of the gene of interest is PMS2CL. In certain embodiments, a gene of interest of a subject is HBA1 and the counterpart gene of the gene of interest is HBA2. In certain embodiments, a gene of interest of a subject is HBG1 and the counterpart gene of the gene of interest is HBG2. In certain embodiments, a gene of interest of a subject is HBB and the counterpart gene of the gene of interest is HBD. In certain embodiments, a gene of interest of a subject is SBDS and the counterpart gene of the gene of interest is SBDSP1. In some embodiments a gene of interest of a subject is selected from CYP2D6, CYP21A2, PKD1 and PRSS1.

The term "percent identical", "% identical" or "percent identity" refers to sequence identity between two polynucleotide sequences. Identity can be determined by comparing a position in each sequence which may be aligned for purposes of comparison. When an equivalent position in the compared sequences is occupied by the same nucleotide, then the molecules are identical at that position. When the equivalent site is occupied by the same or a similar nucleotide, then the molecules can be referred to as homologous (similar) at that position. Expression as a percentage of homology, similarity, or identity refers to a function of the number of identical or similar nucleotides at positions shared by the compared sequences. Expression as a percentage of homology, similarity, or identity refers to a function of the number of identical or similar nucleotides at positions shared by the compared sequences. Any suitable algorithm or program can be used to determine homology, similarity or identity. Non-limiting examples of alignment algorithms and/or programs that may be used to determine homology, similarity and/or identity include FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each nucleotide gap is weighted as if it were a single nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Nucleic Acid Isolation & Purification

Nucleic acid may be derived, isolated, extracted, purified or partially purified from one or more subjects, one or more samples or one or more sources using suitable methods known in the art. In certain embodiments, a gene, or portions thereof, is isolated from, purified from, extracted from or derived from one or more subjects. Any suitable method can be used for isolating, extracting and/or purifying nucleic acid.

The term "isolated" as used herein refers to nucleic acid removed from its original environment (e.g., the natural environment if it is naturally occurring, or a host cell if expressed exogenously), and thus is altered by human intervention from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate, salts, buffers, detergents, and the like, or combinations thereof) than the amount of non-nucleic acid components present prior to subjecting the nucleic acid to a purification procedure. A composition comprising purified nucleic acid may be at least about 60%, 70%, 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. A composition comprising purified nucleic acid may comprise at least 80%, 81%, 82%, 83%, 84%, 85%, 86%, 87%, 88%, 89%, 90%, 91%, 92%, 93%, 94%, 95%, 96%, 97%, 98%, 99% or greater than 99% of the total nucleic acid present in a sample prior to application of a purification method.

Nucleic Acid Sequencing

In certain embodiments nucleic acids (e.g., amplicons, nucleic acids of a library, captured nucleic acids) are analyzed by a process comprising nucleic acid sequencing. In some embodiments, nucleic acids may be sequenced. In some embodiments, a full or substantially full sequence is obtained and sometimes a partial sequence is obtained.

A suitable method of sequencing nucleic acids can be used, non-limiting examples of which include Maxim & Gilbert, Sanger, chain-termination methods, sequencing by synthesis, sequencing by ligation, sequencing by mass spectrometry, microscopy-based techniques, the like or combinations thereof. In some embodiments, a high-throughput sequencing method is used. High-throughput sequencing methods generally involve clonally amplified DNA templates or single DNA molecules that are sequenced in a massively parallel fashion, sometimes within a flow cell. Next generation (e.g., 2nd and 3rd generation, etc.) sequencing (NGS) techniques are capable of sequencing DNA in a massively parallel fashion and can be used for methods described herein. NGS and "massively parallel sequencing" (MPS) methods are collectively referred to herein as MPS. Any suitable MPS or next generation sequencing method, system or technology platform for conducting methods described herein can be used to obtain sequencing reads, non-limiting examples of which include Illumina/Solex/HiSeq (e.g., Illumina's Genome Analyzer; Genome Analyzer II; HISEQ 2000; HISEQ 2500, SOLiD, Roche/454, PACBIO, SMRT, Helicos True Single Molecule Sequencing, Ion Torrent and Ion semiconductor-based sequencing, Wld-Fire, 5500, 5500xl W and/or 5500xl W Genetic Analyzer based technologies (e.g., as developed and sold by Life Technologies), Polony sequencing; Pyrosequencing, Massively Parallel Signature Sequencing, RNA polymerase (RNAP) sequencing, IBS methods, LaserGen systems and methods, chemical-sensitive field effect transistor (CHEMFET) array, electron microscopy-based sequencing, nanoball sequencing, sequencing-by-synthesis, sequencing by ligation, sequencing-by-hybridization, the like or variations thereof. Additional sequencing technologies that include the use of developing nucleic acid imaging technologies (e.g., transmission electron microscopy (TEM) and atomic force microscopy (AFM)), also are contemplated herein. In some embodiments, a high-throughput sequencing method is used. High-throughput sequencing methods generally involve clonally amplified DNA templates or single DNA molecules that are sequenced in a massively parallel fashion, sometimes within a flow cell. In some embodiments MPS sequencing methods utilize a targeted approach, where sequence reads are generated from specific chromosomes, genes or regions of interest. Specific chromosomes, genes or regions of interest are sometimes referred to herein as targeted genomic regions. In certain embodiments a non-targeted approach is used where most or all nucleic acid fragments in a sample are sequenced, amplified and/or captured randomly. In certain embodiments sequence reads are obtained by a method comprising paired-end sequencing. In certain embodiments, a first generation technology, such as, for example, Sanger sequencing methods including automated Sanger sequencing methods, including microfluidic Sanger sequencing, can be used in a method provided herein for the purpose of confirming whether a variation detected to be in either of the gene of interest or the counterpart is in fact in the gene of interest.

Sequence Reads

Subjecting a nucleic acid to a sequencing method often provides sequence reads. Sequence reads can be obtained by any suitable nucleic acid sequencing method. In certain embodiments, sequence reads are obtained by an MPS method. As used herein, "reads" (e.g., "a read", "a sequence read") are short nucleotide sequences produced by any sequencing process described herein or known in the art. Reads can be generated from one end of a nucleic acid fragment ("single-end reads"), and sometimes are generated from both ends of a nucleic acid fragment (e.g., paired-end reads, paired-end sequence reads, double-end reads). Paired end reads often include one or more pairs of reads (e.g., two reads, a read mate pair) were each pair of reads is obtained from each end of a nucleic acid fragment that was sequenced. Each read of a read mate pair is sometimes referred to herein as a read mate. A paired end sequencing approach (e.g., where one or more libraries of nucleic acids are sequenced) often results in a plurality of read mate pairs and a plurality of read mates.

The length of a sequence read is often associated with the particular sequencing technology. High-throughput methods and/or next generation sequencing, for example, provide sequence reads that can vary in size from tens to hundreds of base pairs (bp). In some embodiments, sequence reads are of a mean, median, average or absolute length of about 15 bp to about 900 bp long. In certain embodiments sequence reads are of a mean, median, average or absolute length about 1000 bp or more.

Single end reads can be of any suitable length. In some embodiments the nominal, average, mean or absolute length of single-end reads sometimes is about 10 nucleotides to about 1000 contiguous nucleotides, about 10 nucleotide to about 500 contiguous nucleotides, about 10 nucleotide to about 250 contiguous nucleotides, about 10 nucleotide to about 200 contiguous nucleotides, about 10 nucleotide to about 150 contiguous nucleotides, about 15 contiguous nucleotides to about 100 contiguous nucleotides, about 20 contiguous nucleotides to about 75 contiguous nucleotides, or about 30 contiguous nucleotides or about 50 contiguous nucleotides. In certain embodiments the nominal, average, mean or absolute length of single-end reads is about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 or more nucleotides in length.

Paired-end reads (e.g., read mates) can be of any suitable length. In certain embodiments, both ends of a nucleic acid fragment are sequenced at a suitable read length that is sufficient to map each read (e.g., reads of both ends of a fragment template) to a reference genome. In certain embodiments, the nominal, average, mean or absolute length of paired-end reads is about 10 contiguous nucleotides to about 500 contiguous nucleotides, about 10 contiguous nucleotides to about 400 contiguous nucleotides, about 10 contiguous nucleotides to about 300 contiguous nucleotides, about 50 contiguous nucleotides to about 200 contiguous nucleotides, about 100 contiguous nucleotides to about 200 contiguous nucleotides, or about 100 contiguous nucleotides to about 150 contiguous nucleotides. In certain embodiments, the nominal, average, mean or absolute length of paired-end reads is about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170 or more nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. A mixture of relatively short reads can be transformed by processes described herein into a representation of a genomic nucleic acid present in subject. A mixture of relatively short reads can be transformed into a representation of a copy number variation (e.g., a copy number variation), or a genetic variation, for example. Reads of a mixture of nucleic acids from multiples subjects can be transformed into a representation of a genome, or portion thereof, for each of the multiple subjects. In certain embodiments, "obtaining" nucleic acid sequence reads of a sample from a subject and/or "obtaining" nucleic acid sequence reads of a biological specimen (e.g., a sample) obtained from one or more subjects can involve directly sequencing nucleic acid to obtain the sequence information. In some embodiments, "obtaining" can involve receiving sequence information obtained directly from a nucleic acid by another. For example, in some embodiments, sequence information (e.g., sequencing reads) are provided or obtained in the form of an electronic file (e.g., a non-transitory computer-readable media).

In certain embodiments, sequence reads are obtained for an entire genome or for a portion of a genome. For example, targeted methods are known in which reads are obtained for a specific portion of a genome (e.g., a specific chromosome or for a specific family of genes). In some embodiments, sequence reads are obtained by a chromosome-targeted method. In some embodiments, sequence reads are obtained by a gene-targeted method that obtains reads from a family of related genes.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, each nucleotide of the genome is represented by one read on average. A genome also can be sequenced with redundancy, where a given region of the genome can be covered by two or more reads or overlapping reads (e.g., "fold" coverage greater than 1). In some embodiments, a genome is sequenced with about 1-fold to about 100,000-fold coverage, about 1-fold to about 50,000-fold coverage, about 1-fold to about 10,000-fold coverage, about 1-fold to about 5,000-fold coverage, about 10-fold to 10,000-fold coverage, about 50-fold to 10,000-fold coverage, about 100-fold to 10,000-fold coverage, or about 1000-fold to about 10,000-fold coverage. In certain embodiments a genome, or portion thereof (e.g., for targeted methods) is sequence with a coverage of at least 5-, at least 10-, at least 50-, at least 100-, at least 500-, at least 1000- or at least 2000-fold coverage.

Mapping Reads

In some embodiments, sequence reads are mapped. In some embodiments a suitable mapping method, process or algorithm is used. In certain embodiments modified mapping methods and processes are used herein. Certain aspects of mapping processes are described hereafter.

Mapping nucleotide sequence reads (e.g., sequence information from a fragment whose physical genomic position is unknown) can be performed in a number of ways, and often comprises alignment of the obtained sequence reads, or portions thereof, with a matching sequence in a reference genome. In such alignments, sequence reads generally are aligned to a reference sequence and those that align are designated as being "mapped", "a mapped sequence read" or "a mapped read".

As used herein, the terms "aligned", "alignment", or "aligning" refer to two or more nucleic acid sequences that can be identified as a match (e.g., 100% identity) or partial match. Methods of aligning nucleic acid sequences are known and any suitable alignment method can be used for a method, system, process, module or program described herein. Alignments can be performed manually (e.g., for small projects) or by a computer (e.g., a software, program, module, or algorithm), non-limiting examples of which include the Efficient Local Alignment of Nucleotide Data (ELAND) computer program distributed as part of the Illumina Genomics Analysis pipeline. Alignment of a sequence read can be a 100% sequence match (e.g., 100% identity). In some cases, an alignment is less than a 100% identity (e.g., non-perfect match, partial match, partial alignment). In some embodiments an acceptable alignment of two nucleic acids comprises at least a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% identity. Parameters and thresholds (e.g., a percent identity thresholds) for an acceptable alignment or match can be predetermined by a user, module or program. In some embodiments, an alignment comprises a mismatch (non-identical aligned nucleotides). In some embodiments, an alignment comprises 1, 2, 3, 4 5 or more mismatches. Two or more sequences can be aligned using either strand. In certain embodiments a nucleic acid sequence is aligned with the reverse complement of another nucleic acid sequence.

Various computational methods (e.g., computer implemented methods) can be used to map and/or align sequence reads to a reference genome. Sequence reads can be mapped by a mapping module or by a machine or computer comprising a mapping module (e.g., a suitable mapping and/or alignment program), which mapping module generally maps reads to a reference genome or segment thereof. Sequence reads and/or paired-end reads are often mapped to a reference genome by use of a suitable mapping and/or alignment program non-limiting examples of which include BWA (Li H. and Durbin R. (2009) *Bioinformatics* 25, 1754-60), Novoalign [Novocraft (2010)], Bowtie (Langmead B, et al., (2009) *Genome Biol.* 10:R25), SOAP2 (Li R, et al., (2009) *Bioinformatics* 25, 1966-67), BFAST (Homer N, et al., (2009) *PLoS ONE* 4, e7767), GASSST (Rizk, G. and Lavenier, D. (2010) *Bioinformatics* 26, 2534-2540), and MPscan (Rivals E., et al. (2009) *Lecture Notes in Computer Science* 5724, 246-260), or the like. Sequence reads and/or paired-end reads can be mapped and/or aligned using a suitable short read alignment program. Non-limiting examples of short read alignment programs are BarraCUDA, BFAST, BLASTN, BLAST, BLAT, BLITZ, Bowtie (e.g., BOWTIE 1, BOWTIE 2), BWA (Li H, D. R., Fast and accurate short read alignment with Burrows-Wheeler transform. (2009), *Bioinformatics*, 26 (5), 589-95), CASHX, CUDA-EC, CUSHAW, CUSHAW2, drFAST, FASTA, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, Novoalign3, NovoalignCS, Novocraft, NextGENe, Omixon, PALMapper, Partek, PASS, PerM, PROBEMATCH, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like, variations thereof or combinations thereof. A mapping module can map sequencing reads by a suitable method known in the art or described herein. In some embodiments, a mapping module or a machine or computer comprising a mapping module is required to provide mapped sequence reads. A mapping module often comprises a suitable mapping and/or alignment program or algorithm.

In some embodiments one or more sequence reads and/or information associated with a sequence read are stored on and/or accessed from a non-transitory computer-readable storage medium in a suitable computer-readable format. Information stored on a non-transitory computer-readable storage medium is sometimes referred to as a file or data file. Reads (e.g., individual reads, paired end reads, read mates, read mate pairs), selected reads, sets or subsets of reads and/or information associated with one or more reads is often stored in a suitable file or suitable data file. A file often comprises a suitable format. In some embodiments information associated with a sequence read includes information about individual reads, read mates and/or reads mapped to a reference genome. For example, a sequence read is sometimes stored in a format that includes information about or associated with one or more sequence reads, non-limiting examples of such information includes a complete or partial nucleic acid sequence, mappability, a mappability score, a mapped location, a relative location or distance from other mapped or unmapped reads (e.g., expected, estimated or average distance between read mates of paired-end sequence reads), orientation relative to a reference genome or to other reads (e.g., relative orientation to a read mate), an estimated or precise location of a read mates (e.g., according to mapped positions on a reference genome or according to a pile up), G/C content, the like or combinations thereof. Sequence reads (e.g., read mates) often comprise a known orientation. For example, a storage medium often comprises a file which contains a known orientation of read mates. In some embodiments an orientation of read mates and/or an estimated insert size is used to determine the position and/or mappability of a read mate pair. A "computer-readable format" is sometimes referred to generally herein as a format. In some embodiments sequence reads are stored and/or accessed in a suitable binary format, a text format, the like or a combination thereof. A binary format is sometimes a BAM format. A text format is sometimes a sequence alignment/map (SAM) format. Non-limiting examples of binary and/or text formats include BAM, sorted BAM, SAM, SRF, FASTA, FASTQ, Gzip, the like, or combinations thereof.

In some embodiments a program herein is configured to instruct a microprocessor to obtain or retrieve one or more files (e.g., sorted bam files). In some embodiments a program herein is configured to instruct a microprocessor to obtain or retrieve one or more FASTQ files (e.g., a FASTQ file for a first read and a second read) and/or one or more reference files (e.g., a FASTA or FASTQ file). In some embodiments a program herein instructs a microprocessor to call a module and/or transfers data and/or information (e.g., files) to or from one or more modules (e.g., a database, a sequencer, an aligner, a mapping module, and the like). In some embodiments a program instructs a processor to call a module which creates new files and formats for input into another processing step. In some embodiments sequence reads are in a compressed format requiring less storage space than an uncompressed format. The term "compressed" as used herein refers to a process of data compression, source coding, and/or bit-rate reduction where a computer readable data file is reduced in size. In certain embodiments, compressed files are uncompressed prior to use using a suitable method.

In some embodiments, a read may unambiguously or ambiguously map to a reference genome. A read is considered as "unambiguously mapped" if it aligns with a single sequence in the reference genome. A read is considered as "ambiguously mapped" if it aligns with two or more sequences in a reference genome. For example, a read that aligns with a gene of interest and a counterpart gene of the gene of interest of an unmodified reference genome is considered ambiguously mapped. In some embodiments, ambiguously mapped reads are eliminated from further analysis (e.g., quantification). A certain, small degree of mismatch (0-1, 0-2, 0-3, 0-10, or 0-20) may be allowed to account for genetic variations or nucleotide polymorphisms (e.g., SNPs or larger sequence variations) that may exist between the reference genome and the reads from individual samples being mapped, in certain embodiments. In some embodiments, no degree of mismatch is allowed for a read mapped to a reference sequence.

In certain embodiments, mappability of a read or read pair is assessed. Mappability is the ability to unambiguously map a nucleotide sequence read or read pair to a portion of a reference genome, typically up to a specified number of mismatches, including, for example, 0, 1, 2, 3, 4, 5, 6, 7, 8, 9, 10 or more mismatches. In some embodiments, mappability is provided as a score or value where the score or value is generated by a suitable mapping algorithm or computer mapping software. In certain embodiments, a mappability threshold can be pre-determined where reads with mappability above a threshold value are retained and reads with mappability below a mappability threshold are discarded, removed from consideration and/or removed from further analysis. High quality sequence reads aligned to genomic regions comprising stretches of unique nucleotide sequence sometimes have a high mappability value.

Paired-end reads are sometimes mapped to a reference genome. In some embodiments, information from both read mates of a read mate pair (e.g., orientation, estimated insert size, estimated distance between reads) is factored in the mapping process. A nucleic acid located between two paired-end reads is often referred to herein as an insert. In some embodiments insert size is determined or estimated by mapping both read mates of a read mate pair to a reference sequence. In some embodiments insert size (e.g., length) is estimated or determined according to a distribution. In certain embodiments the probability of an insert size comprising a viable insert is determined from the insert size distribution. In some embodiments insert size is determined by a suitable distribution and/or a suitable distribution function. Non-limiting examples of a distribution function include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. Insert size is sometimes generated from averaged, normalized and/or weighted insert lengths. Insert size distributions are sometimes estimated according to estimated and/or known nucleic acid fragment lengths derived from fragments of a nucleic acid library that was sequenced. In some embodiments a suitable storage medium comprises stored estimated insert lengths, insert length distributions and the like. In certain embodiments, sequence reads comprise an insert size distribution, estimated insert lengths, estimated distances between read mates, the like or combinations thereof. In certain embodiments, reads of a read mate pair are filtered according to an insert size distribution, estimated insert length, estimated distances between read mates, the like or combinations thereof.

In certain embodiments, reads are mapped to a modified reference genome with an expected ploidy. Ploidy often refers to the expected number of gene alleles that are present in a subjects genome, or in a portion of a subject genome. In certain embodiments, a ploidy is an expected number of alleles to which reads will map or align. For example, for reads obtained from a diploid subject, traditional methods of mapping expect a ploidy of 2 which indicates to an algorithm, module or program (e.g., an alignment program) that reads are expected to map to two alleles, which alleles may or may not be distinct. In certain embodiments herein, a ploidy is pre-determined according to the number of total alleles present in a gene of interest and its one or more counterpart genes. For example, for a diploid subject comprising a gene of interest and one counterpart gene of the gene of interest, a ploidy of 4 is used and/or assigned for a suitable mapping program, system, process or method using a modified reference genome with the counterpart genome substantially altered so that the counterpart gene sequence reads map to the gene of interest. In certain analogous embodiments where a diploid subject comprises a gene of interest and two counterpart genes of the gene of interest, a ploidy of 6 is used for and/or assigned to a suitable program, system, process or method, for example. In certain embodiments, a ploidy used for and/or assigned to a suitable program, system, process or method can be predetermined and/or input by an operator. In some embodiments a microprocessor is instructed to expect reads to map to 4, 6, 8, or 10 alleles of a gene of interest of a subject (e.g., a ploidy of 4, 6, 8, or 10 respectively) were reads obtained from the subject map to a gene of interest of a modified reference genome. In some embodiments a mapping module is instructed to expect reads to map to at least 4, 6, 8, or 10 alleles of a gene of interest of a subject (e.g., a ploidy of at least 4, 6, 8, or 10 respectively) were reads obtained from the subject map to a gene of interest of a modified reference genome. In some embodiments a microprocessor or mapping module is instructed to expect a ploidy of 4 for the gene of interest of the subject (e.g., where the subject is diploid). In some embodiments a microprocessor or mapping module is instructed to expect a ploidy of 4 for a gene of interest of the subject, where the subject is diploid, and the genome of the subject includes one counterpart gene of the gene of interest. In some embodiments a microprocessor or mapping module is instructed to expect a ploidy of 6 for the gene of interest of the subject (e.g., where the subject is diploid). In some embodiments a microprocessor or mapping module is instructed to expect a ploidy of 4 for a gene of interest of the subject, where the subject is diploid, and the genome of the subject includes two counterpart genes of the gene of interest. Thus, in some embodiments, for a diploid subject, a microprocessor or mapping module is instructed to expect a ploidy which is the sum of the number of counterpart genes and the gene of interest multiplied by 2. For example, in certain embodiments of a mapping process described herein, expected ploidy=2 (n+CPG) where n equals 1 and represents the gene of interest, and CPG is the number of counter part genes.

Reference Genomes

As used herein, the term "reference genome" can refer to any particular known, sequenced or characterized genome, whether partial or complete, of any organism or virus which may be used to reference identified sequences from a subject. Accordingly, in some embodiments, a reference genome comprises an assembly of nucleic acid sequences often in the form of a non-transitory computer-readable media. A reference can be a complete genome or a partial genome. A reference genome sometimes refers to a segment or portion of a reference genome (e.g., a chromosome or part thereof, e.g., one or more portions of a reference genome). In some embodiments a reference genome comprises a gene of interest and one or more counterpart genes of the gene of interest. In some embodiments, a reference genome comprises nucleic acid sequences of a gene of interest and nucleic acid sequences of one or more counterpart genes of the gene of interest. Any suitable reference genome can be modified and used for a method, process, system or program herein. Human genomes, human genome assemblies and/or genomes from any other organisms can be used as a reference genome. One or more human genomes, human genome assemblies as well as genomes of other organisms can be found online at the National Center for Biotechnology Information at http://www.ncbi.nlm.nih.gov/. In some embodiments a reference genome is the human genome reference sequence version GRCh37 (Church D M, S. V. (2011) PLoS Biol, 9 (7)), for example. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes. The term "reference sequence" as used herein refers to one or more polynucleotide sequences of one or more reference samples. In some embodiments reference sequences comprise sequence reads obtained from a reference sample. In some embodiments reference sequences comprise sequence reads, an assembly of reads, and/or a consensus DNA sequence (e.g., a sequence contig). In some embodiments a reference sample is obtained from a reference subject substantially free of a genetic variation (e.g., a genetic variation in question). In some embodiments a reference sample is obtained from a reference subject comprising a known genetic variation. The term "reference" as used herein can refer to a reference genome, a reference sequence, reference sample and/or a reference subject. In some embodiments, sequence reads can be mapped and/or aligned with sequences in nucleic acid databases known in the art including, for example, Gen- Bank, dbEST, dbSTS, EMBL (European Molecular Biology Laboratory) and DDBJ (DNA Databank of Japan). BLAST or similar tools can be used to search the identified sequences against a sequence database.

Modified Reference Genome

In some embodiments a reference genome is modified thereby providing a modified reference genome. In certain embodiments reads are mapped to a modified reference genome. In some embodiments a reference genome is modified wherein one or more counterpart genes of the reference genome are substantially altered. A substantially altered counterpart gene often refers to the counterpart gene of a modified reference genome where the substantially altered counterpart gene is modified such that a sequence read derived from the same counterpart gene of a subject will not substantially align to the substantially altered counterpart gene. An alignment pairing of a nucleotide, or an ambiguous nucleotide marker of a read to another ambiguous nucleotide marker of a reference sequence is often not given any weight of confidence. In certain embodiments, a read that maps or aligns to an unmodified counterpart gene of a reference genome cannot map or substantially align (e.g., within a predetermined threshold of confidence) to the same counterpart gene after it has been substantially altered (e.g., the substantially altered counterpart gene). In some embodiments, a modified reference genome comprises a gene of interest and one or more counterpart genes of the gene of interest wherein the one or more counterpart genes, or portions thereof, are substantially altered. Therefore, a modified reference genome often comprises a nucleic acid sequence of a gene of interest and a nucleic acid sequence of one or more counterpart genes of the gene of interest, where the nucleic acid sequence of the one or more counterpart genes, or portions thereof, are substantially altered. In some embodiments, a modified reference genome comprises a gene of interest and one or more counterpart genes of the gene of interest wherein the one or more counterpart genes are substantially altered, and the remaining portion of the reference genome is not modified. In certain embodiments, a gene of interest is not modified, altered, substantially altered or deleted. A substantially altered counterpart gene often comprises one or more nucleotide deletions, insertions, and/or substitutions. In some embodiments a counterpart gene is substantially altered by deleting portions of the gene or by deleting all of the gene. In some embodiments a counterpart gene is substantially altered by replacing one or more, substantially all, or all, of the nucleotides of the counterpart gene with different nucleotides or placeholder ambiguous nucleotide markers (e.g., replacing the As, Gs, Ts and Cs of the counterpart gene sequence with a placeholder label such as Ns) so that sequence reads from the counterpart gene will no longer map or align with the counterpart gene in the modified reference genome. In certain embodiments at least 20%, at least 30%, at least 40%, at least 50%, at least 60% at least 70%, at least 80%, at least 90% or at least 95% of a counterpart gene is deleted. In certain embodiments at least 20%, at least 30%, at least 40%, at least 50%, at least 60% at least 70%, at least 80%, at least 90% or at least 95% of the nucleotides of a counterpart gene are substituted with different nucleotides. In certain embodiments at least 20%, at least 30%, at least 40%, at least 50%, at least 60% at least 70%, at least 80%, at least 90% or at least 95%, or all of the nucleotides of a counterpart gene are substituted with ambiguous nucleotide markers. An ambiguous nucleotide marker is a nucleotide symbol that represents two or more different nucleotides. Ambiguous nucleotide markers are often recognized by a suitable mapping or alignment program as an ambiguous marker. Non-limiting examples of ambiguous nucleotide markers include N (which represents any nucleotide), R (which represents A or G), Y (which represents C or T), S (which represents G or C), W (which represents A or T), K (which represents G or T), M (which represents A or C), B (which represents C, G or T), D (which represents A, G or T), H (which represents A, C or T), V (which represents A, C or G), "." (which represents a gap), "-" (which represents a gap), the like or combinations thereof. Any suitable ambiguous nucleotide marker can be used to disrupt a counterpart gene. In some embodiments a counterpart gene is substantially altered by inserting one or more nucleotides into the counterpart gene.

In some embodiments one or more counterpart genes or a gene of interest are substantially altered by a method described herein, such that reads derived from the one or more counterpart genes of a subject will unambiguously map to the gene of interest in a modified reference genome. In certain embodiments, reads derived from a counterpart gene of a subject cannot map or align to the counterpart gene in a modified reference genome where the counterpart gene is substantially altered. Thus, in some embodiments, such reads that ambiguously map to a gene of interest and its counterpart gene of an unmodified reference genome will often map unambiguously to the gene of interest of a modified reference genome. In certain embodiments such reads that ambiguously map to a gene of interest and its counterpart gene of an unmodified reference genome will often map unambiguously to the gene of interest of a modified reference genome when a mapping system, method, program or process expects a ploidy of 4 or more. The expected ploidy value depends, in part, on the number of substantially altered counterpart genes in the modified reference genome.

Read Filtering

In some embodiments a method, program, process or system herein comprises a read filtering process. Any suitable read filtering process can be utilized for a process, system or method described herein. A read filtering process is often carried out by a mapping module or a read filtering module. In certain embodiments a mapping system, program or process comprises a suitable read filtering process. In certain embodiments a read filtering process comprises selecting and/or removing sequence reads as described herein. In some embodiments a read filtering process comprises a method of selecting a subset of reads from a plurality of reads by removing certain reads according to predetermined filtering parameters, non-limiting examples of which include mappability, alignment to a reference genome, discordancy, and the like. A filtering process often removes certain reads or read pairs from an analysis, system or process so that the removed reads, removed read pairs and/or information associated with such reads is not considered when determining the presence or absence of a genetic variation, or likelihood thereof.

For example, in some embodiments a read is filtered and/or removed when the read is mapped incorrectly or ambiguously to a reference genome, fails to map to the reference genome or comprises a low mappability score (e.g., below a predetermined threshold). In some embodiments one or both read mate pairs are removed from an analysis or mapping process when one read mate of a read mate pair (e.g., obtained from a paired-end sequencing approach) maps to a reference genome and the other read mate of the read mate pair is mapped incorrectly or ambiguously to the reference genome, fails to map to the reference genome or comprises a low mappability score (e.g., below a predetermined threshold). Such a read mate pair is sometimes referred to as a discordant read mate pair. In some embodiments a discordant read mate pair comprises one read mate that maps to a region of a reference genome of interest (e.g., a genomic regions of interest) and the other read mate fails to map to the reference genome of interest or fails to map with the same region of a reference genome. In some embodiments a discordant read mate pair comprises a first read mate that maps to a portion of a reference genome of interest (e.g., a portion of a genomic region of interest) and a second read mate that maps to an unexpected location of a reference genome. Non-limiting examples of an unexpected location of a reference genome include (i) a different chromosome than the chromosome to which the first read mapped, (ii) a genomic location separated from the first read mate by more than a predetermined distance, non-limiting examples of which include a distance predicted from an estimated insert size; a distance of more than 300 bp, more than 500 bp, more than 1000 bp, more than 5000 bp, or more than 10,000 bp and (iii) an orientation inconsistent with the first read (e.g., opposite orientations), the like or a combination thereof. In some embodiments a discordant read mate pair comprises a first read mate that maps to a first segment of a reference genome, or a portion thereof, and a second read mate that is unmappable and/or comprises low mappability (e.g., a low mappability score). In some embodiments a discordant read mate pair comprises a first read mate that maps to a reference genome and the mappability of the second read mate is not determined. Discordant read mate pairs can be identified by a suitable discordant read identifying module, program, method or process. Non-limiting examples of discordant read identifying programs and modules include SVDetect, Lumpy, BreakDancer, BreakDancerMax, CREST, DELLY, the like or combinations thereof. In certain embodiments discordant read pairs are identified by a suitable algorithm that identifies a paired-end read, where one read mate maps to a reference genome and the other read mate maps incorrectly to the reference genome, fails to map to the reference genome or comprises a low mappability score.

In some embodiments, sequence reads are trimmed. In certain embodiments trimming refers to identification and/or removal of synthetic and/or heterologous nucleic acids, or portions of nucleic acids from sequence reads, which synthetic and/or heterologous nucleic acids were used in construction of a library and/or for a sequencing method. Heterologous nucleic acids are often heterologous or foreign to a subjects genome. Non-limiting examples of synthetic and/or heterologous nucleic acids that are often trimmed include adapters, plasmids, vectors, primer binding sites, index tags (e.g., nucleic acid barcodes sequences), nucleic acid capture sequences, the like or combinations thereof. In some embodiments trimming comprises instructing a processor to delete and/or ignore those portions of sequencing reads that are synthetic and/or heterologous. Synthetic nucleic acids, heterologous nucleic acids and/or trimmed nucleic acids are often not included in method or process herein. In some embodiments sequence reads are trimmed prior to, or during, obtaining a set of paired-end sequence reads. In some embodiments sequence reads are trimmed prior to, or during, determining a pile-up, filtering, constructing one or more contigs, assembling one or more supercontigs and/or generating a genotype likelihood ratio. In certain embodiments trimming is performed by a trimming module.

In some embodiments some or all reads are realigned and/or re-mapped to gene of interest, or a portion thereof. In some embodiments reads are realigned and/or re-mapped after a filtering step where some reads are removed from the analysis. In some embodiments reads are realigned and/or re-mapped locally to a gene of interest (e.g., a local alignment). For example, after initial mapping or alignment and filtering the mapped/aligned reads are locally realigned in regions of the gene of interest suspected of comprising a genetic variation. In certain embodiments this method maximizes the statistical power for calling an outcome. In some embodiment reads are realigned and an outcome is determined according to a method described in McKenna (e.g., McKenna A, H. M. (2010), Genome Res, 20 (9), 1297-303, which is incorporated herein by reference in its entirety).

Pile-Up

In some embodiments a method or process herein comprises determining a pile-up for a set or subset of sequence reads. In some embodiments a pile-up comprises one or more overlaps (e.g., a plurality of overlaps) between a plurality of reads of a set wherein some of the reads map to a gene of interest of a modified reference genome. In some embodiments a pile-up comprises constructing a tiling graph. In certain embodiments determining the presence or absence of a genetic variation or the likelihood of the presence or absence of a genetic variation in a gene of interest comprises determining one or more pile-up. Any suitable method of determining a pile-up (e.g., a pile-up) can be used for a method, process, program or system herein. In certain embodiments, a pile-up is constructed for each expected allele of a gene of interest.

Outcomes

In certain embodiments an outcome is determined by a method, process, system or program described herein. An outcome is sometimes a determination of the presence or absence of one or more genetic variations in a gene of interest. In some embodiments an outcome is a determination of the likelihood of the presence or absence of one or more genetic variations in a gene of interest.

An outcome is often determined according to reads obtained from a subject (e.g., a sample obtained from a subject) that are mapped and/or aligned to a gene of interest in a modified reference genome. In some embodiments an outcome is determined according to a local alignment where reads obtained from a subject (e.g., a sample obtained from a subject) are re-mapped and/or re-aligned to a gene of interest. In some embodiments, an outcome is determined according to a pile-up of reads obtained from a subject (e.g., a sample obtained from a subject) that reads of the pile-up are mapped and/or aligned to a gene of interest in a modified reference genome. In certain embodiments where the location of a suspected genetic variation (e.g., a polymorphism) in a gene of interest is known, determining an outcome may comprise obtaining sequence reads, mapping reads, aligning reads, analyzing reads, and/or performing a pile-up, where such processes are applied to an entire gene, or portions thereof that include a gene of interest.

An outcome module often carries out an outcome process (e.g., a determination). In certain embodiments, an outcome process generates all possible alleles for an expected ploidy. In some embodiments all possible alleles for an expected ploidy are determined by an outcome module.

An outcome can be determined by a suitable caller or method, non-limiting examples of which include the Unified Genotyper algorithm from the Genome Analysis Toolkit (DePristo M A, B. E. (2011) Nat Genet., 43 (5), 491-8); FreeBayes (v0.9.6 to v0.8.14), a custom evidence-based caller for complex repetitive loci; and CNVitae, a custom CNV caller, the like or combinations thereof.

In some embodiments the likelihood of the presence or absence of genetic variation in a gene of interest of a subject is determined. A likelihood is often a mathematical probability. In some embodiments a likelihood of a genotype is determined. A likelihood can be determined by a suitable mathematical method. In some embodiments determining a likelihood comprises a screening process where sequence reads obtained from a set of subjects are mapped to a modified reference genome as described herein and a subset of subjects are removed from the analysis. In some embodiments sequence reads obtained from a set of subjects are mapped to a modified reference genome by a method described herein, the absence of a genetic variation is determined for a subset of the subjects, which subset of subjects is removed from further analysis, and the remaining subjects are determined to have a likelihood of the presence of a genetic variation. In some embodiments, reads obtained from a subject that map and/or align to a gene of interest of a modified reference genome with 0 mismatch indicate the absence of a genetic variation in the subject. In some embodiments, reads obtained from a subject that map and/or align to an exon of a gene of interest of a modified reference genome with 0 mismatch indicate the absence of a genetic variation in the subject. In some embodiments, reads obtained from a subject that map and/or align to a regulatory region of a gene of interest of a modified reference genome with 0 mismatch indicate the absence of a genetic variation in the subject. In some embodiments, reads obtained from a subject that map and/or align to a gene of interest of a modified reference genome with 1, 2, 3, 4, 5 or more mismatches, indicate the likelihood of the presence of a genetic variation in the subject. Where a likelihood of the presence of a genetic variation in a gene of interest of a subject is determined, a sample obtained from the subject (e.g., a sample comprising nucleic acid) can be further analyzed to determined the presence or absence of the genetic variation in the gene of interest. Nucleic acid from a subject can be further analyzed using a suitable method, non-limiting examples of which include targeted amplification (e.g., PCR, LR-PCR) of a gene of interest, or a portion thereof, followed by sequencing the gene of interest, or a portion thereof thought to contain the genetic variation. Any suitable method of sequencing can be used to further analyze a gene of interest. In certain embodiments, the presence or absence of a genetic variation in a gene of interest, in a subject determined to have a likelihood of having a genetic variation, is determined by sequencing the gene of interest or a portion thereof.

In some embodiments a likelihood of the presence or absence of a genetic variation is defined by a confidence level of about 90% or greater, 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. In some embodiments the presence of a genetic variation in a gene of interested is determined where the likelihood of the presence of a genetic variation is determined with a confidence level of about 99% or greater, about 99.1% or greater, about 99.2% or greater, about 99.3% or greater, about 99.4% or greater, about 99.5% or greater, about 99.6% or greater, about 99.7% or greater, about 99.8% or greater or about 99.9% or greater. For example, in some embodiments, the likelihood of the presence of a genetic variation in a gene of interest in a subject is determined with a confidence level of at least 99.9%. In some embodiments, a likelihood of the presence or absence of a genetic variation in a gene of interest is determined with a confidence interval (CI) of about 80% to about 100%. For example, the confidence interval (CI) can be at least about 81%, 82%, 83%, 84%, 85%, 86%, 87%, 88%, 89%, 90%, 91%, 92%, 93%, 94%, 95%, 96%, 97%, 98%, or at least 99%. A confidence level and/or a confidence interval can be determined by any suitable method, or mathematical process.

In some embodiments a likelihood of the presence or absence of a genetic variation in a gene of interest is determined with an accuracy of at least about 90% to about 100%. For example, likelihood of the presence or absence of a genetic variation in a gene of interest may be determined with an accuracy of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. An accuracy can be determined by any suitable method, or mathematical process.

In some embodiments a likelihood of the presence or absence of a genetic variation in a gene of interest is determined with a precision of at least about 90% to about 100%. For example, likelihood of the presence or absence of a genetic variation in a gene of interest may be determined with a precision of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. In some embodiments, a likelihood of the presence or absence of a genetic variation in a gene of interest is determined with a precision of about 80% to about 100%. A precision can be determined by any suitable method, or mathematical process.

In some embodiments a likelihood of the presence or absence of a genetic variation in a gene of interest is determined with a sensitivity (e.g., an analytical sensitivity) of at least about 90% to about 100%. For example, likelihood of the presence or absence of a genetic variation in a gene of interest may be determined with a sensitivity of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. In some embodiments, a likelihood of the presence or absence of a genetic variation in a gene of interest is determined with a sensitivity of about 80% to about 100%. A sensitivity (e.g., an analytical sensitivity) can be determined by any suitable method, or mathematical process.

In some embodiments a likelihood of the presence or absence of a genetic variation in a gene of interest is determined with a specificity (e.g., analytical specificity) of at least about 90% to about 100%. For example, likelihood of the presence or absence of a genetic variation in a gene of interest may be determined with a specificity of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. In some embodiments, a likelihood of the presence or absence of a genetic variation in a gene of interest is determined with a specificity of about 80% to about 100%. A specificity (e.g., an analytical specificity) can be determined by any suitable method, or mathematical process.

Non-limiting specific examples of generating outcomes and associated confidence levels, accuracy, precision, sensitivity and specificity are provided in the Examples section herein.

In some embodiments, an outcome comprises a value above or below a predetermined threshold or cutoff value (e.g., greater than 1, less than 1), and an uncertainty or confidence level associated with the value. In certain embodiments a predetermined threshold or cutoff value is an expected level or an expected level range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot). In some embodiments an outcome can be determined from a graphically representation.

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. In some embodiments, at least two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative.

Systems, Machines, Storage Mediums and Interfaces

Certain processes and methods described herein often cannot be performed without a computer, microprocessor, software, module or other machine. Methods described herein typically are computer-implemented methods, and one or more portions of a method sometimes are performed by one or more processors (e.g., microprocessors), computers, or microprocessor controlled machines. Embodiments pertaining to methods described in this document generally are applicable to the same or related processes implemented by instructions in systems, machines and computer program products described herein. Embodiments pertaining to methods described in this document generally can be applicable to the same or related processes implemented by a non-transitory computer-readable storage medium with an executable program stored thereon, where the program instructs a microprocessor to perform the method, or a part thereof. The descriptive term "non-transitory" as used herein is expressly limiting and excludes transitory, propagating signals (e.g., transmission signals, electronic transmissions, waves (e.g., carrier waves)). The terms "non-transitory computer-readable media" and/or "non-transitory computer-readable medium" as used herein comprise all computer-readable mediums except for transitory, propagating signals. In some embodiments, processes and methods described herein are performed by automated methods. In some embodiments one or more steps and a method described herein is carried out by a microprocessor and/or computer, and/or carried out in conjunction with memory. In some embodiments, an automated method is embodied in software, modules, microprocessors, peripherals and/or a machine comprising the like, that (i) obtain a set of paired-end sequence reads comprising a plurality of read mate pairs, each pair comprising two read mates, wherein at least one of the two read mates of each pair is mapped to at least one portion of a reference genome comprising a pre-selected genomic region of interest and wherein some of the paired-end sequence reads are not mapped to the at least one portion of the reference genome, (ii) determine a pile-up for a set of sequence reads, (iii) construct one or more contigs according to a pile-up, (iv) assemble one or more supercontigs, (v) generate a genotype likelihood ratio, (vi) determine the presence or absence of genetic variation, or (vii) perform a combination thereof.

Machines, software and interfaces may be used to conduct methods described herein. Using machines, software and interfaces, a user may enter, request, query or determine options for using particular information, programs or processes (e.g., obtaining reads, recruiting reads, mapping reads, generating a pile-up, constructing contigs, assembling haplotypes, generating a genotype likelihood ratio, determining the presence or absence of genetic variation, the like or a combination thereof), which can involve implementing statistical analysis algorithms, statistical significance algorithms, statistical error algorithms, statistical probability algorithms, iterative steps, validation algorithms, and graphical representations, for example. In some embodiments, a data file may be entered by a user as input information, a user may download one or more data files by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding one or more genotype likelihood ratios).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations. Where a system includes two or more machines, some or all of the machines may be located at the same location as a user, some or all of the machines may be located at a location different than a user, all of the machines may be located at the same location as the user, and/or all of the machine may be located at one or more locations different than the user.

A system sometimes comprises a computing apparatus or a sequencing apparatus, or a computing apparatus and a sequencing apparatus (i.e., sequencing machine and/or computing machine). Apparatus, as referred to herein, is sometimes a machine. A sequencing apparatus generally is configured to receive physical nucleic acid and generate signals corresponding to nucleotide bases of the nucleic acid. A sequencing apparatus is often "loaded" with a sample comprising nucleic acid and the nucleic acid of the sample loaded in the sequencing apparatus generally is subjected to a nucleic acid sequencing process. The term "loading a sequence apparatus" as used herein refers to contacting a portion of a sequencing apparatus (e.g., a flow cell) with a nucleic acid sample, which portion of the sequencing apparatus is configured to receive a sample for conducting a nucleic acid sequencing process. In some embodiments a sequencing apparatus is loaded with a variant of a sample nucleic acid. A variant sometimes is produced by a process that modifies the sample nucleic acid to a form suitable for sequencing the nucleic acid (e.g., by ligation; e.g., adding adaptors to ends of sample nucleic acid by ligation, amplification, restriction digest, the like or combinations thereof). A sequencing apparatus is often configured, in part, to perform a suitable DNA sequencing method that generates signals (e.g., electronic signals, detector signals, data files, images, the like, or combinations thereof) corresponding to nucleotide bases of the loaded nucleic acid.

One or more signals corresponding to each base of a DNA sequence are often processed and/or transformed into base calls (e.g., a specific nucleotide base, e.g., guanine, cytosine, thymine, uracil, adenine, and the like) by a suitable process. A collection of base calls derived from a loaded nucleic acid often are processed and/or assembled into one or more sequence reads. In embodiments in which multiple sample nucleic acids are sequenced at one time (i.e., multiplexing), a suitable de-multiplexing process can be utilized to associated particular reads with the sample nucleic acid from which they originated. Sequence reads can be aligned by a suitable process to a reference genome and reads aligned to portions of the reference genome, and read mates that may not be aligned with a reference genome (e.g., read mates with low mappability scores or reads mates that are unmappable) can be stored, filtered and/or processed as described herein.

A sequencing apparatus sometimes is associated with and/or comprises one or more computing apparatus in a system. The one or more computing apparatus sometimes are configured to perform one or more of the following processes: obtain reads, map reads, filter reads, determine a pile-up for a set of sequence reads, determine the presence or absence of a genetic variation, determine the likelihood of the presence or absence of a genetic variation, determine an outcome, the like, or a combination thereof. The one or more computing apparatus sometimes are configured to perform one or more of the following additional processes: generate base calls from sequencing apparatus signals, generate reads, trim reads, de-multiplexing reads, and the like.

In some embodiments, a method or process is performed by multiple computing apparatus and a subset of the total processes performed by the system may be allocated to or divided among particular computing apparatus in the system. Subsets of the total number of processes can be divided among two or more computing apparatus, or groups thereof, in any suitable combination. A multi-computing apparatus system sometimes includes one or more suitable servers local to a sequencing apparatus, and sometimes includes one or more suitable servers not local to the sequencing apparatus (e.g., web servers, on-line servers, application servers, remote file servers, cloud servers (e.g., cloud environment, cloud computing)).

Apparatus in different system configurations can generate different types of output data. For example, a sequencing apparatus can output base signals and the base signal output data can be transferred to a computing apparatus that converts the base signal data to base calls. In some embodiments, the base calls are output data from one computing apparatus and are transferred to another computing apparatus for generating sequence reads. In certain embodiments, base calls are not output data from a particular apparatus, and instead, are utilized in the same apparatus that received sequencing apparatus base signals to generate sequence reads. In some embodiments, one apparatus receives sequencing apparatus base signals, generates base calls, sequence reads and de-multiplexes sequence reads, and outputs de-multiplexed sequence reads for a sample that can be transferred to another apparatus or group thereof that aligns the sequence reads to a reference genome. Output data from one apparatus can be transferred to a second apparatus in any suitable manner. For example, output data from one apparatus sometimes is placed on a physical storage device and the storage device is transported and connected to a second apparatus to which the output data is transferred. Output data sometimes is stored by one apparatus in a database, and a second apparatus accesses the output data from the same database.

In some embodiments a user interacts with an apparatus (e.g., a computing apparatus, a sequencing apparatus). A user may, for example, place a query to software which then may acquire a data set via internet access, and in certain embodiments, a programmable microprocessor may be prompted to acquire a suitable data set based on given parameters. A programmable microprocessor also may prompt a user to select one or more data set options selected by the microprocessor based on given parameters. A programmable microprocessor may prompt a user to select one or more data set options selected by the microprocessor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, machines, apparatuses (multiple apparatuses, also referred to herein in plural as apparatus), computer programs or a non-transitory computer-readable storage medium with an executable program stored thereon.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display (e.g., CRT, LED or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (Ethernet/Wi-Fi), a communication port (e.g., a USB port, HDMI port), Bluetooth, a PCMCIA slot and/or card, and the like. Data may be input by a suitable communication interface, device and/or method, including, but not limited to, manual input devices and/or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In certain embodiments, simulated data is generated by an in silico process and the simulated data serves as data that can be input via an input device. The term "in silico" refers to data (e.g., reads, aligned reads, mapped reads, pile-ups and the like), and/or a manipulation or a transformation of data that is performed using a computer, one or more modules, or a combination thereof. In certain embodiments methods and processes herein are performed in silico. In silico processes include, but are not limited to, mapping reads, aligning reads, overlapping reads, generating a pile-up, and generating outcomes.

A system may include software useful for performing a process described herein, and software can include one or more modules for performing such processes. The term "software" refers to computer-readable storage medium comprising program instructions (e.g., an executable program) that, when executed by a computer, perform computer operations. Instructions executable by the one or more microprocessors sometimes are provided as executable code, that when executed, can cause one or more microprocessors to implement a method described herein.

A module described herein can exist as software, and/or instructions (e.g., processes, routines, subroutines) embodied in the software which can be implemented or performed by a microprocessor. For example, a module can be a part of a program that performs a particular process or task. The term "module" refers to a self-contained functional unit that can be used in a larger machine or software system. A module can comprise a set of instructions for carrying out a function of the module by one or more microprocessors. Instructions of a module can be implemented in a computing environment by use of a suitable programming language, suitable software, and/or code written in a suitable language (e.g., a computer programming language known in the art) and/or operating system, non-limiting examples of which include UNIX, Linux, oracle, windows, Ubuntu, ActionScript, C, C++, C#, Haskell, Java, JavaScript, Objective-C, Perl, Python, Ruby, Smalltalk, SQL, Visual Basic, COBOL, Fortran, UML, HTML (e.g., with PHP), PGP, G, R, S, the like or combinations thereof.

In some embodiments a module comprises one or more data files and can transfer data files to another module and/or receive data files from another module. In some embodiments a module transforms data and/or information, for example, into tangible printed matter, instructions to a user, an alignment, an outcome, a display, a genotype, the like or combinations thereof. For example, one or more modules and/or microprocessors (e.g., apparatus or machines) described herein can obtain sequencing reads, which represent random, unordered, nucleic acid fragments of a subjects genome, and transform those reads into an accurate representation (e.g., a display) of a specific portion of subject's body (e.g., a portion of a subject's genome (e.g., a genotype of a genomic region of interest)). The process can be compared to a process of transforming millions of pieces of a puzzle into a picture or transforming bits of X-ray data into a display of a portion of a subjects body (e.g., a display of bones, organs, and other body tissues).

One or more modules can be utilized in a method described herein, non-limiting examples of which include a sequence module, a mapping module, a pile-up module, a filter module, an outcome module, the like or combination thereof. Modules are sometimes controlled by a microprocessor. In certain embodiments a module or a machine comprising one or more modules, gather, assemble, receive, obtain, access, recover provide and/or transfer data and/or information to or from another module, machine, component, peripheral or operator of a machine. In some embodiments, data and/or information (e.g., reads) are provided to a module by a machine comprising one or more of the following: one or more flow cells, a camera, a detector (e.g., a photo detector, a photo cell, an electrical detector (e.g., an amplitude modulation detector, a frequency and phase modulation detector, a phase-locked loop detector), a counter, a sensor (e.g., a sensor of pressure, temperature, volume, flow, weight), a fluid handling device, a data input device (e.g., a keyboard, mouse, scanner, voice recognition software and a microphone, stylus, or the like), a printer, a display (e.g., an LED, LCD, LCT or CRT), the like or combinations thereof. For example, sometimes an operator of a machine or apparatus provides a constant, a threshold value, a formula or a predetermined value to a module. A module is often configured to transfer data and/or information to or from a microprocessor, a storage medium and/or memory. A module is often configured to transfer data and/or information to, or receive data and/or information from another suitable module or machine. A module can manipulate and/or transform data and/or information. Data and/or information derived from or transformed by a module can be transferred to another suitable machine and/or module. A machine comprising a module can comprise at least one microprocessor. A machine comprising a module can include a microprocessor (e.g., one or more microprocessors) which microprocessor can perform and/or implement one or more instructions (e.g., processes, routines and/or subroutines) of a module. In some embodiments, a module operates with one or more external microprocessors (e.g., an internal or external network, server, storage device and/or storage network (e.g., a cloud)).

Data and/or information can be in a suitable form. For example, data and/or information can be digital or analogue. In certain embodiments, data and/or information sometimes can be packets, bytes, characters, or bits. In some embodiments, data and/or information can be any gathered, assembled or usable data or information. Non-limiting examples of data and/or information include a suitable media, pictures, video, sound (e.g., frequencies, audible or non-audible), numbers, constants, data files, a value, objects, time, functions, instructions, maps, references, sequences, reads, mapped reads, levels, ranges, thresholds, signals, displays, representations, or transformations thereof. A module can accept or receive data and/or information, transform the data and/or information into a second form, and provide or transfer the second form to an machine, peripheral, component or another module. A microprocessor can, in certain embodiments, carry out the instructions in a module. In some embodiments, one or more microprocessors are required to carry out instructions in a module or group of modules. A module can provide data and/or information to another module, machine or source and can receive data and/or information from another module, machine or source.

A computer program product sometimes is embodied on a non-transitory computer-readable medium, and sometimes is tangibly embodied on a non-transitory computer-readable medium. In certain embodiments a computer-readable storage medium comprises an executable program stored thereon. A module sometimes is stored on a non-transitory computer readable medium (e.g., disk, drive) or in memory (e.g., random access memory). A module and microprocessor capable of implementing instructions from a module can be located in a machine or in a different machine. A module and/or microprocessor capable of implementing an instruction for a module can be located in the same location as a user (e.g., local network) or in a different location from a user (e.g., remote network, cloud system). In embodiments in which a method is carried out in conjunction with two or more modules, the modules can be located in the same machine, one or more modules can be located in different machine in the same physical location, and one or more modules may be located in different machines in different physical locations.

In certain embodiments, a machine, apparatus or computer comprises one or more peripherals and/or components. Peripherals and/or components can transfer data and/or information to and from modules, peripherals and/or components. In certain embodiments a machine interacts with a peripheral and/or component that provides data and/or information. In certain embodiments peripherals and components assist a machine in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a microprocessor, a server, CDs, DVDs, graphic cards, specialized I/O devices (e.g., sequencers, photo cells, photo multiplier tubes, optical readers, sensors, etc.), network interface controllers, read-only memory (ROM), random-access memory (RAM), wireless transfer devices (Bluetooth devices, W-Fi devices, and the like), the world wide web (www), the internet, a computer and/or another module.

Modules and Computer Implementation

In some embodiments a system comprises a sequence module that is configured to generate sequence reads. A sequence module may comprise a nucleic acid sequencer (e.g., a machine or apparatus designed and configured to generate sequence reads for a nucleic acid library) and/or software and instructions configured to generate, organize, associate and/or trim sequence reads. A sequence module often provides sequence reads in the form of a data file (e.g., a bam file, a fasta file, and the like). A sequence module can provide sequence reads in any suitable file format. In certain embodiments, sequence reads are transferred from a sequence module to a mapping module.

In some embodiments a system comprises a mapping module. In some embodiments a mapping module is configured to map reads to a modified reference genome. In some embodiments a mapping module is configured to map or align reads to a gene of interest of a modified reference genome as described herein. In some embodiments a mapping module is configured to filter reads. In some embodiments a mapping module comprises a filter module which is configured to filter reads. In some embodiments a mapping module re-aligns or re-maps reads (e.g., filtered reads) to a gene of interest. In some embodiments a mapping module performs a local alignment by aligning filtered reads to a gene of interest, or a portion thereof. In some embodiments a mapping module performs a pile-up function. In certain embodiments, a mapping module comprises a pile-up module, which performs a pile-up function while aligning reads to a reference sequence. In certain embodiments, a mapping module receives reads from a sequence module. In some embodiments sequence reads are provided to a mapping module by a user and/or from a suitable data storage device. In certain embodiments, a mapping module transfers data and/or information (e.g., mapped, filtered and/or aligned reads) to an outcome module. In certain embodiments, a mapping module transfers data and/or information (e.g., mapped, filtered and/or aligned reads) to a pile-up module.

In some embodiments a pile-up module is configured to perform alignments and generate overlaps of reads (e.g., mapped reads). In some embodiments a pile-up module is configured to generate one or more pile-ups for a set of reads and a given gene of interest. A pile-up module often obtains and/or receives reads from a sequencing module, mapping module or a filter module and generates one or more pile-ups according to some or all of the reads received. In certain embodiments a pile-up module filters, removes and/or prunes overlaps. In certain embodiments a pile-up module selects and/or stores overlaps. In some embodiments a pile-up module generates a pile-up graph and/or tiling chart. A pile-up module often transfers selected overlaps and/or read-read alignments for a set of reads to an outcome module.

In some embodiments a system comprises an outcome module. In certain embodiments an outcome module receives data and/or information (e.g., data files) from a mapping module or a pile-up module. In certain embodiments an outcome module determines an outcome. Often an outcome is provided by an outcome module. An outcome sometimes is provided to a health care professional (e.g., laboratory technician or manager; physician or assistant) from an outcome module. An outcome module may comprise a suitable mathematical and/or statistical software package. In certain embodiments an outcome module generates a plot, table, chart or graph. In some embodiments an outcome module generates and/or compares standard statistical scores (e.g., Z-scores). The presence or absence of a genetic variation and/or associated medical condition (e.g., an outcome) is often determined by and/or provided by an outcome module. The likelihood of the presence or absence of a genetic variation and/or associated medical condition (e.g., an outcome) is often determined by and/or provided by an outcome module. In certain embodiments, the absence of a genetic variation in a gene of interest is determined for a subset of subjects by an outcome module. In certain embodiments, the likelihood of the presence of a genetic variation in a gene of interest is determined for a subset of subjects by an outcome module. The presence or absence of a genetic variation in a subject is, in some embodiments, identified by a machine comprising an outcome module. An outcome module can be specialized for determining a specific genetic variation (e.g., an STR, translocation, polymorphism, insertion, deletion). For example, an outcome module that identifies an STR can be different than and/or distinct from an outcome module that identifies a single nucleotide polymorphism. In some embodiments, an outcome module or a machine comprising an outcome module is required to identify a genetic variation or an outcome determinative of a genetic variation by re-aligning sequence reads to a gene of interest of a reference sequence or modified reference genome. In certain embodiments an outcome is transferred from an outcome module to a display module where an outcome is provided by the display module (e.g., a suitable display, e.g., an LED or the like). In some embodiments an outcome module provides a representation of a genotype (e.g., a genotype sequence, a genotype image) to a display.

Genetic Variations and Medical Conditions

In some embodiments a system, process or method described herein determines the presence or absence of a genetic variation in a gene of interest in a subject. In some embodiments, a genetic variation generally represents a particular genetic phenotype present in certain subjects. In some embodiments, a genetic variation represents a particular genotype of a subject. In some embodiments, a genetic variation represents a particular haplotype of a subject. Non-limiting examples of genetic variations include one or more deletions, duplications, insertions, microinsertions, additions, translocations, mutations, substitutions, polymorphisms (e.g., single-nucleotide polymorphisms, multiple nucleotide polymorphisms), fusions, repeats (e.g., short tandem repeats (i.e., STRs)), the like and combinations thereof. In some embodiments, a genetic variation is a single nucleotide polymorphism (SNP). In some embodiments, a genetic variation is a single nucleotide variation (SNV). In certain embodiments a genetic variation comprises one or more nucleotide substitutions within a gene of interest, non-limiting examples of which include A to C, A to G, A to T, C to A, C to G, C to T, T to A, T to C, T to G, G to A, G to C, G to T, and the like. In certain embodiments a nucleotide may have a modified base. An insertion, repeat, deletion, duplication, mutation or polymorphism can be of any length, and in some embodiments, is about 1 nucleotide (nt) to about 250 consecutive megabases (Mb) in length. In some embodiments, an insertion, repeat, STR, deletion, duplication, mutation or polymorphism is about 1 nucleotide (nt) to about 200 nucleotides, about 1 to about 100 nucleotides, about 1 to about 50 nucleotides, about 1 to about 20 nucleotides, about 1 to about 10 nucleotides, or about 1 to about 5 nucleotides in length. In certain embodiments, a method, system or program herein can determine the presence or absence of one or more genetic variation in a gene of interest. In certain embodiments, a method, system or program herein can determine the presence or absence of 1, 2, 3, 4, 5, 6, 7, 8, 9, 10 or more, 20 or more or 50 or more genetic variation in a gene of interest.

A genetic variation can be comprised within a gene of interest. A gene of interest that comprises a genetic variation may include a genetic variation in or near the gene, which genetic variation may be in an intron, exon, untranslated region of a gene, or in a combination thereof. Any gene of interest may comprise a genetic variation that is determined by a method or process described herein.

In certain embodiments a genetic variation, for which the presence or absence is identified for a subject, is sometimes associated with a medical condition.

EXAMPLES

The examples set forth below illustrate certain embodiments and do not limit the technology.

Example 1

Validation a Bioinformatics (BFX) Screen that Calls SNVs and Indels

The objective of the method described below was to validate a bioinformatics (BFX) screen that calls SNVs and insertion/deletions (indels) (collectively, "read-through variants") that reside in exons 12-15 of the human PMS2 gene, or the paralogous exons of PMS2CL.

Background

Lynch syndrome (or hereditary non-polyposis colon cancer) is characterized by familial predisposition to cancers of the colon, endometrium, ovary stomach and urinary tract (Lynch et al., 2009). Most cases of Lynch syndrome are caused by variants in MLH1, MSH2, and MSH6, however 4-11% of cases are caused by PMS2 variants (Gill et al., 2005; Halvarsson, Lindblom, Rambech, Lagerstedt, & Nilbert, 2006; Truninger et al., 2005).

In Lynch Syndrome, testing for inherited variants in the PMS2 gene is hampered by the presence of a pseudogene, PMS2CL, which has nearly identical homology to PMS2 in the last four exons of the gene (exons 12-15). Thus, sequence reads derived from hybridization capture cannot be unambiguously aligned to PMS2 or PMS2CL. Gene conversion between exons 12-15 of PMS2 & PMS2CL further complicates this issue (Hayward et al., 2007). Long range PCR (LR-PCR) has been used by other groups to first generate amplicons specific for PMS2 (or PMS2CL) that can then be sequenced (Clendenning et al., 2006, 2013; Vaughn, Baker, Samowitz, & Swensen, 2013). However, due to the low frequency of variants in these exons, performing LR-PCR on thousands of samples to detect a small number of genetic variations in the PMS2 gene would be impractical and expensive.

To minimize the number of samples that require LR-PCR testing of PMS2 exons 12-15, a two-step protocol was developed:

1. BFX screen—hybridization capture sequence reads from both PMS2 and PMS2CL were aligned only to PMS2 of a reference genome by disrupting the PMS2CL gene of the reference genome and read-through variants were determined based on a ploidy of 4 (2 alleles of PMS2+2 alleles of PMS2CL). See FIG. 1 for a schematic.
2. LR-PCR/Sanger confirmation—Read-through variants identified by the BFX screen are reviewed and classified as if they were in PMS2. Variants are queued for confirmation by LR-PCR and Sanger sequencing. This process disambiguates the location of the variant.

Samples

The BFX screen was validated with samples known to have specific variants in PMS2 exons 12-15 or the paralogous PMS2CL exons 3-6. These samples were obtained internally or from collaborating labs, and the variants were confirmed by Associated Regional and University Pathologists, Inc. ("ARUP") or internally by an orthogonal method (LR-PCR+Miseq sequencing) which represents the gold standard data set.

The validation sample scheme is shown in Table 1. There were a total of 32 unique samples that carry 33 low-frequency variants. Batches 1 and 2 were unique samples. Batch 3 included repeats from both Batches 1 and 2, with intra-batch duplication.

Abbreviations

INT#: An internal sample where the PMS2 or PMS2CL variant was orthogonally determined to be in PMS2 or PMS2CL by LR-PCR followed by MiSeq sequencing. All samples reflected rare variants seen in PMS2 and PMS2CL and which spanned across all four exons of note.

ARUP#: An internal sample sent to ARUP for confirmation. These samples also have LR-PCR+Miseq data.

PC#: An external positive control sample with an external ARUP report.

TABLE 1

Validation scheme for PMS2

| Sample | Batch 1 | Batch 2 | Batch 3 (repeats) |
|---|---|---|---|
| 1 | PC1 | ARUP4 | PC1 |
| 2 | ARUP1 | ARUP5 | ARUP1 |
| 3 | ARUP2 | INT13 | INT01 |
| 4 | ARUP3 | INT14 | INT02 |
| 5 | INT01 | INT15 | ARUP4 |
| 6 | INT02 | INT16 | INT13 |
| 7 | INT03 | INT17 | INT14 |
| 8 | INT04 | INT18 | INT15 |
| 9 | INT05 | INT19 | PC1 |
| 10 | INT06 | INT20 | ARUP1 |
| 11 | INT07 | INT21 | INTI |
| 12 | INT08 | INT22 | INT2 |
| 13 | INT09 | INT23 | ARUP4 |
| 14 | INT10 | INT24 | INT13 |
| 15 | INT11 | INT25 | INT14 |
| 16 | INT12 | INT26 | INT15 |

Sample Details

TABLE 2

Validation sample details. All variants are heterozygous.

| Validation sample ID | Blood IB | gDNA LS number(s) | Variant | Screen Exon | Confirmation Gene |
|---|---|---|---|---|---|
| ARUP1 | IB8166 | LS25953, LS26177, LS26185 | 7:6018315G>C | 13 | PMS2 |
| ARUP2 | IB7947 | LS25964 | 7:6017269G>A | 14 | PMS2 |
| ARUP3 | IB8186 | LS25970 | 7:6017328C>G | 14 | PMS2 |
| ARUP4 | IB2767 | LS26129, LS26181, LS26189 | 7:6018256delTTCT | 13 | PMS2CL |
| ARUP5 | IB7821 | LS26130 | 7:6013060G>C | 15 | PMS2 |
| INT01 | IB4943 | LS25971, LS26178, LS26186 | 7:6013027C>T | 15 | PMS2 |
| INT02 | IB8328 | LS25972, LS26179, LS26187 | 7:6017314C>T | 14 | PMS2 |
| INT03 | IB12765 | LS25973 | 7:6022480C>T | 12 | PMS2 |
| INT04 | IB14405 | LS25974 | 7:6018248CA>TG | 13 | PMS2CL |
| INT05 | IB9552 | LS25975 | 7:6022628G>C | 12 | PMS2CL |
| INT06 | IB2411 | LS25976 | 7:6022502G>A | 12 | PMS2 |
| INT07 | IB9946 | LS25954 | 7:6022521G>A | 12 | PMS2 |
| INT08 | IB10115 | LS25955 | 7:6018237G>A | 13 | PMS2 |
| INT09 | IB13886 | LS25956 | 7:6018320T>C | 13 | PMS2CL |
| INT10 | IB11026 | LS25957 | 7:6017326G>A | 14 | PMS2CL |
| INT11 | IB4700 | LS25958 | 7:6017334G>C | 14 | PMS2 |
| INT12 | IB2427 | LS25959 | 7:6013139A>C | 15 | PMS2CL |
| INT13 | IB21755 | LS26131, LS26182, LS26190 | 7:6022617G>A | 12 | PMS2 |
| INT14 | IB12758 | LS26132, LS26183, LS26191 | 7:6017284G>A | 14 | PMS2CL |
| INT15 | IB20609 | LS26133, LS26184, LS26192 | 7:6022521G>A | 12 | PMS2CL |
| INT16 | IB2744 | LS26134 | 7:6022480C>T | 12 | PMS2 |
| INT17 | IB10652 | LS26135 | 7:6018315G>C | 13 | PMS2 |
| INT18 | IB7816 | LS26136 | 7:6018315G>C | 13 | PMS2 |
| INT19 | IB2954 | LS26137 | 7:6018320T>C | 13 | PMS2CL |
| INT20 | IB10127 | LS26138 | 7:6018320T>C | 13 | PMS2CL |
| INT21 | IB10900 | LS26139 | 7:6018320T>C | 13 | PMS2CL |
| INT22 | IB11892 | LS26140 | 7:6017284G>A | 14 | PMS2CL |
| INT23 | IB5606 | LS26141 | 7:6017284G>A | 14 | PMS2CL |
| INT24 | IB8450 | LS26142 | 7:6017284G>A | 14 | PMS2CL |
| INT25 | IB10386 | LS26143 | 7:6017284G>A | 14 | PMS2CL |
| INT26 | IB12660 | LS26144 | 7:6022480C>T; 7:6017284G>A | 12; 14 | PMS2; PMS2CL |

TABLE 2-continued

Validation sample details. All variants are heterozygous.

| Validation sample ID | Blood IB | gDNA LS number(s) | Variant | Screen Exon | Confirmation Gene |
|---|---|---|---|---|---|
| PC1 | IB2817 | LS25960, LS26180, LS26188 | 7:6022613delC | 12 | PMS2 |

Assay & Workflow

Figure 2:
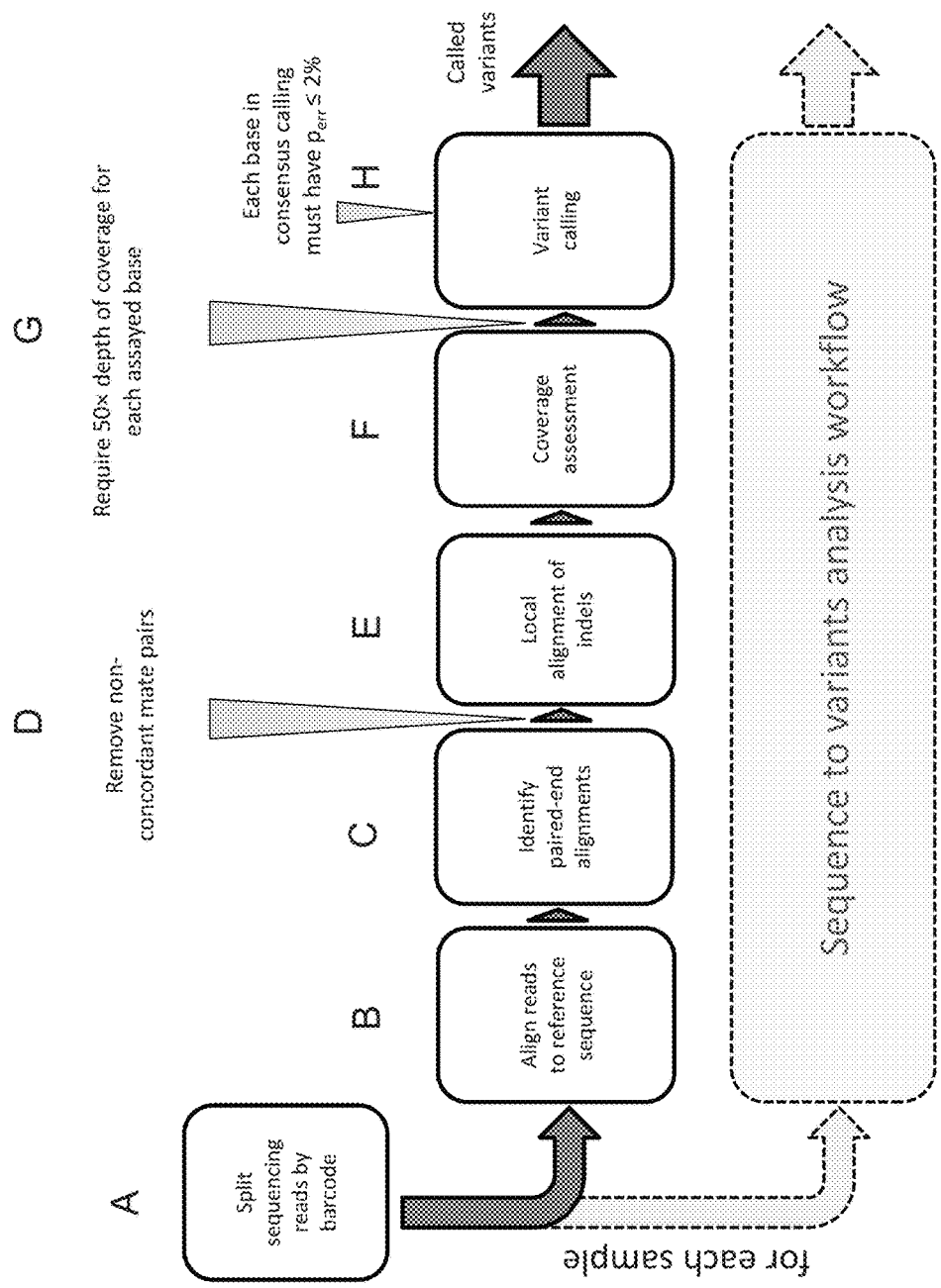
FIG. 2 shows an embodiment of a general sequencing analysis workflow.

Each batch was run through an enrichment workflow (e.g., see FIG. 2 and as summarized below).

After DNA libraries were sequenced using the HiSeq sequencing platform, sequencing reads were available for computational analysis to identify genomic variants present in the original DNA versus the human genome reference sequence where the PMS2CL gene of the reference genome was substantially altered. The overall sequence-to-variants pipeline closely follows the workflow used by the 1,000 Genomes Project (Consortium 1. G., 2010) (McKenna A, 2010) (DePristo M A, 2011) and uses several publically available analysis tools developed in association with that project.

The first stage of sequencing analysis (see FIG. 2A) is de-multiplexing the molecular barcode to identify the sample which generated each read. Only reads with perfect matches to expected barcodes are accepted for further analysis. At this point, subsequent analysis is performed on a sample-by-sample basis using only the reads for each sample.

The next stage of per-sample analysis (FIG. 2B) was to align the sequence reads to the human genome reference sequence version GRCh37 (Church D M, 2011) using the BWA alignment algorithm (Li H D. R., Fast and accurate short read alignment with Burrows-Wheeler transform, (2009)) where the reference genome was modified by disrupting the PMS2CL gene. Sequence reads generated by the HiSeq sequencing platform were paired-end reads, meaning that for each sequenced cluster a forward and reverse read was generated, with these reads corresponding to the ends of the sequenced DNA fragment.

The sequencing workflow generates 150 bp forward and reverse reads. The BWA algorithm provides metrics which indicate whether the forward and reverse reads align in the expected physical orientation, and if the distance between forward and reverse alignments is within 6 standard deviations of the mean insert size (FIG. 2C) (A full description of the distance cutoff used to define properly paired reads can be found online in the BWA user manual [http://bio-bwa.sourceforge.net/bwa.shtml]. Only reads that are aligned correctly by these criteria are accepted for further downstream processing.

After initial alignment and filtering for correct pairwise alignments (FIG. 2D), aligned reads were locally realigned in regions of common indel variation to maximize statistical power for calling indel variation (McKenna A, 2010) (FIG. 2E). At this step regions of the gene of interest which were covered by 50-fold coverage or more with correctly aligned reads were identified (FIG. 2G) to provide sufficient statistical power for the final variant calling stage.

The last stage of analysis (FIG. 2H) is to examine aligned reads and identify high-confidence variation versus the reference sequence. Variants were identified using a number of methods: 1) the Unified Genotyper algorithm from the Genome Analysis Toolkit (DePristo M A, 2011); 2) Free-Bayes (Garrison, submitted); 3) a custom evidence-based caller for complex repetitive loci (currently used only for CFTR intron 8 and MSH2 intron 5); and 4) CNVitae, a custom CNV caller.

The product of the analysis pipeline (FIG. 2A-H) was a set of high-quality variant calls for each sample for the regions of the genome which have a depth of coverage of 50-fold or higher.

The enrichment data were processed by a bioinformatics pipeline. The samples then went through LR-PCR specific for both PMS2 and PMS2CL, followed by Sanger sequencing confirmation of the relevant exon(s) through an external service provider to disambiguate the location of the mutation.

Acceptance Criteria

As per CDC recommendations (Gargis et al., 2012), the following performance metrics were provided: accuracy, precision, analytical sensitivity and specificity. In addition, false discovery rate (FDR) as a measure of the positive predictive value of our test was provided.

Accuracy

Accuracy for NGS was defined as the degree of agreement between the nucleic acid sequences derived from the assay and the gold standard, low-frequency variants found in Table 2. The goal was to have concordance of 100% between our results and the gold standard.

Precision

Precision was defined as degree to which a repeated measurement gives the same result. Precision was analyzed in the assay using measures of reproducibility. To assess inter-run reproducibility, eight samples were run in duplicate across sequencing runs. To assess intra-run reproducibility, eight samples were run in duplicate within an individual sequencing run. The goal was to have an inter- and intra-run reproducibility of 100%.

Analytical Sensitivity/Specificity and False Discovery Rate

TABLE 3

Statistical definitions of Sensitivity and Specificity, as applied to this study.

|  |  | Gold Standard | |
|---|---|---|---|
|  |  | Gold Standard Positive | Gold Standard Negative |
| WGS outcome | WGS Positive | True Positive (TP) | False Positive (FP) |

TABLE 3-continued

Statistical definitions of Sensitivity and Specificity, as applied to this study.

|  |  | Gold Standard | |
|---|---|---|---|
|  |  | Gold Standard Positive | Gold Standard Negative |
| WGS Negative |  | False Negative (FN) | True Negative (TN) |
|  |  | Sensitivity = Σ True Positive/ Σ Condition Positive | Specificity = Σ True Negative/ Σ Condition Negative |

To assess sensitivity and specificity, variant calls were compared to the gold standard calls for the same sample (also see Table 3). Each call was classified under the following definitions:

True positive (TP)—called variant in BFX screen and LR-PCR+Sanger agrees with a known variant at this position True negative (TN)—BFX screen agrees with the reference sequence and the expected call is reference agreement False positive (FP)—called variant in BFX screen and LR-PCR+Sanger does not agree with the known sequence at this location False negative (FN)—BFX screen agrees with the reference sequence and the expected call is a variant.

Wth these definitions, sensitivity, specificity, and false discovery rate were calculated according to Sensitivity=#TP/(#TP+#FN)*100. This is a measure of the test's ability to correctly identify a known variant. Acceptance criterion is ≥95%.

Specificity=#TN/(#TN+#FP)*100. A measure of the test's ability to correctly identify a negative result (no variation). Acceptance criterion is ≥99%.

False Discovery Rate (FDR)=#FP/(#TP+#FP)*100. A measure of the test's error rate, which is inversely correlated with the positive predictive value (PPV). FDR is calculated as 1-PPV. The PPV of a test is the ability to correctly predict a positive result (TP/(TP+FP)). Acceptance criterion is <1%.

Results

TABLE 4

Validation results.

| Validation sample ID | Validation mutation(s) | Gene | gDNA LS number | RU | True Pos. | True Neg. | False Pos. | False Neg. | Sensitivity | Specificity | FDR | Notes |
|---|---|---|---|---|---|---|---|---|---|---|---|---|
| ARUP1 | 7:6018315G>C | PMS2 | LS25953 | RU4572 | 3 | 744 | 0 | 0 | 100.00% | 100.00% | 0.00% | ++ |
|  |  |  | LS26185 | RU4585 | 3 | 744 | 0 | 0 | 100.00% | 100.00% | 0.00% |  |
| ARUP2 | 7:6017269G>A | PMS2 | LS25964 | RU4572 | 7 | 740 | 0 | 0 | 100.00% | 100.00% | 0.00% |  |
| ARUP3 | 7:6017328C>G | PMS2 | LS25970 | RU4572 | 3 | 744 | 0 | 0 | 100.00% | 100.00% | 0.00% |  |
| ARUP4 | 7:6018256delTTCT | PMS2CL | LS26129 | RU4584 | 3 | 741 | 0 | 0 | 100.00% | 100.00% | 0.00% |  |
|  |  |  | LS26181 | RU4585 | 3 | 741 | 0 | 0 | 100.00% | 100.00% | 0.00% |  |
|  |  |  | LS26189 | RU4585 | 3 | 741 | 0 | 0 | 100.00% | 100.00% | 0.00% |  |
| ARUP5 | 7:6013060G>C | PMS2 | LS26130 | RU4584 | 4 | 743 | 0 | 0 | 100.00% | 100.00% | 0.00% |  |
| INT01 | 7:6013027C>T | PMS2 | LS25971 | RU4572 | 5 | 742 | 0 | 0 | 100.00% | 100.00% | 0.00% |  |
|  |  |  | LS26178 | RU4585 | 5 | 742 | 0 | 0 | 100.00% | 100.00% | 0.00% |  |
|  |  |  | LS26186 | RU4585 | 5 | 742 | 0 | 0 | 100.00% | 100.00% | 0.00% |  |
| INT02 | 7:6017314C>T | PMS2 | LS25972 | RU4572 | 2 | 745 | 0 | 0 | 100.00% | 100.00% | 0.00% |  |
|  |  |  | LS26179 | RU4585 | 2 | 745 | 0 | 0 | 100.00% | 100.00% | 0.00% |  |
|  |  |  | LS26187 | RU4585 | 2 | 745 | 0 | 0 | 100.00% | 100.00% | 0.00% |  |
| INT03 | 7:6022480C>T | PMS2 | LS25973 | RU4572 | 5 | 742 | 0 | 0 | 100.00% | 100.00% | 0.00% |  |
| INT04 | 7:6018248CA>TG,CG | PMS2CL | LS25974 | RU4572 | 2 | 744 | 0 | 0 | 100.00% | 100.00% | 0.00% |  |

TABLE 4-continued

Validation results.

| Validation sample ID | Validation mutation(s) | Gene | gDNA LS number | RU | True Pos. | True Neg. | False Pos. | False Neg. | Sensitivity | Specificity | FDR | Notes |
|---|---|---|---|---|---|---|---|---|---|---|---|---|
| INT05 | 7:6022628G>C | PMS2CL | LS25975 | RU4572 | 6 | 741 | 0 | 0 | 100.00% | 100.00% | 0.00% | |
| INT06 | 7:6022502G>A | PMS2 | LS25976 | RU4572 | 1 | 744 | 0 | 0 | 100.00% | 100.00% | 0.00% | ** |
| INT07 | 7:6022521G>A | PMS2 | LS25954 | RU4572 | 6 | 741 | 0 | 0 | 100.00% | 100.00% | 0.00% | |
| INT08 | 7:6018237G>A | PMS2 | LS25955 | RU4572 | 6 | 741 | 0 | 0 | 100.00% | 100.00% | 0.00% | |
| INT09 | 7:6018320T>C | PMS2CL | LS25956 | RU4572 | 7 | 739 | 0 | 0 | 100.00% | 100.00% | 0.00% | |
| INT10 | 7:6017326G>A | PMS2CL | LS25957 | RU4572 | 3 | 744 | 0 | 0 | 100.00% | 100.00% | 0.00% | |
| INT11 | 7:6017334G>C | PMS2 | LS25958 | RU4572 | 5 | 742 | 0 | 0 | 100.00% | 100.00% | 0.00% | |
| INT12 | 7:6013139A>C | PMS2CL | LS25959 | RU4572 | 5 | 742 | 0 | 0 | 100.00% | 100.00% | 0.00% | |
| INT13 | 7:6022617G>A | PMS2 | LS26131 | RU4584 | 4 | 743 | 0 | 0 | 100.00% | 100.00% | 0.00% | |
| | | | LS26182 | RU4585 | 4 | 743 | 0 | 0 | 100.00% | 100.00% | 0.00% | |
| | | | LS26190 | RU4585 | 4 | 743 | 0 | 0 | 100.00% | 100.00% | 0.00% | |
| INT14 | 7:6017284G>A | PMS2CL | LS26132 | RU4584 | 7 | 740 | 0 | 0 | 100.00% | 100.00% | 0.00% | |
| | | | LS26183 | RU4585 | 7 | 740 | 0 | 0 | 100.00% | 100.00% | 0.00% | |
| | | | LS26191 | RU4585 | 7 | 740 | 0 | 0 | 100.00% | 100.00% | 0.00% | |
| INT15 | 7:6022521G>A | PMS2CL | LS26133 | RU4584 | 5 | 742 | 0 | 0 | 100.00% | 100.00% | 0.00% | |
| | | | LS26184 | RU4585 | 5 | 742 | 0 | 0 | 100.00% | 100.00% | 0.00% | |
| | | | LS26192 | RU4585 | 5 | 742 | 0 | 0 | 100.00% | 100.00% | 0.00% | |
| INT16 | 7:6022480C>T | PMS2 | LS26134 | RU4584 | 2 | 745 | 0 | 0 | 100.00% | 100.00% | 0.00% | |
| INT17 | 7:6018315G>C | PMS2 | LS26135 | RU4584 | 5 | 742 | 0 | 0 | 100.00% | 100.00% | 0.00% | |
| INT18 | 7:6018315G>C | PMS2 | LS26136 | RU4584 | 3 | 744 | 0 | 0 | 100.00% | 100.00% | 0.00% | |
| INT19 | 7:6018320T>C | PMS2CL | LS26137 | RU4584 | 4 | 742 | 0 | 0 | 100.00% | 100.00% | 0.00% | |
| INT20 | 7:6018320T>C | PMS2CL | LS26138 | RU4584 | 5 | 741 | 0 | 0 | 100.00% | 100.00% | 0.00% | |
| INT21 | 7:6018320T>C | PMS2CL | LS26139 | RU4584 | 9 | 737 | 0 | 0 | 100.00% | 100.00% | 0.00% | |
| INT22 | 7:6017284G>A | PMS2CL | LS26140 | RU4584 | 5 | 742 | 0 | 0 | 100.00% | 100.00% | 0.00% | |
| INT23 | 7:6017284G>A | PMS2CL | LS26141 | RU4584 | 3 | 744 | 0 | 0 | 100.00% | 100.00% | 0.00% | |
| INT24 | 7:6017284G>A | PMS2CL | LS26142 | RU4584 | 3 | 744 | 0 | 0 | 100.00% | 100.00% | 0.00% | |
| INT25 | 7:6017284G>A | PMS2CL | LS26143 | RU4584 | 3 | 744 | 0 | 0 | 100.00% | 100.00% | 0.00% | |
| INT26 | 7:6022480C>T;7:60172846>A | PMS2; PMS2CL | LS26144 | RU4584 | 7 | 740 | 0 | 0 | 100.00% | 100.00% | 0.00% | |
| PC1 | 7:6022613delC | PMS2 | LS25960 | RU4572 | 4 | 739 | 0 | 0 | 100.00% | 100.00% | 0.00% | ** |
| | | | LS26180 | RU4585 | 4 | 739 | 0 | 0 | 100.00% | 100.00% | 0.00% | ** |
| | | | LS26188 | RU4585 | 4 | 739 | 0 | 0 | 100.00% | 100.00% | 0.00% | ** |

True Pos. = True Positive; True Neg. = True Negative; False Pos. = False Positive; False Neg. = False Negative.
++indicates ARUP1 had a failure of one of the intra-run duplicates during the enrichment process leading to RU4585. Therefore, ARUP1 was not part of the intra-run reproducibility statistics, but was still included in the calculation of inter-run reproducibility.
**Indicates these samples only had gold standard data for PMS2 and not PMS2CL. Thus, specificity for these samples is only calculated for PMS2.

Accuracy

Of the 32 unique samples carrying 33 low-frequency mutations in PMS2 or PMS2CL, the BFX screen discovered all 33, and all 33 were confirmed to be in the correct gene by LR-PCR+Sanger sequencing relative to the gold standard (Table 4). Thus, the accuracy of the BFX screen is 100%.

Precision

Eight samples were run across multiple sequencing runs to assess inter-run reproducibility, and these same eight samples were in duplicate within a single sequencing run to assess intra-run reproducibility. The sample ARUP1 had a failure of one of the intra-run duplicates during the enrichment process leading to RU4585. Therefore, ARUP1 is not part of the intra-run reproducibility statistics, but is still included in the calculation of inter-run reproducibility.

All eight samples displayed perfect inter-run reproducibility for the low-frequency validation mutations (Table 4). The seven samples with intra-run reproducibility data also showed perfect reproducibility (Table 4). Therefore, overall precision for the BFX screen was 100%.

Analytical Sensitivity

All 205 true positive variants were identified by the BFX screen and confirmed to be in the correct gene by LR-PCR+Sanger relative to the gold standard data (Table 4). No false negative variants were observed in the BFX screen. Our sensitivity is thus=205/(205+0)*100=100%.

Analytical Specificity

All 34,876 true negative (reference matching) sites were correctly identified by the BFX screen, and no false positive variant were identified (Table 4). Our specificity is thus=34876/(34876+0)*100=100%.

Samples INT06 and PC1 did not have gold standard data for PMS2CL, so specificity was calculated for PMS2 only for these samples.

False Discovery Rate

No false positives mutations were discovered in the BFX screen, and all true positives were correctly discovered. Our False Discovery Rate (FDR) is thus=0/(205+0)*100=0%. The Positive Predictive Value of the screen was thus 100%−0%=100%

References

Clendenning, M., Hampel, H., LaJeunesse, J., Lindblom, A., Lockman, J., Nilbert, M., . . . De La Chapelle, A. (2006). *Long-range PCR facilitates the identification of PMS2-specific mutations*. Human Mutation, 27, 490-495.

Clendenning, M., Walsh, M. D., Gelpi, J. B., Thibodeau, S. N., Lindor, N., Potter, J. D., . . . Buchanan, D. D. (2013). *Detection of large scale 3' deletions in the PMS2 gene amongst Colon-CFR participants: Have we been missing anything?* Familial Cancer, 12, 563-566.

Gargis, A. S., Kalman, L., Berry, M. W., Bick, D. P., Dimmock, D. P., Hambuch, T., . . . Lubin, I. M. (2012). *Assuring the quality of next-generation sequencing in clinical laboratory practice*. Nature Biotechnology, 30(11), 1033-6.

Gill, S., Lindor, N. M., Burgart, L. J., Smalley, R., Leontovich, O., French, A., . . . Thibodeau, S. N. (2005). *Isolated loss of PMS2 expression in colorectal cancers:*

*Frequency, patient age, and familial aggregation.* Clinical Cancer Research, 11, 6466-6471.

Halvarsson, B., Lindblom, A., Rambech, E., Lagerstedt, K., & Nilbert, M. (2006). *The added value of PMS2 immunostaining in the diagnosis of hereditary nonpolyposis colorectal cancer.* Familial Cancer, 5, 353-358.

Hayward, B. E., De Vos, M., Valleley, E. M. A., Charlton, R. S., Taylor, G. R., Sheridan, E., & Bonthron, D. T. (2007). *Extensive gene conversion at the PMS2 DNA mismatch repair locus.* Human Mutation, 28(5), 424-30.

Lynch, H. T., Lynch, P. M., Lanspa, S. J., Snyder, C. L., Lynch, J. F., & Boland, C. R. (2009). *Review of the Lynch syndrome: History, molecular genetics, screening, differential diagnosis, and medicolegal ramifications.* Clinical Genetics.

Truninger, K., Menigatti, M., Luz, J., Russell, A., Haider, R., Gebbers, J. O., . . . Marra, G. (2005). *Immunohistochemical analysis reveals high frequency of PMS2 defects in colorectal cancer.* Gastroenterology, 128, 1160-1171.

Vaughn, C. P., Baker, C. L., Samowitz, W. S., & Swensen, J. J. (2013). *The frequency of previously undetectable deletions involving 3' Exons of the PMS2 gene.* Genes Chromosomes and Cancer, 52, 107-112.

Example 2

To identify the presence or absence of known genetic variations in exons 12-15 of the human PMS2 gene that are associated with Lynch syndrome, blood samples will be obtained from the blood of human subjects, genomic DNA will be isolated from the samples and the genomic DNA of the samples will be sequenced using an NGS method wherein paired-end reads are generated from each sample. The human genome reference sequence version GRCh37 will be modified by replacing all nucleotides of the PMS2CL gene, including 5' flanking untranslated regions, with an N. The sequence reads obtained will be mapped to the modified human genome reference sequence using the BWA alignment algorithm (Li H D. R., Fast and accurate short read alignment with Burrows-Wheeler transform., (2009)) setting a ploidy of 4. Subjects having only reads that map to PMS2 and that lack the disease-causing variants in PMS2 will be quickly identified using a modified version of the Genome Analysis Toolkit. Samples from the subset of subjects having reads that contain a known genetic variations in exons 12-15 of the human PMS2 gene that is associated with Lynch syndrome will be subjected to further analysis. This subset of subjects will be designated as having a likelihood of having Lynch syndrome (e.g., a likelihood of having a genetic variation associated with Lynch syndrome). Samples from the subset of subjects having a likelihood of having Lynch syndrome will be subjected to LR-PCR for the gene regions of interest suspected of comprising the genetic variations. Amplicons will be sequenced using a Sanger sequencing method and sequences of the gene regions of interest will be determined and analyzed for the presence or absence of the disease-causing genetic variations in PMS2.

Example 3

Validation of a Bioinformatics Screen that Calls Copy Number Variants (CNVs)

The objective of this Example was to validate an assay for calling copy number variants (CNVs) that reside in exons 12-15 of PMS2, or the paralogous exons 3-6 of PMS2CL. Accurately calling CNVs in these exons is important since ~12% of individuals with immunohistochemical staining suggestive of PMS2 mutations have a PMS2 deletion in this region (Vaughn, Baker, Samowitz, & Swensen, 2013). A method that uses multiplex ligation-dependent probe amplification (MLPA) and long-range PCR (LR-PCR) to disambiguate CNVs in exons 12-15 of PMS2 rather than exons 3-6 of PMS2CL has been developed (Vaughn, Hart, Samowitz, & Swensen, 2011). However, due to the low frequency of variants in these exons, performing MLPA and LR-PCR on a large number of samples for detection of CNVs in the PMS2 gene is impractical and expensive. To minimize the number of samples that require MLPA and LR-PCR testing of PMS2 exons 12-15, a three-step protocol was developed:

Bioinformatics (BFX) screen—hybridization capture reads from exons 12-15 of PMS2 and exons 3-6 of PMS2CL were aligned to exons 12-15 of PMS2 only and CNVs were determined based on a ploidy of 4 (2 alleles of PMS2+2 alleles of PMS2CL).

MLPA confirmation/finishing—CNVs identified by the BFX screen were reviewed and classified as if they were in PMS2. Variants were queued for confirmation by MLPA.

LR-PCR/Sanger disambiguation—Confirmed variants were still ambiguously located in either PMS2 or PMS2CL due to the possibility of gene conversion. LR-PCR and Sanger sequencing of the fixed differences between PMS2 and PMS2CL was used to disambiguate the location of the variant.

Samples

The assay for PMS2 exons 12-15 CNVs was validated with samples known to have specific variants in the genes/regions targeted. These samples were obtained internally or from collaborating labs, and the variants were confirmed by external labs. A unique circumstance for this assay was that all variants first required a BFX screen to ambiguously call variants in PMS2 or PMS2CL, followed by the MLPA confirmation and LR-PCR+Sanger disambiguation. For these situations, the BFX analysis step, as well as the downstream lab processes were validated together.

The BFX portion of the validation scheme is shown in Table 5. There were a total of 28 unique samples across 8 batches. Batches 1-5 have unique samples. Batches 6-8 have a mixture of unique samples and inter- and intra-run replicates.

TABLE 5

Validation scheme for PMS2 del/dup. (E) is an inter-run replicate. (A) is an intra-run replicate.

| Batch 1 | Batch 2 | Batch 3 | Batch 4 | Batch 5 | Batch 6 | Batch 7 | Batch 8 |
|---|---|---|---|---|---|---|---|
| NEG1 | NEG5 | FULL10 | PART1 | COMM4 | FULL1 (A) | FULL8 | FULL10 (E) |
| NEG2 | NEG6 | FULL1 | PART2 | | FULL1 (A) | FULL12 | PART2 (E) |
| NEG3 | | COMM1 | FULL3 | | FULL6 (A) | FULL9 | FULL4 (E) |
| NEG4 | | COMM2 | FULL4 | | FULL6 (A) | PART4 | FULL7 (E) |

TABLE 5-continued

Validation scheme for PMS2 del/dup. (E) is an inter-run replicate. (A) is an intra-run replicate.

| Batch 1 | Batch 2 | Batch 3 | Batch 4 | Batch 5 | Batch 6 | Batch 7 | Batch 8 |
|---|---|---|---|---|---|---|---|
| | | FULL2 | FULL5 | | PART3 | FULL7 (E) | |
| | | PART5 | FULL6 | | COMM3 | | |
| | | NEG7 | | | FULL7 | | |
| | | | | | FULL11 | | |
| | | | | | FULL10 (E) | | |
| | | | | | PART2 (E) | | |
| | | | | | FULL4 (E) | | |

Each batch was run through the DuranDuran enrichment workflow in a clinical setting. This validation focused on applying the BFX screen described above to the existing data, and subsequent CNV confirmation by MLPA and disambiguation by LR-PCR+Sanger.

Abbreviations

NEG#: A CNV negative sample for the region of interest. Has a clinical report from ARUP.

FULL#: A CNV positive sample in the region of interest and has a clinical report that leaves no ambiguity regarding the extent or location of the mutation.

PART#: A CNV positive sample in the region of interest but has a clinical report that is ambiguous for the extent or location of the mutation.

COMM#: A CNV positive sample in the region of interest through personal communication with the collaborating lab, but does not have a clinical report. One of these samples has a publication describing the mutation, and three other samples have an email exchange with the lab describing mutation evidence.

Sample Details

TABLE 6

Validation sample details

| Validation sample ID | IB number | Reported mutation: Exons(s) mutated & copy number | Confirmation gene |
|---|---|---|---|
| NEG1 | IB2817 | normal | N/A |
| NEG2 | IB8186 | normal | N/A |
| NEG3 | IB7947 | normal | N/A |
| NEG4 | IB8166 | normal | N/A |
| NEG5 | IB7821 | normal | N/A |
| NEG6 | IB2767 | normal | N/A |
| NEG7 | IB17142 | normal | N/A |
| FULL1 | IB17468 | e14 CN1 | PMS2 |
| FULL2 | IB9580 | e1-15 CN1 | PMS2 |
| FULL3 | IB19243 | e11-15 CN1 | PMS2 |
| FULL4 | IB19897 | e11-15 CN1 | PMS2 |
| FULL5 | IB40214 | e11-15 CN1 | PMS2 |
| FULL6 | IB41108 | e11-15 CN1 | PMS2 |
| FULL7 | IB31098 | e5-15 CN1 | PMS2 |
| FULL8 | IB44542 | e2-15 CN1 | PMS2 |
| FULL9 | IB44545 | e2-15 CN1 | PMS2 |
| FULL10 | IB17140 | e1-14 CN1 | PMS2 |
| FULL11 | IB31866 | e1-15 CN1 | PMS2 |
| FULL12 | IB44550 | e2-15 CN1 | PMS2 |
| PART1 | IB17162 | e1-12+ CN1 | PMS2 |
| PART2 | IB17297 | e1-12+ CN1 | PMS2 |
| PART3 | IB20718 | e1-12+ CN1 | PMS2 |
| PART4 | IB30873 | e13-14 CN1 | ambiguous |
| PART5 | IB2596 | e13-14 CN1 | ambiguous |
| COMM1 | IB23623 | e14 CN1 | PMS2 |
| COMM2 | IB23624 | e14 CN1 | PMS2 |
| COMM3 | IB23046 | e2-15 CN0 | PMS2 |
| COMM4 | IB42687 | e13-15 CN3 | PMS2CL |

Assay

Each batch was run through the DuranDuran enrichment workflow. All samples were run on MLPA to confirm the variant, and if present, the samples was run through LR-PCR specific for both PMS2 and PMS2CL, followed by Sanger sequencing of the fixed differences in the relevant exon(s) between the PMS2 and PMS2CL reference sequence to disambiguate the location of the mutation. See (Vaughn et al., 2011) for a description of the MLPA/LR-PCR assay and CNV disambiguation methodology.

Acceptance Criteria

As per the CDC recommendations (Gargis et al., 2012), the following performance metrics were provided: accuracy, precision, analytical sensitivity and specificity. In addition, false discovery rate (FDR) was provided as a measure of the positive predictive value of the test. Since this assay assesses deletions and duplication of entire exons, each exon in PMS2 exons 12-15 or the paralogous exons 3-6 of PMS2CL is the smallest granular unit comprising the acceptance criteria below.

Accuracy

Accuracy for NGS is defined as the degree of agreement between our assay and the gold standard variants found in Table 2. The goal was to have concordance of 100% between the results and the gold standard.

Precision

Precision is defined as degree to which a repeated measurement gives the same result. Precision was analyzed using measures of reproducibility. To assess inter-run reproducibility, four samples were run in triplicate across sequencing runs. To assess intra-run reproducibility, two samples were run in duplicate within an individual sequencing run. Our goal was to have an inter- and intra-run reproducibility of 100%.

Analytical Sensitivity/Specificity and False Discovery Rate

To assess sensitivity and specificity, variant calls were compared to the gold standard calls for the same sample (also see Table 3). Each call was classified under the following definitions:

True positive (TP)—called variant in BFX screen/MLPA/LR-PCR+Sanger agrees with a known variant at this position.

True negative (TN)—BFX screen is negative and the known copy number status is negative. No further testing was done.

False positive (FP)—called variant in BFX screen/MLPA/LR-PCR+Sanger does not agree with the known variant status at this location False negative (FN)—BFX screen is negative and the expected call is a variant. With these definitions, sensitivity, specificity, and false discovery rate were calculated according to:

Sensitivity=#TP/(#TP+#FN)*100. This is a measure of the test's ability to correctly identify a known variant. Acceptance criterion is ≥95%

Specificity=#TN/(#TN+#FP)*100. A measure of the test's ability to correctly identify a negative result (no variation). Acceptance criterion is ≥99%

False Discovery Rate (FDR)=#FP/(#TP+#FP)*100. A measure of the test's error rate, which is inversely correlated with the positive predictive value (PPV). FDR is calculated as 1-PPV. The PPV of a test is the ability to correctly predict a positive result (TP/(TP+FP)). Acceptance criterion is <1%.

TABLE 7

Statistical definitions of Sensitivity and Specificity, as applied to this study.

| | | Gold Standard | |
|---|---|---|---|
| | | Gold Standard Positive | Gold Standard Negative |
| WGS outcome | WGS Positive | True Positive (TP) | False Positive (FP) |
| | WGS Negative | False Negative (FN) | True Negative (TN) |
| | | Sensitivity = Σ True Positive/ Σ Condition Positive | Specificity = Σ True Negative/ Σ Condition Negative |

Results

TABLE 8

Validation results summary.

| Validation name | Screen results | MLPA results | MLPA SNP-specific CNs | PMS2 Sanger results | PMS2CL Sanger results | Reported mutation: Exons(s) mutated & copy number | Confirmed Mutation | Notes |
|---|---|---|---|---|---|---|---|---|
| NEG1 | negative | negative | 22-13-13-04 | | | normal | normal | |
| NEG2 | negative | negative | 22-22-22-22 | | | normal | normal | |
| NEG3 | negative | negative | 22-13-13-13 | | | normal | normal | |
| NEG4 | negative | negative | 22-22-22-22 | | | normal | normal | |
| NEG5 | negative | negative | 22-31-31-31 | | | normal | normal | |
| NEG6 | negative | negative | 22-13-22-22 | | | normal | normal | |
| NEG7 | negative | negative | 22-22-22-22 | | | normal | normal | |
| FULL1 | e14 CN3 | e14 CN3 | 22-31-21-22 | 14:G | 14:GP | PMS2 e14 CN1 | PMS2 e14 CN1 | |
| FULL1 (A) | e14 CN3 | e14 CN3 | 22-31-21-22 | 14:G | 14:GP | PMS2 e14 CN1 | PMS2 e14 CN1 | |
| FULL1 (A) | e14 CN3 | e14 CN3 | 22-31-21-22 | 14:G | 14:GP | PMS2 e14 CN1 | PMS2 e14 CN1 | |
| FULL2 | e12-15 CN2 | PMS2 e1-11 CN1; e12-15 CN2; PMS2CL e11 CN1 | 11-20-20-20 | 12:G 13:G 14:G 15:G | 12:P 13:G 14:G 15:G | PMS2 e1-15 CN1 | PMS2 e1-15 CN1 | |
| FULL3 | e12-15 CN3 | PMS2 e11 CN1; e12-15 CN3 | 12-21-21-21 | 12:G 13:G 14:G 15:G | 12:P 13:GP 14:GP 15:GP | PMS2 e11-15 CN1 | PMS2 e11-15 CN1 | |
| FULL4 (E) | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |
| FULL4 (E) | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |
| FULL4 (E) | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |
| FULL5 | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |
| FULL6 | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |
| FULL6 (A) | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |
| FULL6 (A) | e12-15 CN3 | PMS2 e11 CN1; e12-15 CN3 | 12-12-12-12 | 12:G 13:G 14:G 15:G | 12:P 13:P 14:P 15:P | PMS2 e11-15 CN1 | PMS2 e11-15 CN1 | |

TABLE 8-continued

Validation results summary.

| Validation name | Screen results | MLPA results | MLPA SNP-specific CNs | PMS2 Sanger results | PMS2CL Sanger results | Reported mutation: Exons(s) mutated & copy number | Confirmed Mutation | Notes |
|---|---|---|---|---|---|---|---|---|
| FULL7 (E) | e12-15 CN3 | PMS2 e5-11 CN1; e12-15 CN3 | 12-12-12-12 | 12:G 13:G 14:G 15:G | 12:P 13:P 14:P 15:P | PMS2 e5-15 CN1 | PMS2 e5-15 CN1 | |
| FULL7 (E) | e12-15 CN3 | PMS2 e5-11 CN1; e12-15 CN3 | 12-12-12-12 | 12:G 13:G 14:G 15:G | 12:P 13:P 14:P 15:P | PMS2 e5-15 CN1 | PMS2 e5-15 CN1 | |
| FULL7 (E) | e12-15 CN3 | PMS2 e5-11 CN1; e12-15 CN3 | 12-12-12-12 | 12:G 13:G 14:G 15:G | 12:P 13:P 14:P 15:P | PMS2 e5-15 CN1 | PMS2 e5-15 CN1 | |
| FULL8 | e12-15 CN3 | PMS2 e2-11 CN1; e12-15 CN3 | 12-21-21-21 | 12:G 13:G 14:G 15:G | 12:P 13:GP 14:GP 15:GP | PMS2 e2-15 CN1 | PMS2 e2-15 CN1 | |
| FULL9 | e12-15 CN3 | PMS2 e2-11 CN1; e12-15 CN3 | 12-21-21-21 | 12:G 13:G 14:G 15:G | 12:P 13:GP 14:GP 15:GP | PMS2 e2-15 CN1 | PMS2 e2-15 CN1 | |
| FULL10 (E) | e12-14 CN3 | PMS2 e1-11 CN1; e12-14 CN3 | 12-12-12-13 | 12:G 13:P 14:P | 12:P 13:GP 14:GP | PMS2 e1-14 CN1 | PMS2 e1-14 CN1 | |
| FULL10 (E) | e12-14 CN3 | PMS2 e1-11 CN1; e12-14 CN3 | 12-12-12-13 | 12:G 13:P 14:P | 12:P 13:GP 14:GP | PMS2 e1-14 CN1 | PMS2 e1-14 CN1 | |
| FULL10 (E) | e12-14 CN3 | PMS2 e1-11 CN1; e12-14 CN3 | 12-12-12-13 | 12:G 13:P 14:P | 12:P 13:GP 14:GP | PMS2 e1-14 CN1 | PMS2 e1-14 CN1 | |
| FULL11 | e12-15 CN3 | PMS2 e1-11 CN1; e12-15 CN3 | 12-21-21-12 | 12:G 13:G 14:G 15:P | 12:P 13:GP 14:GP 15:GP | PMS2 e1-15 CN1 | PMS2 e1-15 CN1 | |
| FULL12 | e12-15 CN3 | PMS2 e2-11 CN1; e12-15 CN3 | 12-03-03-03 | 12:G 13:P 14:P 15:P | 12:P 13:P 14:P 15:P | PMS2 e2-15 CN1 | PMS2 e2-15 CN1 | ++ |
| PART1 | e12-14 CN3 | PMS2 e1-11 CN1; e12-14 CN3 | 12-21-21-22 | 12:G 13:G 14:G | 12:P 13:GP 14:GP | PMS2 e1-12+ CN1 | PMS2 e1-14 CN1 | ** |
| PART2 (E) | e12-14 CN3 | PMS2 e1-11 CN1; e12-14 CN3 | 12-21-21-22 | 12:G 13:G 14:G | 12:P 13:GP 14:GP | PMS2 e1-12+ CN1 | PMS2 e1-14 CN1 | ** |
| PART2 (E) | e12-14 CN3 | PMS2 e1-11 CN1; e12-14 CN3 | 12-21-21-22 | 12:G 13:G 14:G | 12:P 13:GP 14:GP | PMS2 e1-12+ CN1 | PMS2 e1-14 CN1 | ** |
| PART2 (E) | e12-14 CN3 | PMS2 e1-11 CN1; e12-14 CN3 | 12-21-21-22 | 12:G 13:G 14:G | 12:P 13:GP 14:GP | PMS2 e1-12+ CN1 | PMS2 e1-14 CN1 | ** |
| PART3 | e12-14 CN3 | PMS2 e1-11 CN1; e12-14 CN3 | 12-21-21-22 | 12:G 13:G 14:G | 12:P 13:GP 14:GP | PMS2 e1-12+ CN1 | PMS2 e1-14 CN1 | ** |
| PART4 | e13-14 CN3 | e13-14 CN3 | 22-30-30-13 | 13:G 14:G | 13:G 14:G | ambiguous e13-14 CN1 | ambiguous e13-14 CN1 | $$ |
| PART5 | e13-14 CN3 | e13-14 CN3 | 22-03-03-04 | 13:P 14:P | 13:P 14:P | ambiguous e13-14 CN1 | ambiguous e13-14 CN1 | $$ |
| COMM1 | e14 CN3 | e14 CN3 | 22-22-21-22 | 14:G | 14:GP | PMS2 e14 CN1 | PMS2 e14 CN1 | |
| COMM2 | e14 CN3 | e14 CN3 | 22-13-12-22 | 14:G | 14:P | PMS2 e14 CN1 | PMS2 e14 CN1 | |
| COMM3 | e12-15 CN2 | PMS2 e2-11 CN0; e12-15 CN2 | 02-02-02-02 | FAIL | 12:P | PMS2 e2-15 CN0 | PMS2 e2-15 CN0 | |
| COMM4 | e12-15 CN5 | PMS2CL e11 CN3; e12-15 CN5 | 23-23-23-23 | 12:G 13:GP 14:GP 15:GP | 12:P 13:GP 14:GP 15:GP | PMS2CL e13-15 CN3 | PMS2CL e11-15 CN3 | %% |

Screen results were only reported for PMS2 exons 12-15. LR-PCR+Sanger sequencing was not performed for negative samples. "MLPA SNP-specific Copy Numbers" represent the MLPA copy numbers for the SNP probes in exons 12-15. Each doublet of numbers represents the copy number of the PMS2 reference fixed difference followed by the copy number of the PMS2CL reference fixed difference. Sanger sequencing results are displayed as exon:result. G denotes a PMS2 reference fixed difference; P denotes a PMS2CL fixed difference. ++ Indicates mutation was in PMS2 via exon 1-11 probes. ** Only exon 12 counted towards acceptance criteria. $$ Our variant matches external report, but since exons 13 and 14 are ambiguous they were not counted as true positives. %% Indicates the duplication is in PMS2CL via exon 11 probe. External lab did not report on PMS2CL homologous exons 11-12, so they were excluded from the acceptance criteria calculations.

TABLE 9

Per-exon counts of validation results for each sample.

| Validation name | # True Positives | # True Negatives | # False Positives | # False Negatives |
|---|---|---|---|---|
| NEG1 | 0 | 4 | 0 | 0 |
| NEG2 | 0 | 4 | 0 | 0 |
| NEG3 | 0 | 4 | 0 | 0 |
| NEG4 | 0 | 4 | 0 | 0 |
| NEG5 | 0 | 4 | 0 | 0 |
| NEG6 | 0 | 4 | 0 | 0 |
| NEG7 | 0 | 4 | 0 | 0 |
| FULL1 | 1 | 3 | 0 | 0 |
| FULL1 (A) | 1 | 3 | 0 | 0 |
| FULL1 (A) | 1 | 3 | 0 | 0 |
| FULL2 | 4 | 0 | 0 | 0 |
| FULL3 | 4 | 0 | 0 | 0 |
| FULL4 (E) | 4 | 0 | 0 | 0 |
| FULL4 (E) | 4 | 0 | 0 | 0 |
| FULL4 (E) | 4 | 0 | 0 | 0 |
| FULL5 | 4 | 0 | 0 | 0 |
| FULL6 | 4 | 0 | 0 | 0 |
| FULL6 (A) | 4 | 0 | 0 | 0 |
| FULL6 (A) | 4 | 0 | 0 | 0 |
| FULL7 (E) | 4 | 0 | 0 | 0 |
| FULL7 (E) | 4 | 0 | 0 | 0 |
| FULL7 (E) | 4 | 0 | 0 | 0 |
| FULL8 | 4 | 0 | 0 | 0 |
| FULL9 | 4 | 0 | 0 | 0 |
| FULL10 (E) | 3 | 1 | 0 | 0 |
| FULL10 (E) | 3 | 1 | 0 | 0 |
| FULL10 (E) | 3 | 1 | 0 | 0 |
| FULL11 | 4 | 0 | 0 | 0 |
| FULL12 | 4 | 0 | 0 | 0 |
| PART1 | 1 | 0 | 0 | 0 |
| PART2 (E) | 1 | 0 | 0 | 0 |
| PART2 (E) | 1 | 0 | 0 | 0 |
| PART2 (E) | 1 | 0 | 0 | 0 |
| PART3 | 1 | 0 | 0 | 0 |
| PART4 | 0 | 2 | 0 | 0 |
| PART5 | 0 | 2 | 0 | 0 |
| COMM1 | 1 | 3 | 0 | 0 |
| COMM2 | 1 | 3 | 0 | 0 |
| COMM3 | 4 | 0 | 0 | 0 |
| COMM4 | 3 | 0 | 0 | 0 |
| Total | 90 | 50 | 0 | 0 |
| Total for unique samples | 56 | 42 | 0 | 0 |

Accuracy

Of the 21 unique samples harboring 56 known exons of CNV mutations in PMS2 or PMS2CL, the assay correctly called all 56 exons (Table 9). Thus, the accuracy of the BFX screen is 100%.

Precision

Four samples were run across three sequencing, MLPA and LR-PCR runs to assess inter-run reproducibility, and two samples were run in duplicate within a single sequencing, MLPA and LR-PCR run to assess intra-run reproducibility.

All four samples displayed perfect inter-run reproducibility and both samples displayed perfect intra-run reproducibility (Table 8). Therefore, overall precision for the BFX screen is 100%.

Analytical Sensitivity

All 90 true positive CNVs were correctly identified by the assay, including replicates (Table 9). No false negative variants were observed. Our sensitivity is thus=90/(90+0)*100=100%.

Analytical Specificity

All 50 true negative exons were correctly identified by the assay, including replicates (Table 9). Our specificity is thus=50/(50+0)*100=100%.

Our assay identified CNVs in PART1, PART2, PART3 and COMM4 that were not identified in the external labs' clinical reports due to known limitations in the external labs' assays. Since this was a limitation beyond our control, these exons are not counted as false positives.

False Discovery Rate

No false positives mutations were discovered in the assay, and all true positives were correctly identified. Our False Discovery Rate (FDR) is thus=0/(90+0)*100=0%. The Positive Predictive Value (PPV) of the screen is thus 100%—0%=100%

References (For Example 3)

Gargis, A. S., Kalman, L., Berry, M. W., Bick, D. P., Dimmock, D. P., Hambuch, T., . . . Lubin, I. M. (2012). Assuring the quality of next-generation sequencing in clinical laboratory practice. *Nature Biotechnology*, 30(11), 1033-6. http://doi.org/10.1038/nbt.2403

Gill, S., Lindor, N. M., Burgart, L. J., Smalley, R., Leontovich, O., French, A., . . . Thibodeau, S. N. (2005). Isolated loss of PMS2 expression in colorectal cancers: Frequency, patient age, and familial aggregation. *Clinical Cancer Research*, 11, 6466-6471. http://doi.org/10.1158/1078-0432.CCR-05-0661

Halvarsson, B., Lindblom, A., Rambech, E., Lagerstedt, K., & Nilbert, M. (2006). The added value of PMS2 immunostaining in the diagnosis of hereditary nonpolyposis colorectal cancer. *Familial Cancer*, 5, 353-358. http://doi.org/10.1007/s10689-006-0005-9

Hayward, B. E., De Vos, M., Valleley, E. M. A., Charlton, R. S., Taylor, G. R., Sheridan, E., & Bonthron, D. T. (2007). Extensive gene conversion at the PMS2 DNA mismatch repair locus. *Human Mutation*, 28(5), 424-30. http://doi.org/10.1002/humu.20457

Lynch, H. T., Lynch, P. M., Lanspa, S. J., Snyder, C. L., Lynch, J. F., & Boland, C. R. (2009). Review of the Lynch syndrome: History, molecular genetics, screening, differential diagnosis, and medicolegal ramifications. *Clinical Genetics*. http://doi.org/10.1111/j.1399-0004.2009.01230.x Truninger, K., Menigatti, M., Luz, J., Russell, A., Haider, R., Gebbers, J. O., . . . Marra, G. (2005). Immunohistochemical analysis reveals high frequency of PMS2 defects in colorectal cancer. *Gastroenterology*, 128, 1160-1171. http://doi.org/10.1053/j.gastro.2005.01.056

Vaughn, C. P., Baker, C. L., Samowitz, W. S., & Swensen, J. J. (2013). The frequency of previously undetectable deletions involving 3' Exons of the PMS2 gene. *Genes Chromosomes and Cancer*, 52, 107-112. http://doi.org/10.1002/gcc.22011

Vaughn, C. P., Hart, K. J., Samowitz, W. S., & Swensen, J. J. (2011). Avoidance of pseudogene interference in the detection of 3' deletions in PMS2. *Human Mutation*. http://doi.org/10.1002/humu.21540

Example 4

Validation of a Bioinformatics Screen that Calls Read-Through Variants at Ploidy 6

Background

The gene NEB provides instructions for making a protein called nebulin. This protein plays an important role in skeletal muscles. More than 60 rare variations in the NEB gene have been found to cause nemaline myopathy and these variations are not concentrated in any particular region of the coding sequence. Of the 183 exons in the nebulin gene, at least 43 are alternatively spliced, although exons 143 and 144 are not found in the same transcript. The gene contains a triplicated sequence (8.2 kb of genomic sequence spanning 8 exons with high homology (99%) which complicates sequencing of the region (FIG. 1). This triplicated sequence is not polymorphic, however rare sequence changes in the triplicated region may be pathogenic for nemaline myopathy (Donner et al). The exact genomic location of a variant with regards to repeat 1, 2, or 3 is not required for clinical reporting; clinical reporting only requires knowing that there is a variant present within repeats 1, 2, or 3.

Objective

Figure 3:
FIG. 3 shows an illustration of the gene NEB which has a triplicated repeat in its coding region. All intronic sequence is identical between the 3 repeat regions.

The objectives of the method is to enable alignment of reads from NEB Blocks 1-3 (exons 82-105) unambiguously to NEB Block 1 and validate read-through variant calls over the region (FIG. 3). A corresponding change has been made in the reference genome to mask NEB blocks 2-3 (exons 90-105), and to genotype read-through variation relative to ploidy 6 in this region in contrast to the typical ploidy 2. A close inspection of all changes to coverage, alignments, and read-through variant calls has demonstrated that we were able to accurately call variants within NEB Blocks 1-3.

Methods: Implementation

The intrinsic differences between exons in NEB are shown in Table 10.

Results

For testing, we use the following 4 sequencing runs:

RU6191 (48-plex Illumina Hiseq run)

RU6411 (24-plex Illumina Hiseq run)

RU6410 (24-plex Illumina Hiseq run)

RU6369 (24-plex Illumina Hiseq run)

For the sequencing runs, we investigate coverage and variant calls for NEB Blocks 1-3. In addition, we carry out a regression analysis on all samples from a single sequencing run to ensure that the modification to the reference genome (removing NEB Blocks 2 and 3) does not significantly impact alignment, coverage, or variant calling outside of the NEB Blocks 1-3. Finally, we show clinical validation data for the method.

Results: Coverage in NEB Blocks 1-3

Figure 4:
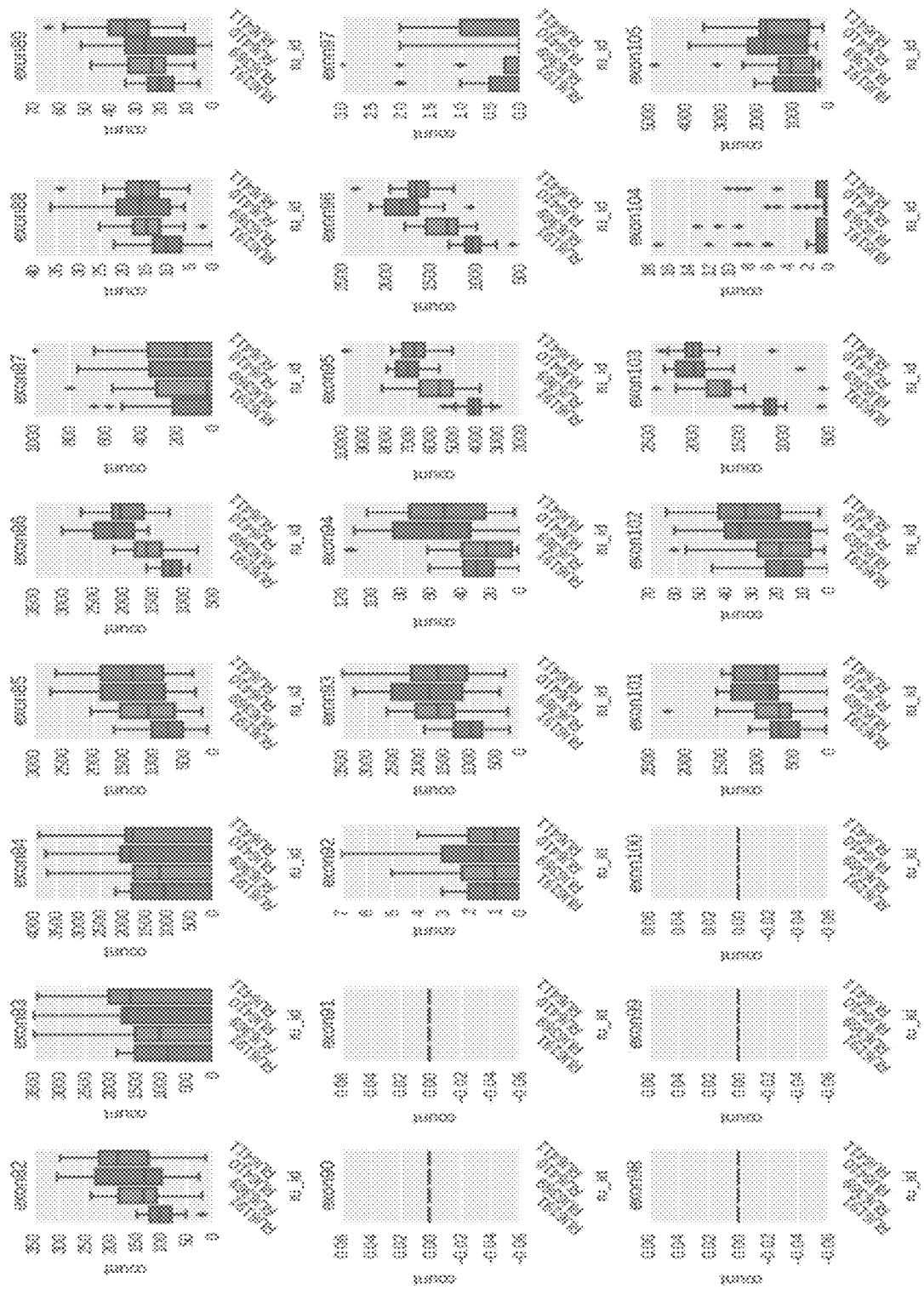
FIG. 4 shows NEB Blocks 1-3 coverage before reference genome modification. Coverage was very low for most exons, with some exception for exons with fixed/reference differences. This was because the sequence read alignment program used (e.g., novoalign) is parameterized so that reads with multiple alignments aren't mapped.
Figure 5:
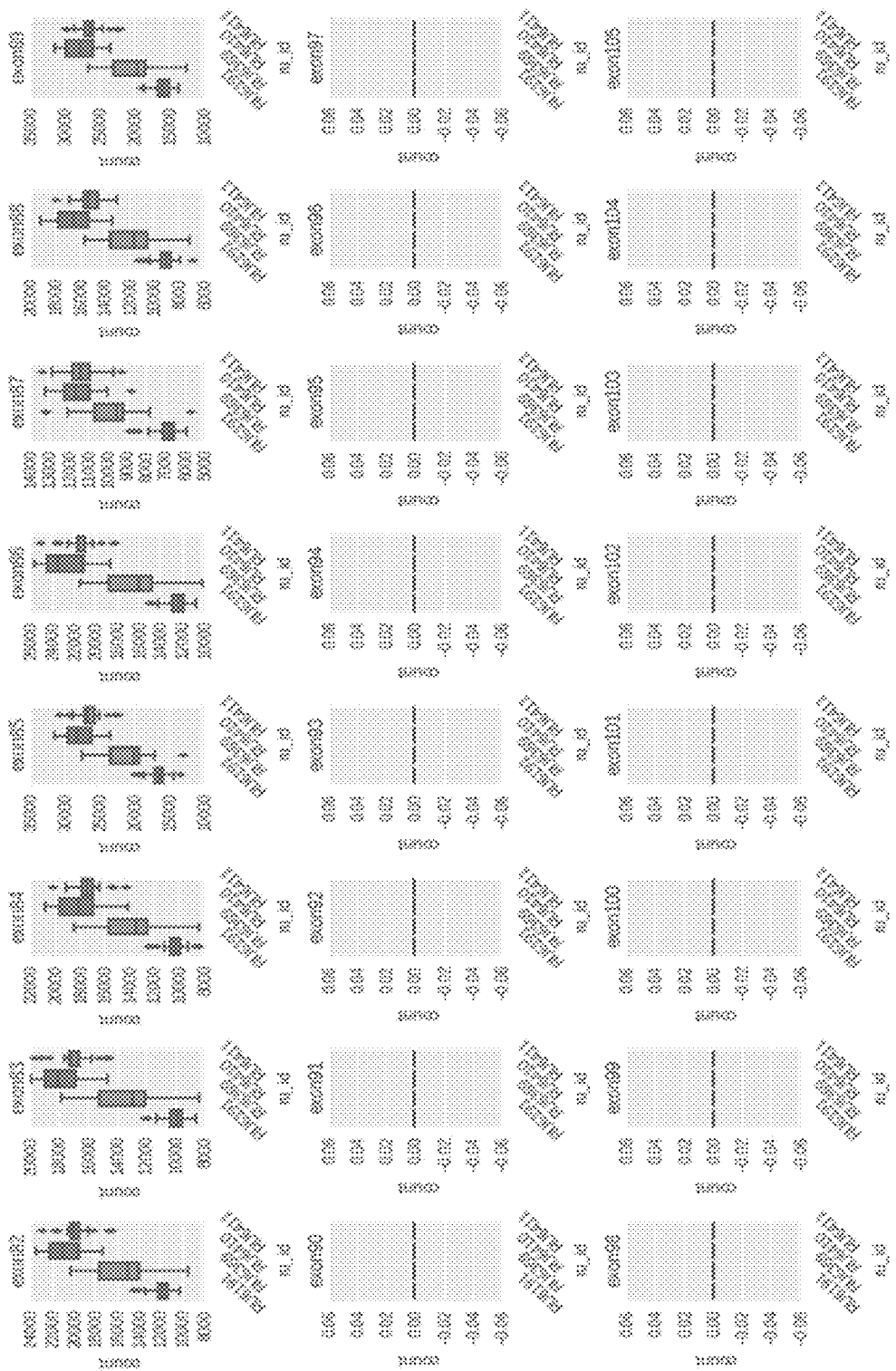
FIG. 5 shows NEB Blocks 1-3 coverage after reference genome modification. Coverage was between 10,000-20,000 for exons in Block 1. Blocks 2-3 now have 0 coverage.

As expected, a large number of reads that were previously aligned to Repeat Blocks 2-3 or previously unmapped, were aligned to Repeat Block 1. See FIGS. 4 and 5.

Results: Read-Through Variants in NEB Blocks 1-3

This section describes the changes in variant calling introduced. Table 11 shows the differences in NEB Block 1-3 variants, both before and after the change to the reference genome. As expected, many variants were gained in NEB Block 1 due to the improved mapping of reads (Unmapped=>Block 1, Ploidy 6), as well as moving all variants from (genomic) Blocks 2 and 3 to Block 1 (Blocks 2-3, Ploidy 2=>Block 1, Ploidy 6). Note also that the variants that were previously called in Block 1 are now called with a different genotype since they're now ploidy 6 calls rather than ploidy 2 calls (Block 1, Ploidy 2=>Block 1, Ploidy 6). All of these differences are desired and anticipated effects of the changes made to the reference genome.

TABLE 10

Intrinsic Variation sites in Repeats 1-3 of NEB.

| Variant | location | exon | base | location | exon | base | location | exon | base |
|---|---|---|---|---|---|---|---|---|---|
| Ivar1 | chr2: 152457023 | 89 | T | chr2: 152446470 | 97 | T | chr2: 152435919 | 105 | C |
| Ivar2 | chr2: 152458415 | 88 | G | chr2: 152447862 | 96 | A | chr2: 152437311 | 104 | G |
| Ivar3 | chr2: 152459116 | 87 | G | chr2: 152448563 | 95 | A | chr2: 152438012 | 103 | G |
| Ivar4 | chr2: 152459193 | 87 | C | chr2: 152448640 | 95 | T | chr2: 152438089 | 103 | C |
| Ivar5 | chr2: 152460241 | 86 | G | chr2: 152449688 | 94 | A | chr2: 152439136 | 102 | A |
| Ivar6 | chr2: 152463200 | 84 | C | chr2: 152452654 | 92 | T | chr2: 152442101 | 100 | T |

Because disambiguating the location of a variant within one of the 3 blocks is irrelevant to interpretation, we have masked Repeat Blocks 2-3 from the reference genome. All relevant reads will now be aligned to Repeat Block 1 with novoalign, and read-through variants (SNVs, indels, multi-nucleotide variants, complex sequence variants) called with an expectation of normal set to be ploidy 6.

Variant calling for NEB Block 1 is being done by free-bayes 0.9.14. Because ploidy 2 filtering strategies are not applicable to ploidy 6 regions, variants calls are not filtered, except for when all alternate alleles are STR expansions or contractions (PIPE's RepeatUnitWobble filter).

TABLE 11

Variant call changes within NEB Blocks 1-3 due to reference genome modification.

| Count | Variant location before reference modification | Variant location after reference modification |
|---|---|---|
| 66 | Block 1, Ploidy 2 | Block 1, Ploidy 6 |
| 267 | Blocks 2-3, Ploidy 2 | Block 1, Ploidy 6 |
| 739 | Unmapped reads | Block 1, Ploidy 6 |

Figure 6:
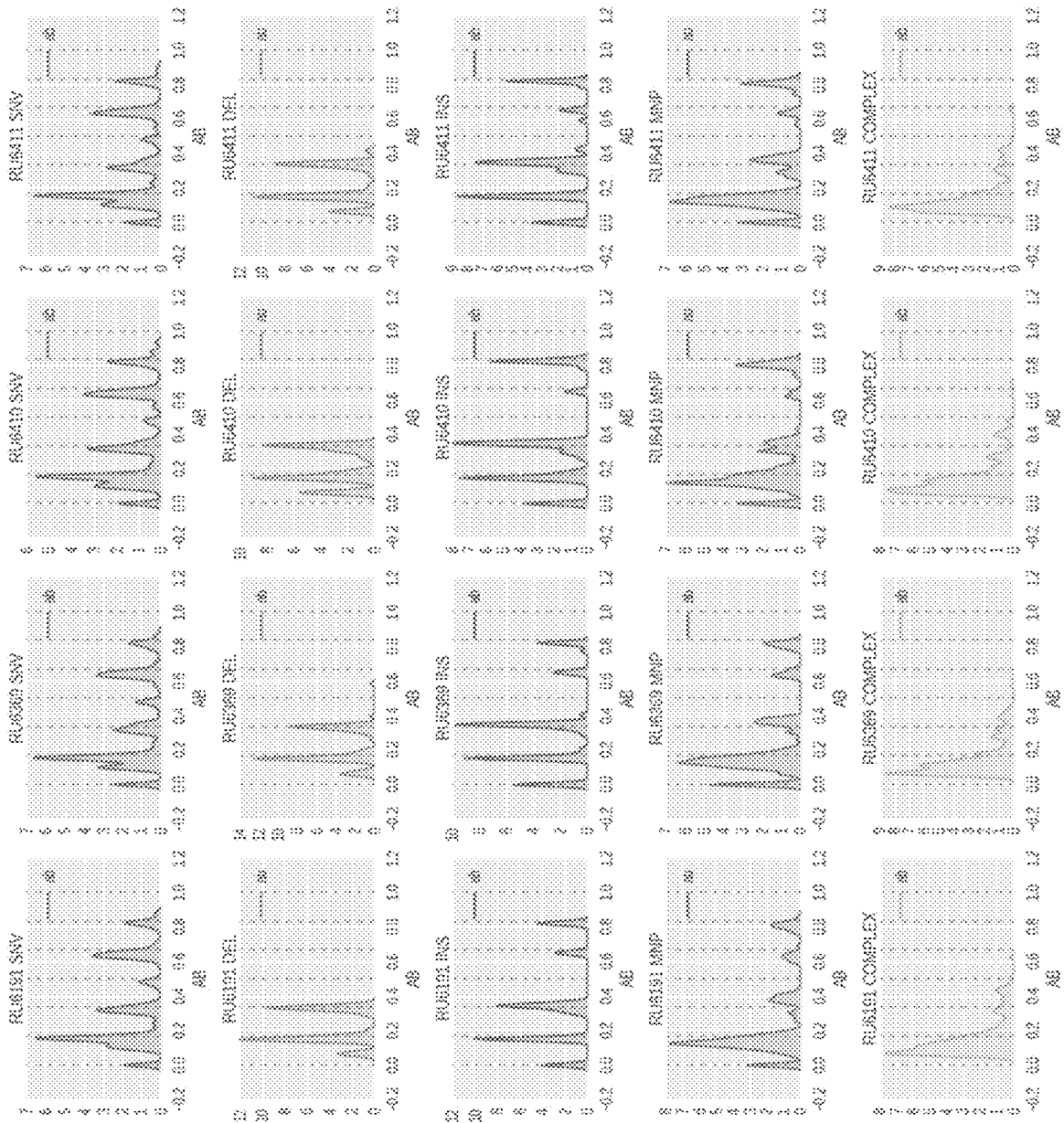
FIG. 6 shows allele balances of all variant calls (including intronic) in NEB Block1. Rows are variant type and columns are sequencing runs. A COMPLEX variant type (bottom row) is a variant call with alleles from multiple categories. Vertical dashed lines represent theoretical allele balance means for ploidy 6 calls (i.e. 0/6, 1/6, 2/6, 3/6 . . . ). The observation that the empirical AB mean that is slightly below the theoretical AB mean is likely due to capture reference bias. This plot provides strong evidence that there were in fact 6 alleles now being represented by the reads aligned to NEB Block1.

The called variants in NEB Block 1 following the reference modification were further decomposed as follows. Including intronic regions, there were 8,657 total variant calls, including 5892 SNV, 374 deletions, 360 insertions, and 875 MNVs. Histograms of allele balance for each of these variant types for each sequencing run are shown in FIG. 6. The observed allele balance modes were very close to the theoretical multiples of 1/6 predicted by the ploidy 6 calling thus providing confidence that fragments/reads from all NEB blocks were adequately captured and aligned to NEB block 1.

Further restricting attention to CDS+/−10 bp, there are only 805 total variant calls, all of them SNVs. These 805 variant calls are presented in Table 12. Variants called in >100 samples are due to the 6 fixed differences attributed to the reference genome. There are several other common variants observed, and a small number of rare (<1% in this sampling) variants observed.

Table 12 shows variant frequencies in NEB Block 1 CDS+/−10 bp. There were 119 unique samples in the 4 sequencing runs that were analyzed. The variants that occur in all or almost all 119 are reference differences in Block 2 and 3.

TABLE 12

| Chrom | Start | Stop | Ref | Alt | Count |
|---|---|---|---|---|---|
| 2 | 152458414 | 152458415 | G | A | 119 |
| 2 | 152459192 | 152459193 | C | T | 119 |
| 2 | 152459115 | 152459116 | G | A | 119 |
| 2 | 152463199 | 152463200 | C | T | 119 |
| 2 | 152457022 | 152457023 | T | C | 118 |
| 2 | 152460240 | 152460241 | G | A | 105 |
| 2 | 152457115 | 152457116 | T | G | 53 |
| 2 | 152457209 | 152457210 | C | T | 12 |
| 2 | 152465107 | 152465108 | A | C | 9 |
| 2 | 152457063 | 152457064 | C | G | 6 |
| 2 | 152461227 | 152461228 | T | A | 6 |
| 2 | 152456990 | 152456991 | T | C | 4 |
| 2 | 152457117 | 152457118 | G | C | 4 |
| 2 | 152465037 | 152465038 | G | A | 2 |
| 2 | 152461220 | 152461221 | C | T | 2 |
| 2 | 152464991 | 152464992 | T | A | 2 |
| 2 | 152457034 | 152457035 | T | C | 1 |
| 2 | 152458434 | 152458435 | A | T | 1 |
| 2 | 152457170 | 152457171 | A | G | 1 |
| 2 | 152461168 | 152461169 | C | T | 1 |
| 2 | 152463178 | 152463179 | T | C | 1 |
| 2 | 152458520 | 152458521 | T | G | 1 |

Results: Manual Inspection of all Discordant Alignments

In order to ensure that the reference modification does not negatively impact alignment and/or variant calling outside of the NEB region, the location where each read aligns was exhaustively characterized before and after the modification to the reference genome.

Greater than ~99.3% of the reads were aligned identically across 24 samples in RU3639. The discordantly mapped reads are summarized in Table 13. In this table, "alternate location" refers to any region outside of NEB Blocks 1-3. Shaded rows indicate changes that were expected due to modification of the reference genome. Red rows are less expected changes. All changes are discussed below.

TABLE 13

| Discordant reads within these samples. | |
|---|---|
| Difference Class | Count |
| Unmapped -> Block 1 | 5841453 |
| Blocks 2-3 -> Block 1 | 1185830 |
| Same Alternate Location, Different Flags | 4144 |
| Unmapped -> Between Block 1 and Blocks 2-3 | 2885 |
| Blocks 2-3 -> Unmapped | 692 |
| Blocks 2-3 -> Alternate Location | 412 |
| Alternate Location -> Unmapped | 309 |
| Unmapped -> Alternate Location | 280 |
| Different Alternate Locations | 62 |
| Alternte Location -> Block 1 | 2 |

Unmapped->Block 1 (5,841,453 reads): As expected, reads which were previously unmapped because they aligned ambiguously to 2 or more repeat blocks are now being aligned to Block 1.

Blocks 2-3->Block 1 (1,185,830 reads): Reads that were previously aligned to Blocks 2-3, due to fixed differences, are now being aligned to Block 1.

Same Alternate Location, Different Flags (4,144 reads): These reads were aligned to exactly the same region outside of NEB, but had different BAM flags set. The difference in BAM flags is due to a change in the read's mate alignment, duplicate status, or proper pair status.

Unmapped->Between Block 1 and Blocks 2-3 (2,885 reads): These reads were previously unmapped, and then mapped to the intronic region between Repeat Block 1 and Repeat Blocks 2-3.

Blocks 2-3->Unmapped (692): These reads are almost all mapped to the edge of repeat Block 3. They do not get mapped to Block 1, because their pair is uniquely mapped to a region upstream of exon 105 (i.e. not Block 1 or Block 2).

Blocks 2-3->Alternate Location (412 reads): These reads were uniquely mapped in Repeat Block 2-3 and are now mapped to some other part of the genome. There are several alternate locations on other chromosomes that have enough sequence homology that they are now sometimes recruiting these reads.

Alternate Location->Unmapped (309): These reads were originally mapped to a handful of different places on the genome, and are now unmapped. It is presumed that these regions have sequence homology to Blocks 1-3 but the exact mechanism is unclear. Because this category only represents a few reads per sample we do not believe it is cause for concern.

Unmapped->Alternate Location (280 reads): These are reads with mate previously anchored to an alternate location; removing Blocks 2-3 caused the read to now be aligned as a proper pair (within the expected insert size).

Different alternate location (62 reads): These reads didn't follow much of a pattern, were scattered around the genome and generally not properly paired.

Alternate Location->Block 1 (2 reads): Two unpaired reads in an alternate location that are now being aligned to Block 1 as a proper pair.

Overall, of the ~0.7% of total reads that were discordantly mapped, all but a vanishingly small fraction are expected due to the reference modification, and behaved as desired. The remaining reads represent the typical minor modifications that occur when altering the reference, and do not impact the variant calls (data not shown).

Results: Clinical Validation

For the purposes of this validation the following operational definitions are used:

True positive (TP)—called variant (by NGS) agrees with a known variant at this position based on results from another CLIA-approved laboratory.

True negative (TN)—Result is negative and there is no expectation of a variant.

False positive (FP)—called variant (by NGS) does not agree with the known variant status at this location False negative (FN)—Result is negative and the expected call is a variant.

With these definitions, sensitivity, specificity, and false discovery rate were calculated according to:

Sensitivity=#TP/(#TP+#FN)*100. This is a measure of the test's ability to correctly identify a known variant. Acceptance criterion is ≥95%.

Specificity=#TN/(#TN+#FP)*100. A measure of the test's ability to correctly identify a negative result (no variation). Acceptance criterion is ≥99%.

False Discovery Rate (FDR)=#FP/(#TP+#FP)*100. A measure of the test's error rate, which is inversely correlated with the positive predictive value (PPV). FDR is calculated as 1-PPV. The PPV of a test is the ability to correctly predict a positive result (TP/(TP+FP)). Acceptance criterion is <1%.

TABLE 14

|  |  | Gold Standard | |
| --- | --- | --- | --- |
|  |  | Gold Standard Positive | Gold Standard Negative |
| WGS outcome | WGS Positive | True Positive (TP) | False Positive (FP) |
|  | WGS Negative | False Negative (FN) | True Negative (TN) |
|  |  | Sensitivity = Σ True Positive/ Σ Condition Positive | Specificity = Σ True Negative/ Σ Condition Negative |

Samples

Two positive control samples known to contain a rare variant in the triplication are included in this validation (Table 15). In addition, 15 samples will be used to assess intrinsic variation within the triplication and data quality for negative samples (Table 10).

TABLE 15

Sample table: positive and negative controls.

| DNA | Variant Type | Sample | Variant | Gender | Zygosity |
| --- | --- | --- | --- | --- | --- |
| DNA1* | Well-characterized genome (SNVs, indels) | NA12878 | EJ-1B Baited Regions | Female | N/A |
| DNA2* | SNV (canonical splice change) | IB37397 | NF1: NM_000267.3:c.1855G>A | Female | Het |
| DNA3* | SNV in homopolymer | IB86101 | PTEN: NM_000314.4:c.800delA | Male | Het |
| DNA4* | SNV in GC-rich area | IB55062 | MYBPC3: NM_000256.3:c.655G>C | Female | Het |
| DNA5* | Small Indel (1-4 nt) | GM00636 | GLA:c.1187delAAG | Male | Nullizygous |
| DNA6* | Medium Indel (5-10 nt) | IB65271 | KCNT: NM_02822:insGTGCCCC | Male | Het |
| DNA7* | Large Indel (>10 nt) | NA21931 | FBN1: c.1187del17 | Female | Het |
| DNA8* | CNV single-exon deletion | NA23648 | MECP2: exon 4 del | Female | Het |
| DNA9* | CNV multi-exon deletion | NA04372 | GALC: exons 11-17 del | Male | Het |
| DNA10* | CNV single-exon duplication | NA23159 | DMD: exon 17 dup | Male | Het |
| DNA11* | CNV multi-exon duplication | NA23127 | DMD: exons 27-28 dup | Male | Het |
| DNA12* | Complex (Haplotype) | NA23650 | RYR1: c.7463_7475del13; C.1201C>T | Female | Compound Het |
| DNA13* | FKTN homopolymer | LS34701 | FKTN: NM_006371.2:c.1167insA | Female | Het |
| DNA14* | FKTN insertion | LS32949 | NM_006731.2:c.*4392_*4393insAB185332.1 | Male | Hom |
| DNA15* | PCCB | LS32956 | NM_000532.4:c.1218_1231del14ins12 | Female | Het |
| DNA16 | NEB exon 82 | LS34703 | NM_001271208.1 c.12503delT | Male | Het |
| DNA17 | NEB exon 83 | LS34704 | NM_001271208.1 c.12602T>C | Male | Het |

*Using these samples to evaluate intrinsic variants.

Table 16. Run schema for samples. DNA16 and DNA17 are each run as both inter- and intra-run triplicates. In this schema, DNA16=NM_001271208.1: c.12503delT and DNA17=NM_001271208.1: c.12602T>C.

TABLE 16

| Run #1 | Run #2 | Run #3 |
|--------|--------|--------|
| DNA16 | DNA17 | DNA16 |
| DNA16 | DNA17 | DNA17 |
| DNA16 | DNA17 | DNA3 |
| DNA17 | DNA16 | DNA3 |
| DNA1 | DNA1 | DNA3 |
| DNA1 | DNA2 | DNA1 |
| DNA1 | DNA2 | DNA2 |
| DNA2 | DNA2 | — |
| DNA3 | DNA3 | — |

Sensitivity

Variant calls were be generated for samples 1-17 within the reportable range of the assay. This will generate 104 variant calls in total consisting of 102 SNP calls, (Samples 1-17, intrinsic variants), and 2 pathogenic variant calls (samples 16 and 17).

Specificity

Sequence data will be obtained for samples 1-17 and compared to reference sequence at all loci, and calculated as described. All loci will be treated as independent observations.

Reproducibility/Precision

To assess inter-run reproducibility, two positive and negative control samples (chosen from samples 1-5, Table 15) will be run in triplicate across sequencing runs. To assess intra-run reproducibility, two positive and negative control samples (chosen from samples 1-15, Table 15) will be run in triplicate within an individual sequencing run.

PPV and False Discovery Rate

To assess false-discovery rate we will compare our variant calls to the gold standard calls for the same sample in a total of 17 DNA samples, across all loci. PPV and FDR (1-PPV) were calculated as previously described.

Acceptance Criteria

As per ACMG as well as CDC recommendations (Rehm et. al. Genetics in Medicine, Gargis et al., 2012), we have provided the following performance metrics: accuracy, precision, analytical sensitivity and specificity. In addition, false discovery rate (FDR) is provided as a measure of the positive predictive value of our test.

Data Analysis and Results
Accuracy

TABLE 17

Pathogenic NEB variants detection

| Variant | Location | Accuracy |
|---------|----------|----------|
| NM_001271208.1 c.12503delT | chr2: 152465017 | 100% (5/5) |
| NM_001271208.1 c.12602T>C | chr2: 152464055 | 100% (5/5) |

TABLE 18

Intrinsic Variant detection

| Variant | Location | Accuracy |
|---------|----------|----------|
| Ivar1 | chr2: 152457023 | 90/90 |
| Ivar2 | chr2: 152458415 | 90/90 |
| Ivar3 | chr2: 152459116 | 90/90 |
| Ivar4 | chr2: 152459193 | 90/90 |
| Ivar5 | chr2: 152460241 | 90/90 |
| Ivar6 | chr2: 152463200 | 90/90 |

Summary

We observed 100% accuracy for both rare variants and intrinsic variants.

Precision

TABLE 19

Rare variant reproducibility (DNA16)

| Sample | Run | Type | Call | Allele Balance |
|--------|-----|------|------|----------------|
| XE97390 | RU6544 | Inter/Intra | CA > A | 0.164 |
| XE97394 | RU6544 | Intra | CA > A | 0.159 |
| XE97376 | RU6544 | Intra | CA > A | 0.160 |
| XE97625 | RU6546 | Inter | CA > A | 0.157 |
| XE98677 | RU6547 | Inter | CA > A | 0.161 |

TABLE 20

Rare variant reproducibility (DNA17)

| Sample | Run | Type | Call | Allele Balance |
|--------|-----|------|------|----------------|
| XE97586 | RU6545 | Inter/Intra | A -> G | 0.155 |
| XE97595 | RU6545 | Intra | A -> G | 0.165 |
| XE97600 | RU6545 | Intra | A -> G | 0.155 |
| XE97605 | RU6546 | Inter | A -> G | 0.114 |
| XE98693 | RU6547 | Inter | A -> G | 0.157 |

TABLE 21

Intrinsic variant reproducibility (calls and allele balance)

| ID | Sample | Run | Type | Ivar1 | Ivar2 | Ivar3 | Ivar4 | Ivar5 | Ivar6 |
|----|--------|-----|------|-------|-------|-------|-------|-------|-------|
| DNA1 | XE97375 | RU6544 | Both | T -> C (0.305) | G -> A (0.649) | G -> A (0.621) | C -> T (0.452) | G -> A (0.335) | C -> T (0.000) |
| DNA1 | XE97601 | RU6544 | Intra | T -> C (0.301) | G -> A (0.653) | G -> A (0.631) | C -> T (0.456) | G -> A (0.337) | C -> T (0.000) |
| DNA1 | XE97616 | RU6544 | Intra | T -> C (0.310) | G -> A (0.650) | G -> A (0.629) | C -> T (0.452) | G -> A (0.320) | C -> T (0.000) |
| DNA1 | XE97380 | RU6545 | Inter | T -> C (0.311) | G -> A (0.657) | G -> A (0.635) | C -> T (0.463) | G -> A (0.334) | C -> T (0.000) |
| DNA1 | XE97389 | RU6546 | Inter | T -> C (0.309) | G -> A (0.645) | G -> A (0.624) | C -> T (0.453) | G -> A (0.333) | C -> T (0.000) |
| DNA2 | XE97387 | RU6544 | Inter | T -> C (0.302) | G -> A (0.648) | G -> A (0.629) | C -> T (0.471) | Ref | C -> T (0.000) |
| DNA2 | XE97602 | RU6545 | Both | T -> C (0.314) | G -> A (0.650) | G -> A (0.645) | C -> T (0.458) | Ref | C -> T (0.000) |
| DNA2 | XE97620 | RU6545 | Intra | T -> C (0.304) | G -> A (0.659) | G -> A (0.629) | C -> T (0.459) | Ref | C -> T (0.000) |

TABLE 21-continued

Intrinsic variant reproducibility (calls and allele balance)

| ID | Sample | Run | Type | Ivar1 | Ivar2 | Ivar3 | Ivar4 | Ivar5 | Ivar6 |
|---|---|---|---|---|---|---|---|---|---|
| DNA 2 | XE97594 | RU6545 | Inter | T -> C (0.309) | G -> A (0.650) | G -> A (0.632) | C -> T (0.453) | Ref | C -> T (0.000) |
| DNA 2 | XE97582 | RU6546 | Inter | T -> C (0.309) | G -> A (0.655) | G -> A (0.629) | C -> T (0.443) | Ref | C -> T (0.000) |
| DNA 3 | XE97374 | RU6544 | Inter | T -> C (0.314) | G -> A (0.657) | G -> A (0.627) | C -> T (0.454) | G -> A (0.165) | C -> T (0.825) |
| DNA 3 | XE97584 | RU6545 | Both | T -> C (0.314) | G -> A (0.651) | G -> A (0.640) | C -> T (0.469) | G -> A (0.165) | C -> T (0.825) |
| DNA 3 | XE97613 | RU6545 | Intra | T -> C (0.312) | G -> A (0.646) | G -> A (0.637) | C -> T (0.461) | G -> A (0.162) | C -> T (0.828) |
| DNA 3 | XE97609 | RU6545 | Intra | T -> C (0.303) | G -> A (0.647) | G -> A (0.626) | C -> T (0.450) | G -> A (0.163) | C -> T (0.829) |
| DNA 3 | XE97624 | RU6546 | Inter | T -> C (0.310) | G -> A (0.648) | G -> A (0.627) | C -> T (0.465) | G -> A (0.159) | C -> T (0.823) |
| DNA 16 | XE97390 | RU6544 | Both | T -> C (0.327) | G -> A (0.657) | G -> A (0.629) | C -> T (0.445) | G -> A (0.158) | C -> T (0.831) |
| DNA 16 | XE97625 | RU6544 | Intra | T -> C (0.320) | G -> A (0.649) | G -> A (0.629) | C -> T (0.457) | G -> A (0.161) | C -> T (0.833) |
| DNA 16 | XE98677 | RU6544 | Intra | T -> C (0.314) | G -> A (0.649) | G -> A (0.628) | C -> T (0.447) | G -> A (0.158) | C -> T (0.831) |
| DNA 16 | XE97394 | RU6546 | Inter | T -> C (0.324) | G -> A (0.642) | G -> A (0.635) | C -> T (0.458) | G -> A (0.158) | C -> T (0.828) |
| DNA 16 | XE97376 | RU6547 | Inter | T -> C (0.322) | G -> A (0.644) | G -> A (0.639) | C -> T (0.447) | G -> A (0.164) | C -> T (0.829) |
| DNA 17 | XE97586 | RU6545 | Both | T -> C (0.471) | G -> A (0.650) | G -> A (0.633) | C -> T (0.625) | G -> A (0.320) | C -> T (0.833) |
| DNA 17 | XE97605 | RU6545 | Intra | T -> C (0.436) | G -> A (0.654) | G -> A (0.630) | C -> T (0.571) | G -> A (0.282) | C -> T (0.827) |
| DNA 17 | XE98693 | RU6545 | Intra | T -> C (0.476) | G -> A (0.647) | G -> A (0.618) | C -> T (0.606) | G -> A (0.328) | C -> T (0.826) |
| DNA 17 | XE97595 | RU6546 | Inter | T -> C (0.460) | G -> A (0.660) | G -> A (0.632) | C -> T (0.618) | G -> A (0.322) | C -> T (0.825) |
| DNA 17 | XE97600 | RU6547 | Inter | T -> C (0.473) | G -> A (0.654) | G -> A (0.626) | C -> T (0.615) | G -> A (0.324) | C -> T (0.833) |

Summary

We observed 100% intra and inter-run reproducibility for both rare variants and intrinsic variants.

Analytic Sensitivity

Sensitivity for detection of 6 intrinsic variants (17 samples in quintuplicate) and 2 known pathogenic variants (2 samples in quintuplicate) was determined. Sensitivity was calculated as previously described, and 95% confidence intervals were estimated using the Exact (Clopper-Pearson) method.

TABLE 22

| Analytic Sensitivity | | |
|---|---|---|
| | Positive | Negative |
| NGS POS | 95 | 0 |
| NGS NEG | 0 | 95 |

Overall analytic sensitivity: 100% (95% CI: 96.1-100%) False Discovery Rate (FDR) was 0%. False positives were not observed among the known pathogenic intrinsic variants.

Conclusion

NEB contains a triplicated sequence (8.2 kb of genomic sequence spanning 8 exons with high homology (99%) which complicates sequencing of the region (FIG. 1). This triplicated sequence is not polymorphic, however rare sequence changes in the triplicated region may be pathogenic for nemaline myopathy (Donner et al). The exact genomic location of a variant with regards to repeat 1, 2, or 3 is not required for clinical reporting. By removing/masking Blocks 2-3, we're able to recruit relevant reads to Block 1, model the data in that region as if there are 6 alleles present, and accurately detect variants. A close inspection of data has demonstrated that we are able to accurately call variants within NEB Blocks 1-3 without adversely affecting other areas of the genome.

Our validation set included 4 clinical samples, 12 non-invitae sourced samples and the well-characterized cell line NA12878 (Table 15). In this study we confirm with 100% sensitivity, and 100% reproducibility our ability to detect known pathogenic variants and intrinsic variants at 1/6 allele frequency, which serves as a proxy for SNV event detection.

References

Complete genomic structure of the human nebulin gene and identification of alternatively spliced transcripts. Donner et al. EJHG. 2004. 12:744.

Assuring the quality of next-generation sequencing in clinical laboratory practice. Gargis et al. Nature Biotechnology. 2012. 30:1033.

ACMG clinical laboratory standards for next-generation sequencing. Rehm et al. Genetics in Medicine. 2013. 15.

Example 5

Examples of Embodiments

A1. A non-transitory computer-readable storage medium with an executable program stored thereon, which program is configured to instruct a microprocessor to:

(a) map sequence reads to a modified reference genome comprising a gene of interest and at least one counterpart gene of the gene of interest, wherein 1) the at least one counterpart gene of the modified reference genome is substantially altered, 2) the sequence reads are obtained from a sample obtained from a diploid subject using a massively parallel sequencing method, and 3) the sequence reads obtained from the gene of interest and the at least one counterpart gene of the subject are mapped to the gene of interest of the modified reference genome, thereby providing sequence reads mapped to the gene of interest of the modified reference genome; and (b) determine the likelihood of a presence or absence of a genetic variation in the gene of interest of the subject according to the sequence reads mapped to the gene of interest of the modified reference genome.

A2. The program of embodiment A1, wherein the microprocessor is instructed to expect at least 4 alleles for the gene of interest of the subject that map to the gene of interest of the modified reference genome.

A3. The program of embodiment A1 or A2, wherein the microprocessor is instructed to assume a ploidy of 4 for the gene of interest of the subject.

A4. The program of any one of embodiments A1 to A3, wherein the at least one counterpart gene of the subject is at least 80% identical to the gene of interest of the subject.

A5. The program of any one of embodiments A1 to A3, wherein the at least one counterpart gene of the subject is at least 90% identical to the gene of interest of the subject.

A6. The program of any one of embodiments A1 to A3, wherein the at least one counterpart gene of the subject is at least 95% identical to the gene of interest of the subject.

A7. The program of any one of embodiments A1 to A6, wherein the at least one counterpart gene of the subject is a pseudogene of the gene of interest of the subject.

A8. The program of any one of embodiments A1 to A7, wherein the at least one counterpart gene is 1 to 5 counterpart genes.

A9. The program of embodiment A8, wherein the at least one counterpart gene is 1 counterpart gene.

A10. The program of embodiment A8, wherein the at least one counterpart gene is 2 to 5 counterpart genes.

A11. The program of any one of embodiments A1 to A10, wherein each of the at least one counterpart genes of the subject comprises two alleles.

A12. The program of any one of embodiments A1 to A11, wherein the gene of interest of the subject comprises two alleles.

A13. The program of any one of embodiments A1 to A12, wherein at least 30% of nucleotides of the at least one counterpart gene of the modified reference genome are substituted with different nucleotides.

A14. The program of embodiment A13, wherein at least 50% of nucleotides of the at least one counterpart gene of the modified reference genome are substituted with different nucleotides.

A15. The program of embodiments A13, wherein the nucleotides the counterpart gene of the reference genome are substituted with ambiguous nucleotide markers.

A16. The program of any one of embodiments A1 to A15, wherein one or more nucleotides of the at least one counterpart gene of the modified reference genome are deleted.

A17. The program of any one of embodiments A1 to A16, wherein one or more nucleotides are inserted into the at least one counterpart gene of the reference genome.

A18. The program of any one of embodiments A1 to A17, wherein the sequence reads are obtained for an entire genome.

A19. The program of any one of embodiments A1 to A17, wherein the sequence reads are obtained by a chromosome-specific method or a gene-specific method.

A20. The program of any one of embodiments A1 to A19, wherein the sequence reads are obtained by a method comprising paired-end sequencing.

A21. The program of any one of embodiments A1 to A20, wherein the sequence reads are 100-200 bp in length.

A22. The program of any one of embodiments A1 to A21, wherein the sequence reads represent at least 20-fold coverage of the gene of interest.

A23. The program of any one of embodiments A1 to A22, wherein the sequence reads represent at least 50-fold coverage of the gene of interest.

A24. The program of any one of embodiments A1 to A23, wherein the gene of interest of the subject is selected from PMS2, HBA1, HBG1, HBB, SBSD, and VWF.

A25. The program of embodiment A24, wherein the gene of interest of the subject is PMS2 and the at least one counterpart gene is PMS2CL.

A26. The program of embodiment A24, wherein the gene of interest of the subject is HBA1 and the at least one counterpart gene is HBA2.

A27. The program of embodiment A24, wherein the gene of interest of the subject is HBG1 and the at least one counterpart gene is HBG2.

A28. The program of embodiment A24, wherein the gene of interest of the subject is HBB and the at least one counterpart gene is HBD.

A29. The program of embodiment A24, wherein the gene of interest of the subject is SBDS and the at least one counterpart gene is SBDSP1.

A30. The program of any one of embodiments A1 to A23, wherein the gene of interest of the subject is selected from CYP2D6, CYP21A2, PKD1 and PRSS1.

A31. The program of any one of embodiments A1 to A30, comprising determining the presence or absence of the genetic variation in (b).

A32. The program of any one of embodiments A1 to A30, further comprising determining the presence or absence of the genetic variation.

A33. The program of embodiment A32, wherein the presence or absence of the genetic variation is determined by a method comprising LR-PCR and re-sequencing.

A34. The program of any one of embodiments A1 to A33, wherein the at least one counterpart gene of the subject is not mapped to the at least one counterpart gene of the modified reference genome.

A35. The program of any one of embodiments A1 to A34, wherein the sequence reads obtained from the gene of interest and the at least one counterpart gene of the subject are mapped unambiguously to the gene of interest of the modified reference genome.

A36. The program of any one of embodiments A1 to A35, wherein the sequence reads, or a portion thereof, obtained from the gene of interest and the at least one counterpart gene of the subject are mapped to the gene of interest of the modified reference genome.

B1. A system for determining the likelihood of the presence or absence of a genetic variation in a subject, the system comprising one or more processors configured to execute computer program modules, the computer program modules comprising:

(a) a mapping module configured to map sequence reads to a modified reference genome comprising a gene of interest and at least one counterpart gene of the gene of interest where the at least one counterpart gene has a high degree of homology to the gene of interest, and wherein 1) the at least one counterpart gene of the modified reference genome is substantially altered such that sequence reads for such counterpart gene or genes map to the gene of interest instead of the counterpart genes, 2) the sequence reads are obtained from a sample obtained from a diploid subject using a massively parallel sequencing method, and 3) the sequence reads obtained from the gene of interest and the at least one counterpart gene of the subject are mapped to the gene of interest of the modified reference genome, thereby providing sequence reads mapped to the gene of interest of the modified reference genome; and (b) an outcome module configured to determine the likelihood of a presence or absence of a genetic variation in the gene of interest of the subject according to the sequence reads mapped to the gene of interest of the modified reference genome.

B1.1. The system of embodiment B1, wherein the sequence reads mapped to the gene of interest of the modified reference genome are transferred from the mapping module to the outcome module.

B2. The system of embodiment B1 or B1.1, wherein the mapping module is configured to expect at least 4 alleles of the subject that map to the gene of interest of the modified reference genome.

B3. The system of any one of embodiments B1 to B2, wherein the mapping module is instructed to expect a ploidy of 4 for the gene of interest of the subject.

B4. The system of any one of embodiments B1 to B3, wherein the at least one counterpart gene of the subject is at least 80% identical to the gene of interest of the subject.

B5. The system of any one of embodiments B1 to B3, wherein the at least one counterpart gene of the subject is at least 90% identical to the gene of interest of the subject.

B6. The system of any one of embodiments B1 to B3, wherein the at least one counterpart gene is at least 95% identical to the gene of interest B7. The system of any one of embodiments B1 to B6, wherein the at least one counterpart gene of the subject is a pseudogene of the gene of interest of the subject.

B8. The system of any one of embodiments B1 to B7, wherein the at least one counterpart gene of the subject is 1 to 5 counterpart genes.

B9. The system of embodiment B8, wherein the at least one counterpart gene of the subject is 1 counterpart gene.

B10. The system of embodiment B8, wherein the at least one counterpart gene of the subject is 2 to 5 counterpart genes.

B11. The system of any one of embodiments B1 to B10, wherein each of the at least one counterpart genes of the subject comprise two alleles.

B12. The system of any one of embodiments B1 to B11, wherein the gene of interest of the subject comprises two alleles.

B13. The system of any one of embodiments B1 to B12, wherein at least 30% of nucleotides of the at least one counterpart gene of the modified reference genome are substituted with different nucleotides.

B14. The system of embodiment B13, wherein at least 50% of nucleotides of the at least one counterpart gene of the modified reference genome are substituted with different nucleotides.

B15. The system of embodiments B13, wherein the nucleotides of the at least one counterpart gene of the modified reference genome are substituted with ambiguous nucleotide markers.

B16. The system of any one of embodiments B1 to B15, wherein one or more nucleotides of the at least one counterpart gene of the modified reference genome are deleted.

B17. The system of any one of embodiments B1 to B16, wherein one or more nucleotides are inserted into the at least one counterpart gene of the modified reference genome.

B18. The system of any one of embodiments B1 to B17, wherein the sequence reads are obtained for an entire genome.

B19. The system of any one of embodiments B1 to B17, wherein the sequence reads are obtained by a chromosome-specific method or a gene-specific method.

B20. The system of any one of embodiments B1 to B19, wherein the sequence reads are obtained by a method comprising paired-end sequencing.

B21. The system of any one of embodiments B1 to B20, wherein the sequence reads are 100-200 bp in length.

B22. The system of any one of embodiments B1 to B21, wherein the sequence reads represent at least 20-fold coverage of the gene of interest of the subject.

B23. The system of any one of embodiments B1 to B22, wherein the sequence reads represent at least 50-fold coverage of the gene of interest of the subject.

B24. The system of any one of embodiments B1 to B23, wherein the gene of interest of the subject is selected from PMS2, HBA1, HBG1, HBB, SBSD, and VWF.

B25. The system of embodiment B24, wherein the gene of interest of the subject is PMS2 and the at least one counterpart gene of the subject is PMS2CL.

B26. The system of embodiment B24, wherein the gene of interest of the subject is HBA1 and the at least one counterpart gene of the subject is HBA2.

B27. The system of embodiment B24, wherein the gene of interest of the subject is HBG1 and the at least one counterpart gene of the subject is HBG2.

B28. The system of embodiment B24, wherein the gene of interest of the subject is HBB and the at least one counterpart gene of the subject is HBD.

B29. The system of embodiment B24, wherein the gene of interest of the subject is SBDS and the at least one counterpart gene of the subject is SBDSP1.

B30. The system of any one of embodiments B1 to B23, wherein the gene of interest of the subject is selected from CYP2D6, CYP21A2, PKD1 and PRSS1.

B31. The system of any one of embodiments B1 to B30, wherein the outcome module determines the presence or absence of the genetic variation.

B32. The system of any one of embodiments B1 to B31, wherein the at least one counterpart gene of the subject is not mapped to the at least one counterpart gene of the modified reference genome.

B33. The system of any one of embodiments B1 to B32, wherein the sequence reads obtained from the gene of interest and the at least one counterpart gene of the subject in are mapped unambiguously to the gene of interest of the modified reference genome.

B34. The system of any one of embodiments B1 to B33, wherein the sequence reads, or a portion thereof, obtained from the gene of interest and the at least one counterpart gene of the subject are mapped to the gene of interest of the modified reference genome.

C1. A computer-implemented method for determining a likelihood of a presence or absence of a genetic variation in a gene of interest for a subject where the subject's genome also contains at least one counterpart gene to the gene of interest, wherein the counterpart gene has a high degree of homology to the gene of interest, comprising:

(a) mapping sequence reads to a modified reference genome comprising a gene of interest and at least one counterpart gene of the gene of interest, wherein 1) the at least one counterpart gene of the modified reference genome is substantially altered, 2) the sequence reads are obtained from a sample obtained from a diploid subject using a massively parallel sequencing method, and 3) the sequence reads obtained from the gene of interest and the at least one counterpart gene of the subject map to the gene of interest of the modified reference genome, thereby providing sequence reads mapped to the gene of interest of the modified reference genome; and (b) determining the likelihood of a presence or absence of a genetic variation in the gene of interest of the subject according to the sequence reads mapped to the gene of interest of the reference genome.

C2. The method of embodiment C1, wherein the mapping comprises an expectation that at least 4 alleles of the gene of interest of the subject map to the gene of interest of the modified reference genome.

C3. The method of embodiment C1 or C2, wherein a ploidy of at least 4 is expected for the gene of interest of the subject.

C4. The method of any one of embodiments C1 to C3, wherein the counterpart gene of the subject is at least 80% identical to the gene of interest of the subject.

C5. The method of any one of embodiments C1 to C3, wherein the counterpart gene of the subject is at least 90% identical to the gene of interest of the subject.

C6. The method of any one of embodiments C1 to C3, wherein the counterpart gene of the subject is at least 95% identical to the gene of interest of the subject.

C7. The method of any one of embodiments C1 to C6, wherein the at least one counterpart gene of the subject is a pseudogene of the gene of interest of the subject.

C8. The method of any one of embodiments C1 to C7, wherein the at least one counterpart gene of the subject is 1 to 5 counterpart genes.

C9. The method of embodiment C8, wherein the at least one counterpart gene of the subject is 1 counterpart gene.

C10. The method of embodiment C8, wherein the at least one counterpart gene of the subject is 2 to 5 counterpart genes.

C11. The method of any one of embodiments C1 to 010, wherein each of the at least one counterpart genes of the subject comprise two alleles.

C12. The method of any one of embodiments C1 to C11, wherein the gene of interest of the subject comprises two alleles.

C13. The method of any one of embodiments C1 to C12, wherein at least 30% of nucleotides of the at least one counterpart gene of the modified reference genome are substituted with different nucleotides.

C14. The method of embodiment C13, wherein at least 50% of nucleotides of the at least one counterpart gene of the modified reference genome are substituted with different nucleotides.

C15. The method of embodiments C13, wherein the nucleotides the counterpart gene of the modified reference genome are substituted with ambiguous nucleotide markers.

C16. The method of any one of embodiments C1 to C15, wherein one or more nucleotides of the at least one counterpart gene of the modified reference genome are deleted.

C17. The method of any one of embodiments C1 to C16, wherein one or more nucleotides are inserted into the at least one counterpart gene of the modified reference genome.

C18. The method of any one of embodiments C1 to C17, wherein the sequence reads are obtained for an entire genome.

C19. The method of any one of embodiments C1 to C17, wherein the sequence reads are obtained by a chromosome-specific method or a gene-specific method.

C20. The method of any one of embodiments C1 to C19, wherein the sequence reads are obtained by a method comprising paired-end sequencing.

C21. The method of any one of embodiments C1 to C20, wherein the sequence reads are 100-200 bp in length.

C22. The method of any one of embodiments C1 to C21, wherein the sequence reads represent at least 20-fold coverage of the gene of interest of the subject.

C23. The method of any one of embodiments C1 to C22, wherein the sequence reads represent at least 50-fold coverage of the gene of interest of the subject.

C24. The method of any one of embodiments C1 to C23, wherein the gene of interest of the subject is selected from PMS2, HBA1, HBG1, HBB, SBSD, and VWF.

C25. The method of embodiment C24, wherein the gene of interest of the subject is PMS2 and the at least one counterpart gene of the subject is PMS2CL.

C26. The method of embodiment C24, wherein the gene of interest of the subject is HBA1 and the at least one counterpart gene of the subject is HBA2.

C27. The method of embodiment C24, wherein the gene of interest of the subject is HBG1 and the at least one counterpart gene of the subject is HBG2.

C28. The method of embodiment C24, wherein the gene of interest of the subject is HBB and the at least one counterpart gene of the subject is HBD.

C29. The method of embodiment C24, wherein the gene of interest of the subject is SBDS and the at least one counterpart gene of the subject is SBDSP1.

C30. The method of any one of embodiments C1 to C23, wherein the gene of interest of the subject is selected from CYP2D6, CYP21A2, PKD1 and PRSS1.

C31. The method of any one of embodiments C1 to C30, comprising determining the presence or absence of the genetic variation in (b).

C32. The method of any one of embodiments C1 to C30, further comprising determining the presence or absence of the genetic variation.

C33. The method of embodiment C32, wherein the presence or absence of the genetic variation is determined by a method comprising LR-PCR and re-sequencing.

C34. The method of any one of embodiments C1 to C33, wherein reads obtained from the at least one counterpart gene of the subject do not substantially map or align to the at least one counterpart gene of the modified reference genome.

C35. The method of any one of embodiments C1 to C34, wherein the sequence reads obtained from the gene of interest and the at least one counterpart gene of the subject are mapped unambiguously to the gene of interest of the modified reference genome.

C36. The method of any one of embodiments C1 to C35, wherein the sequence reads, or a portion thereof, obtained from the gene of interest and the at least one counterpart gene of the subject are mapped to the gene of interest of the modified reference genome.

C37. The method of any one of embodiments C1 to C36, wherein the absence of the genetic variation is determined in (b).

C38. The method of any one of embodiments C1 to C37, wherein the likelihood of the presence of the genetic variation is determined in (b).

C39. The method of any one of embodiments C1 to C38, wherein a presence of the genetic variation is determined after (b).

C40. The method of any one of embodiments C1 to C39, wherein the presence of the genetic variation determined after (b) is determined by sequencing the gene of interest.

D1. The program, system or method of any one of embodiments A1 to A36, B1 to B34 or C1 to C40, wherein the gene of interest is a human gene selected the group consisting of A2M, AACS, AARSD1, ABCA10, ABCA12, ABCA3, ABCA8, ABCA9, ABCB1, ABCB10, ABCB4, ABCC11, ABCC12, ABCC6, ABCD1, ABCE1, ABCF1, ABCF2, ABT1, ACAA2, ACCSL, ACER2, ACO2, ACOT1, ACOT4, ACOT7, ACP1, ACR, ACRC, ACSBG2, ACSM1, ACSM2A, ACSM2B, ACSM4, ACSM5, ACTA1, ACTA2, ACTB, ACTG1, ACTG2, ACTN1, ACTN4, ACTR1A, ACTR2, ACTR3, ACTR3C, ACTRT1, ADAD1, ADAL, ADAM18, ADAM20, ADAM21, ADAM32, ADAMTS7, ADAMTSL2, ADAT2, ADCY5, ADCY6, ADCY7, ADGB, ADH1A, ADH1B, ADH1C, ADH5, ADORA2B, ADRBK2, ADSS, AFF3, AFF4, AFG3L2, AGAP1, AGAP10, AGAP11, AGAP4, AGAP5, AGAPE, AGAP7, AGAPE, AGAP9, AGER, AGGF1, AGK, AGPAT1, AGPAT6, AHCTF1, AHCY, AHNAK2, AHRR, AIDA, AIF1, AIM1L, AIMP2, AK2, AK3, AK4, AKAP13, AKAP17A, AKIP1, AKIRIN1, AKIRIN2, AKR1B1, AKR1B10, AKR1B15, AKR1C1, AKR1C2, AKR1C3, AKR1C4, AKR7A2, AKR7A3, AKTIP, ALDH3B1, ALDH3B2, ALDH7A1, ALDOA, ALG1, ALG10, ALG10B, ALG1L, ALG1L2, ALG3, ALKBH8, ALMS1, ALOX15, ALOX15B, ALOXE3, ALPI, ALPP, ALPPL2, ALYREF, AMD1, AMELX, AMELY, AMMECR1L, AMY1A, AMY1B, AMY1C, AMY2A, AMY2B, AMZ2, ANAPC1, ANAPC10, ANAPC15, ANKRD11, ANKRD18A, ANKRD18B, ANKRD20A1, ANKRD20A19P, ANKRD20A2, ANKRD20A3, ANKRD20A4, ANKRD30A, ANKRD30B, ANKRD36, ANKRD36B, ANKRD49, ANKS1B, ANO10, ANP32A, ANP32B, ANXA2, ANXA2R, ANXA8, ANXA8L1, ANXA8L2, AOC2, AOC3, AP1B1, AP1S2, AP2A1, AP2A2, AP2B1, AP2S1, AP3M2, AP3S1, AP4S1, APBA2, APBB1IP, APH1B, API5, AP/P, APOBEC3A, APOBEC3B, APOBEC3C, APOBEC3D, APOBEC3F, APOBEC3G, APOC1, APOL1, APOL2, APOL4, APOM, APOOL, AQP10, AQP12A, AQP12B, AQP7, AREG, AREGB, ARF1, ARF4, ARF6, ARGFX, ARHGAP11A, ARHGAP11B, ARHGAP20, ARHGAP21, ARHGAP23, ARHGAP27, ARHGAP42, ARHGAP5, ARHGAP8, ARHGEF35, ARHGEF5, ARID2, ARID3B, ARIH2, ARL14EP, ARL16, ARL17A, ARL17B, ARL2BP, ARL4A, ARL5A, ARL6IP1, ARL6IP6, ARL8B, ARMC1, ARMC10, ARMC4, ARMC8, ARMCX6, ARPC1A, ARPC2, ARPC3, ARPP19, ARSD, ARSE, ARSF, ART3, ASAH2, ASAH2B, ASB9, ASL, ASMT, ASMTL, ASNS, ASS1, ATAD1, ATAD3A, ATAD3B, ATAD3C, ATAT1, ATF4, ATF6B, ATF7IP2, ATG4A, ATM, ATMIN, ATP13A4, ATP13A5, ATP1A2, ATP1A4, ATP1B1, ATP1B3, ATP2B2, ATP2B3, ATP5A1, ATP5C1, ATP5F1, ATP5G1, ATP5G2, ATP5G3, ATP5H, ATP5J, ATP5J2, ATP5J2-PTCD1, ATP5O, ATP6AP2, ATP6VOC, ATP6V1E1, ATP6V1F, ATP6V1G1, ATP6V1G2, ATP7B, ATP8A2, ATP9B, ATXN1L, ATXN2L, ATXN7L3, AURKA, AURKAIP1, AVP, AZGP1, AZI2, B3GALNT1, B3GALT4, B3GAT3, B3GNT2, BAG4, BAG6, BAGE2, BAK1, BANF1, BANP, BCAP31, BCAR1, BCAS2, BCL2A1, BCL2L12, BCL2L2-PABPN1, BCLAF1, BCOR, BCR, BDH2, BDP1, BEND3, BET1, BEX1, BHLHB9, BHLHE22, BHLHE23, BHMT, BHMT2, BIN2, BIRC2, BIRC3, BLOC1S6, BLZF1, BMP2K, BMP8A, BMP8B, BMPR1A, BMS1, BNIP3, BOD1, BOD1L2, BOLA2, BOLA2B, BOLA3, BOP1, BPTF, BPY2, BPY2B, BPY2C, BRAF, BRCA1, BRCC3, BRD2, BRD7, BRDT, BRI3, BRK1, BRPF1, BRPF3, BRWD1, BTBD10, BTBD6, BTBD7, BTF3, BTF3L4, BTG1, BTN2A1, BTN2A2, BTN3A1, BTN3A2, BTN3A3, BTNL2, BTNL3, BTNL8, BUB3, BZW1, C10orf129, C10orf88, C11orf48, C11orf58, C11or174, C11or175, C12orf29, C12orf42, C12orf49, C12orf71, C12orf76, C14orf119, C14orf166, C14orf178, C15orf39, C15orf40, C15orf43, C16orf52, C16orf88, C17orf51, C17orf58, C17orf61, C17orf89, C17orf98, C18orf21, C18orf25, C1D, C1GALT1, C1QBP, C1QL1, C1QL4, C1QTNF9, C1QTNF9B, C1QTNF9B-AS1, C1orf100, C1orf106, C1orf114, C2, C22orf42, C22orf43, C2CD4A, C2orf6, C2orf27A, C2orf27B, C2orf69, C2orf78, C2orf81, C4A, C4B, C4BPA, C4orf27, C4orf34, C4orf46, C5orf15, C5orf43, C5orf52, C5orf60, C5orf63, C6orf10, C6orf106, C6orf136, C6orf15, C6orf203, C6orf25, C6orf47, C6orf48, C7orf63, C7orf73, C8orf46, C9orf123, C9orf129, C9orf172, C9orf57, C9orf69, C9orf78, CA14, CA15P3, CA5A, CA5B, CABYR, CACNA1C, CACNA1G, CACNA1H, CACNA1I, CACYBP, CALCA, CALCB, CALM1, CALM2, CAMSAP1, CAP1, CAPN8, CAPZA1, CAPZA2, CARD16, CARD17, CASC8, CASP1, CASP3, CASP4, CASP5, CATSPER2, CBR1, CBR3, CBWD1, CBWD2, CBWD3, CBWDS, CBWD6, CBWD7, CBX1, CBX3, CCDC101, CCDC111, CCDC121, CCDC127, CCDC14, CCDC144A, CCDC144NL, CCDC146, CCDC150, CCDC174, CCDC25, CCDC58, CCDC7, CCDC74A, CCDC74B, CCDC75, CCDC86, CCHCR1, CCL15, CCL23, CCL3, CCL3L1, CCL3L3, CCL4, CCL4L1, CCL4L2, CCNB1IP1, CCNB2, CCND2, CCNG1, CCNJ, CCNT2, CCNYL1, CCR2, CCR5, CCRL1, CCRN4L, CCT4, CCT5, CCT6A, CCT7, CCT8, CCT8L2, CCZ1, CCZ1B, CD177, CD1A, CD1B, CD1C, CD1D, CD1E, CD200R1, CD200R1L, CD209, CD276, CD2BP2, CD300A, CD300C, CD300LD, CD300LF, CD33, CD46, CD83, CD8B, CD97, CD99, CDC14B, CDC20, CDC26, CDC27, CDC37, CDC42, CDC42EP3, CDCA4, CDCA7L, CDH12, CDK11A, CDK11B, CDK2AP2, CDK5RAP3, CDK7, CDK8, CDKN2A, CDKN2AIPNL, CDKN2B, CDON, CDPF1, CDRT1, CDRT15, CDRT15L2, CDSN, CDV3, CDY1, CDY2A, CDY2B, CEACAM1, CEACAM18, CEACAM21, CEACAM3, CEACAM4, CEA CAMS, CEACAM6, CEACAM7, CEACAM8, CEL, CELA2A, CELA2B, CELA3A, CELA3B, CELSR1, CEND1, CENPC1, CENPI, CENPJ, CENPO, CEP170, CEP19, CEP192, CEP290, CEP57L1, CES1, CES2, CES5A, CFB, CFC1, CFC1B, CFH, CFHR1, CFHR2, CFHR3, CFHR4, CFHR5, CFL1, CFTR, CGB, CGB1, CGB2, CGB5, CGB7, CGB8, CHAF1B, CHCHD10, CHCHD2, CHCHD3, CHCHD4, CHD2, CHEK2, CHIA, CHMP4B, CHMP5, CHORDC1, CHP1, CHRAC1, CHRFAM7A, CHRNA2, CHRNA4, CHRNB2, CHRNB4, CHRNE, CHST5, CHST6, CHSY1, CHTF8, CIAPIN1, CIC, CIDEC, CIR1, CISD1, CISD2, CKAP2, CKMT1A, CKMT1B, CKS2, CLC, CLCN3, CLCNKA, CLCNKB, CLDN22, CLDN24, CLDN3, CLDN4, CLDN6, CLDN7, CLEC17A, CLEC18A, CLEC18B, CLEC18C, CLEC1A, CLEC1B, CLEC4G, CLEC4M, CLIC1, CLIC4, CLK2, CLK3, CLK4, CLNS1A, CMPK1, CMYA5, CNEP1R1, CNN2, CNN3, CNNM3, CNNM4, CNOT6L, CNOT7, CNTNAP3, CNTNAP3B, CNTNAP4, COA5, COBL, COIL, COL11A2, COL12A1, COL19A1, COL25A1, COL28A1, COL4A5, COL6A5, COL6A6, COMMD4, COMMD5, COPRS, COPS5, COPSE, COQ10B, CORO1A, COX10, COX17, COX20, COX5A, COX6A1, COX6B1, COX7B, COX7C, COX8C, CP, CPAMD8, CPD, CPEB1, CPSF6, CR1, CR1L, CRADD, CRB3, CRCP, CREBBP, CRHR1, CRLF2, CRLF3, CRNN, CROCC, CRTC1, CRYBB2, CRYGB, CRYGC, CRYGD, CS, CSAG1, CSAG2, CSAG3, CSDA, CSDE1, CSF2RA, CSF2RB, CSGALNACT2, CSH1, CSH2, CSHL1, CSNK1A1, CSNK1D, CSNK1E, CSNK1G2, CSNK2A1, CSNK2B, CSPG4, CSRP2, CST1, CST2, CST3, CST4, CST5, CST9, CT45A1, CT45A2, CT45A3, CT45A4, CT45A5, CT45A6, CT47A1, CT47A10, CT47A11, CT47A12, CT47A2, CT47A3, CT47A4, CT47A5, CT47A6, CT47A7, CT47A8, CT47A9, CT47B1, CTAG1A, CTAG1B, CTAG2, CTAGE1, CTAGE5, CTAGE6P, CTAGE9, CTBP2, CTDNEP1, CTDSP2, CTDSPL2, CTLA4, CTNNA1, CTNND1, CTRB1, CTRB2, CTSL1, CTU1, CUBN, CUL1, CUL7, CUL9, CUTA, CUX1, CXADR, CXCL1, CXCL17, CXCL2, CXCL3, CXCL5, CXCL6, CXCR1, CXCR2, CXorf40A, CXorf40B, CXorf48, CXorf49, CXorf49B, CXorf56, CXorf61, CYB5A, CYCS, CYP1181, CYP11B2, CYPIA1, CYP1A2, CYP21A2, CYP2A13, CYP2A6, CYP2A7, CYP2B6, CYP2C18, CYP2C19, CYP2C8, CYP2C9, CYP2D6, CYP2F1, CYP3A4, CYP3A43, CYP3A5, CYP3A7, CYP3A7-CYP3AP1, CYP46A1, CYP4A11, CYP4A22, CYP4F11, CYP4F12, CYP4F2, CYP4F3, CYP4F8, CYP4Z1, CYP51A1, CYorf17, DAP3, DAPK1, DAXX, DAZ1, DAZ2, DAZ3, DAZ4, DAZAP2, DAZL, DBF4, DCAF12L1, DCAF12L2, DCAF13, DCAF4, DCAF4L1, DCAF4L2, DCAF6, DCAF8L1, DCAF8L2, DCLRE1C, DCTN6, DCUN1D1, DCUN1D3, DDA1, DDAH2, DDB2, DDR1, DDT, DDTL, DDX10, DDX11, DDX18, DDX19A, DDX19B, DDX23, DDX26B, DDX39B, DDX3X, DDX3Y, DDX50, DDX55, DDX56, DDX6, DDX60, DDX60L, DEF8, DEFB103A, DEFB103B, DEFB104A, DEFB104B, DEFB105A, DEFB105B, DEFB106A, DEFB106B, DEFB107A, DEFB107B, DEFB108B, DEFB130, DEFB131, DEFB4A, DEFB4B, DENND1C, DENR, DEPDC1, DERL2, DESI2, DEXI, DGCR6, DGCR6L, DGKZ, DHFR, DHFRL1, DHRS2, DHRS4, DHRS4L1, DHRS4L2, DHRSX, DHX16, DHX29, DHX34, DHX40, DICER1, DIMT1, DIS3L2, DKKL1, DLEC1, DLST, DMBT1, DMRTC1, DMRTC1B, DNAH11, DNAJA1, DNAJA2, DNAJB1, DNAJB14, DNAJB3, DNAJB6, DNAJC1, DNAJC19, DNAJC24, DNAJC25-GNG10, DNAJC5, DNAJC7, DNAJC8, DNAJC9, DND1, DNM1, DOCK1, DOCK11, DOCK9, DOK1, DOM3Z, DONSON, DPCR1, DPEP2, DPEP3, DPF2, DPH3, DPM3, DPP3, DPPA2, DPPA3, DPPA4, DPPA5, DPRX, DPY19L1, DPY19L2, DPY19L3, DPY19L4, DPY30, DRAXIN, DRD5, DRG1, DSC2, DSC3, DSE, DSTN, DTD2, DTWD1, DTWD2, DTX2, DUOX1, DUOX2, DUSP12, DUSP5, DUSP8, DUT, DUXA, DYNC1I2, DYNC1LI1, DYNLT1, DYNLT3, E2F3, EBLN1, EBLN2, EBPL, ECEL1, EDDM3A, EDDM3B, EED, EEF1A1, EEF1B2, EEF1D, EEF1E1, EEF1G, EFCAB3, EFEMP1, EFTUD1, EGFL8, EGLN1, EHD1, EHD3, EHMT2, EI24, EIF1, EIF1AX, EIF2A, EIF2C1, EIF2C3, EIF2S2, EIF2S3, EIF3A, EIF3C, EIF3CL, EIF3E, EIF3F, EIF3J, EIF3L, EIF3M, EIF4A1, EIF4A2, EIF4B, EIF4E, EIF4E2, EIF4EBP1, EIF4EBP2, EIF4H, EIF5, EIF5A, EIF5A2, EIF5AL1, ELF2, ELK1, ELL2, ELMO2, EMB, EMC3, EMR1, EMR2, EMR3, ENAH, ENDOD1, ENO1, ENO3, ENPEP, ENPP7, ENSA, EP300, EP400, EPB41L4B, EPB41L5, EPCAM, EPHA2, EPHB2, EPHB3, EPN2, EPN3, EPPK1, EPX, ERCC3, ERF, ERP29, ERP44, ERVV-1, ERVV-2, ESCO1, ESF1, ESPL1, ESPN, ESRRA, ETF1, ETS2, ETV3, ETV3L, EVA1C, EVPL, EVPLL, EWSR1, EX005, EXOC8, EXOG, EXOSC3, EXOSC6, EXTL2, EYS, EZR, F5, F8A1, F8A2, F8A3, FABP3, FABP5, FAF2, FAHD1, FAHD2A, FAHD2B, FAM103A1, FAM1048, FAM108A1, FAM108C1, FAM111B, FAM115A, FAM115C, FAM120A, FAM1208, FAM127A, FAM127B, FAM127C, FAM131C, FAM133B, FAM136A, FAM149B1, FAM151A, FAM153A, FAM153B, FAM154B, FAM156A, FAM156B, FAM157A, FAM157B, FAM163B, FAM165B, FAM175A, FAM177A1, FAM185A, FAM186A, FAM18B1, FAM18B2, FAM190B, FAM192A, FAM197Y1, FAM197Y3, FAM197Y4, FAM197Y6, FAM197Y7, FAM197Y8, FAM197Y9, FAM203A, FAM203B, FAM204A, FAM205A, FAM206A, FAM207A, FAM209A, FAM209B, FAM20B, FAM210B, FAM213A, FAM214B, FAM218A, FAM21A, FAM21B, FAM21C, FAM220A, FAM22A, FAM22D, FAM22F, FAM22G, FAM25A, FAM25B, FAM25C, FAM25G, FAM27E4P, FAM32A, FAM35A, FAM3C, FAM45A, FAM47A, FAM47B, FAM47C, FAM47E-STBD1, FAM58A, FAM60A, FAM64A, FAM72A, FAM72B, FAM72D, FAM76A, FAM83G, FAM86A, FAM86B2, FAM86C1, FAM89B, FAM8A1, FAM90A1, FAM91A1, FAM92A1, FAM96A, FAM98B, FAM9A, FAM9B, FAM9C, FANCD2, FANK1, FAR1, FAR2, FARP1, FARSB, FASN, FASTKD1, FAT1, FAU, FBLIM1, FBP2, FBRSL1, FBXL12, FBXO25, FBXO3, FBXO36, FBXO44, FBXO6, FBXW10, FBXW11, FBXW2, FBXW4, FCF1, FCGBP, FCGR1A, FCGR2A, FCGR2B, FCGR3A, FCGR3B, FCN1, FCN2, FCRL1, FCRL2, FCRL3, FCRL4, FCRL5, FCRL6, FDPS, FDX1, FEM1A, FEV1, FER, FFAR3, FGD5, FGF7, FGFR1OP2, FH, FHL1, FIGLA, FKBP1A, FKBP4, FKBP6, FKBP8, FKBP9, FKBPL, FLG, FLG2, FLI1, FLJ44635, FLNA, FLNB, FLNC, FLOT1, FLT1, FLYWCH1, FMN2, FN3K, FOLH1, FOLH1B, FOLR1, FOLR2, FOLR3, FOSL1, FOXA1, FOXA2, FOXA3, FOXD1, FOXD2, FOXD3, FOXD4L2, FOXD4L3, FOXD4L6, FOXF1, FOXF2, FOXH1, FOXN3, FOXO1, FOXO3, FPR2, FPR3, FRAT2, FREM2, FRG1, FRG2, FRG2B, FRG2C, FRMD6, FRMD7, FRMD8, FRMPD2, FSCN1, FSIP2, FTH1, FTHL17, FTL, FTO, FUNDC1, FUNDC2, FUT2, FUT3, FUT5, FUT6, FXN, FXR1, FZD2, FZD5, FZD8, G2E3, G3BP1, GABARAP, GABARAPL1, GABBR1, GABPA, GABRP, GABRR1, GABRR2, GAGE1, GAGE10, GAGE12C, GAGE12D, GAGE12E, GAGE12F, GAGE12G, GAGE12H, GAGE12I, GAGE12J, GAGE13, GAGE2A, GAGE2B, GAGE2C, GAGE2D, GAGE2E, GAPDH, GAR1, GATS, GATSL1, GATSL2, GBA, GBP1, GBP2, GBP3, GBP4, GBP5, GBP6, GBP7, GCAT, GCDH, GCNT1, GCOM1, GCSH, GDI2, GEMIN7, GEMIN8, GFRA2, GGCT, GGT1, GGT2, GGT5, GGTLC1, GGTLC2, GH1, GH2, GINS2, GJA1, GJC3, GK, GK2, GLB1L2, GLB1L3, GLDC, GLOD4, GLRA1, GLRA4, GLRX, GLRX3, GLRX5, GLTP, GLTSCR2, GLUD1, GLUL, GLYATL1, GLYATL2, GLYR1, GM2A, GMCL1, GMFB, GMPS, GNA11, GNAQ, GNAT2, GNG10, GNG5, GNGT1, GNL1, GNL3, GNL3L, GNPNAT1, GOLGA2, GOLGA4, GOLGA5, GOLGA6A, GOLGA6B, GOLGA6C, GOLGA6D, GOLGA6L1, GOLGA6L10, GOLGA6L2, GOLGA6L3, GOLGA6L4, GOLGA6L6, GOLGA6L9, GOLGA7, GOLGA8H, GOLGA8J, GOLGA8K, GOLGA8O, GON4L, GOSR1, GOSR2, GOT2, GPAA1, GPANK1, GPAT2, GPATCH8, GPC5, GPCPD1, GPD2, GPHN, GPN1, GPR116, GPR125, GPR143, GPR32, GPR89A, GPR89B, GPR89C, GPS2, GPSM3, GPX1, GPX5, GPX6, GRAP, GRAPL, GRIA1, GRIA3, GRIA4, GRK6, GRM5, GRM8, GRPEL2, GSPT1, GSTA1, GSTA2, GSTA3, GSTA5, GSTM1, GSTM2, GSTM4, GSTM5, GSTO1, GSTT1, GSTT2, GSTT2B, GTF2A1L, GTF2H1, GTF2H2, GTF2H2C, GTF2H4, GTF2I, GTF2IRD1, GTF2IRD2, GTF2IRD2B, GTF3C6, GTPBP6, GUSB, GXYLT1, GYG1, GYG2, GYPA, GYPB, GYPE, GZMB, GZMH, H1FOO, H2AFB1, H2AFB2, H2AFB3, H2AFV, H2AFX, H2AFZ, H2BFM, H2BFWT, H3F3A, H3F3B, H3F3C, HADHA, HADHB, HARS, HARS2, HAS3, HAUS1, HAUS4, HAUS6, HAVCR1, HAX1, HBA1, HBA2, HBB, HBD, HBG1, HBG2, HBS1L, HBZ, HCAR2, HCAR3, HCN2, HCN3, HCN4, HDAC1, HDGF, HDHD1, HEATR7A, HECTD4, HERC2, HIATL1, HIBCH, HIC1, HIC2, HIGD1A, HIGD2A, HINT1, HIST1H1B, HIST1H1C, HIST1H1D, HIST1H2AA, HIST1H2AB, HIST1H2AC, HIST1H2AD, HIST1H2AE, HIST1H2AG, HIST1H2AH, HIST1H2AI, HIST1H2AL, HIST1H2BB, HIST1H2BD, HIST1H2BE, HIST1H2BF, HIST1H2BH, HIST1H2BI, HIST1H2BK, HIST1H2BM, HIST1H2BN, HIST1H2B0, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AB, HIST2H2AC, HIST2H2BE, HIST2H2BF, HIST2H3A, HIST2H3D, HIST2H4A, HIST2H4B, HIST3H2BB, HIST3H3, HIST4H4, HK2, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB5, HLA-E, HLA-F, HLA-G, HMGA1, HMGB1, HMGB2, HMGB3, HMGCS1, HMGN1, HMGN2, HMGN3, HMGN4, HMX1, HMX3, HNRNPA1, HNRNPA3, HNRNPAB, HNRNPC, HNRNPCL1, HNRNPD, HNRNPF, HNRNPH1, HNRNPH2, HNRNPH3, HNRNPK, HNRNPL, HNRNPM, HNRNPR, HNRNPU, HNRPDL, HOMER2, HORMAD1, HOXA2, HOXA3, HOXA6, HOXA7, HOXB2, HOXB3, HOXB6, HOXB7, HOXD3, HP, HPR, HPS1, HRG, HS3ST3A1, HS3ST3B1, HS6ST1, HSD1781, HSD17812, HSD1784, HSD1786, HSD1787, HSD1788, HSD3B1, HSD3B2, HSF2, HSFX1, HSFX2, HSP9OAA1, HSP90AB1, HSP90B1, HSPA14, HSPA1A, HSPA1B, HSPA1L, HSPA2, HSPA5, HSPA6, HSPA8, HSPA9, HSPB1, HSPD1, HSPE1, HSPE1-MOB4, HSPG2, HTN1, HTN3, HTR3C, HTR3D, HTR3E, HTR7, HYDIN, HYPK, IARS, ID2, IDH1, IDI1, IDS, IER3, IFI16, IFIH1, IFIT1, IFIT1B, IFIT2, IFIT3, IFITM3, IFNA1, IFNA10, IFNA14, IFNA16, IFNA17, IFNA2, IFNA21, IFNA4, IFNA5, IFNA6, IFNA7, IFNA8, IFT122, IFT80, IGBP1, IGF2BP2, IGF2BP3, IGFL1, IGFL2, IGFN1, IGLL1, IGLL5, IGLONS, IGSF3, IHH, 1K, IKBKG, IL17RE, 1L18, IL28A, IL28B, IL29, IL32, IL3RA, ILEST, IL9R, IMMP1L, IMMT, IMPA1, IMPACT, IMPDH1, ING5, INIP, INTS4, INTS6, IPMK, 1P07, IPPK, IQCB1, IREB2, IRX2, IRX3, IRX4, IRX5, IRX6, ISCA1, ISCA2, ISG20L2, ISL1, ISL2, IST1, ISY1-RAB43, ITFG2, ITGAD, ITGAM, ITGAX, ITGB1, ITGB6, ITIH6, ITLN1, ITLN2, ITSN1, KAL1, KANK1, KANSL1, KARS, KAT7, KATNBL1, KBTBD6, KBTBD7, KCNA1, KCNAS, KCNA6, KCNC1, KCNC2, KCNC3, KCNH2, KCNH6, KCNJ12, KCNJ4, KCNMB3, KCTD1, KCTDS, KCTD9, KDELC1, KDM5C, KDM5D, KDM6A, KHDC1, KHDC1L, KHSRP, KIAA0020, KIAA0146, KIAA0494, KIAA0754, KIAA0895L, KIAA1143, KIAA1191, KIAA1328, KIAA1377, KIAA1462, KIAA1549L, KIAA1551, KIAA1586, KIAA1644, KIAA1671, KIAA2013, KIF1C, KIF27, KIF4A, KIF4B, KIFC 1, KIR2DL1, KIR2DL3, KIR2DL4, KIR2DS4, KIR3DL1, KIR3DL2, KIR3DL3, KLF17, KLF3, KLF4, KLF7, KLF8, KLHL12, KLHL13, KLHL15, KLHL2, KLHLS, KLHL9, KLK2, KLK3, KLRC1, KLRC2, KLRC3, KLRC4, KNTC1, KPNA2, KPNA4, KPNA7, KPNB1, KRAS, KRT13, KRT14, KRT15, KRT16, KRT17, KRT18, KRT19, KRT25, KRT27, KRT28, KRT3, KRT31, KRT32, KRT33A, KRT33B, KRT34, KRT35, KRT36, KRT37, KRT38, KRT4, KRT5, KRT6A, KRT6B, KRT6C, KRT71, KRT72, KRT73, KRT74, KRT75, KRT76, KRT8, KRT80, KRT81, KRT82, KRT83, KRT85, KRT86, KRTAP1-1, KRTAP1-3, KRTAP1-5, KRTAP10-10, KRTAP10-11, KRTAP10-12, KRTAP10-2, KRTAP10-3, KRTAP10-4, KRTAP10-7, KRTAP10-9, KRTAP12-1, KRTAP12-2, KRTAP12-3, KRTAP13-1, KRTAP13-2, KRTAP13-3, KRTAP13-4, KRTAP19-1, KRTAP19-5, KRTAP2-1, KRTAP2-2, KRTAP2-3, KRTAP2-4, KRTAP21-1, KRTAP21-2, KRTAP23-1, KRTAP3-2, KRTAP3-3, KRTAP4-12, KRTAP4-4, KRTAP4-6, KRTAP4-7, KRTAP4-9, KRTAP5-1, KRTAP5-10, KRTAP5-3, KRTAP5-4, KRTAP5-6, KRTAP5-8, KRTAP5-9, KRTAP6-1, KRTAP6-2, KRTAP6-3, KRTAP9-2, KRTAP9-3, KRTAP9-6, KRTAP9-8, KRTAP9-9, L1TD1, LAGE3, LAIR1, LAIR2, LAMTOR3, LANCL3, LAP3, LAPTM4B, LARP1, LARP1B, LARP4, LARP7, LCE1A, LCE1B, LCE1C, LCE1D, LCE1E, LCE1F, LCE2A, LCE2B, LCE2C, LCE2D, LCE3C, LCE3D, LCE3E, LCMT1, LCN1, LDHA, LDHAL6B, LDHB, LEFTY1, LEFTY2, LETM1, LGALS13, LGALS14, LGALS16, LGALS7, LGALS7B, LGALS9, LGALS9B, LGALS9C, LGMN, LGR6, LHB, LILRA1, LILRA2, LILRA3, LILRA4, LILRA5, LILRA6, LILRB1, LILRB2, LILRB3, LILRB4, LILRB5, LIMK2, LIMS1, LIN28A, LIN28B, LIN54, LLPH, LMLN, LNX1, LOC100129083, LOC100129216, LOC100129307, LOC100129636, LOC100130539, LOC100131107, LOC100131608, LOC100132154, LOC100132202, LOC100132247, LOC100132705, LOC100132858, LOC100132859, LOC100132900, LOC100133251, LOC100133267, LOC100133301, LOC100286914, LOC100287294, LOC100287368, LOC100287633, LOC100287852, LOC100288332, LOC100288646, LOC100288807, LOC100289151, LOC100289375, LOC100289561, LOC100505679, LOC100505767, LOC100505781, LOC100506248, LOC100506533, LOC100506562, LOC100507369, LOC100507607, LOC100652777, LOC100652871, LOC100652953, LOC100996256, LOC100996259, LOC100996274, LOC100996301, LOC100996312, LOC100996318, LOC100996337, LOC100996356, LOC100996369, LOC100996394, LOC100996401, LOC100996413, LOC100996433, LOC100996451, LOC100996470, LOC100996489, LOC100996541, LOC100996547, LOC100996567, LOC100996574, LOC100996594, LOC100996610, LOC100996612, LOC100996625, LOC100996631, LOC100996643, LOC100996644, LOC100996648, LOC100996675, LOC100996689, LOC100996701, LOC100996702, LOC377711, LOC388849, LOC391322, LOC391722, LOC401052, LOC402269, LOC440243, LOC440292, LOC440563, L00554223, LOC642441, LOC642643, LOC642778, LOC642799, LOC643802, LOC644634, LOC645202, LOC645359, LOC646021, LOC646670, LOC649238, LOC728026, LOC728715, LOC728728, LOC728734, LOC728741, LOC728888, LOC729020, LOC729159, LOC729162, LOC729264, LOC729458, LOC729574, LOC729587, LOC729974, LOC730058, LOC730268, LOC731932, LOC732265, LONRF2, LPA, LPCAT3, LPGAT1, LRP5, LRP5L, LRRC16B, LRRC28, LRRC37A, LRRC37A2, LRRC37A3, LRRC37B, LRRC57, LRRC59, LRRC8B, LRRFIP1, LSM12, LSM14A, LSM2, LSM3, LSP1, LTA, LTB, LUZP6, LY6G5B, LY6G5C, LY6G6C, LY6G6D, LY6G6F, LYPLA1, LYPLA2, LYRM2, LYRM5, LYST, LYZL1, LYZL2, LYZL6, MAD1L1, MAD2L1, MAGEA10-MAGEA5, MAGEA11, MAGEA12, MAGEA2B, MAGEA4, MAGEA5, MAGEA6, MAGEA9, MAGEB2, MAGEB4, MAGEB6, MAGEC1, MAGEC3, MAGED1, MAGED2, MAGED4, MAGED4B, MAGIX, MALL, MAMDC2, MAN1A1, MAN1A2, MANBAL, MANEAL, MAP1LC3B, MAP1LC3B2, MAP2K1, MAP2K2, MAP2K4, MAP3K13, MAP7, MAPK1IP1L, MAPK6, MAPK8IP1, MAPRE1, MAPT, MARC1, MARC2, MAS1L, MASP1, MAST1, MAST2, MAST3, MAT2A, MATR3, MBD3L2, MBD3L3, MBD3L4, MBD3L5, MBLAC2, MCCD1, MCF2L2, MCFD2, MCTS1, MDC 1, ME1, ME2, MEAF6, MED13, MED15, MED25, MED27, MED28, MEF2A, MEF2BNB, MEIS3, MEMO1, MEP1A, MESP1, MEST, METAP2, METTL1, METTL15, METTL21A, METTL21D, METTL2A, METTL2B, METTL5, METTL7A, METTLE, MEX3B, MEX3D, MFAP2, MFF, MFN1, MFSD2B, MGAM, MICA, MICB, MINOS1, MIPEP, MK167, MKI67IP, MKNK1, MKRN1, MLF1IP, MLL3, MLLT10, MLLT6, MMADHC, MMP10, MMP23B, MMP3, MOB4, MOCS1, MOCS3, MOG, MORF4L1, MORF4L2, MPEG1, MPHOSPH10, MPHOSPH8, MPO, MPP7, MPPE1, MPRIP, MPV17L, MPZL1, MR1, MRC1, MRE11A, MRFAP1, MRFAP1L1, MRGPRX2, MRGPRX3, MRGPRX4, MRPL10, MRPL11, MRPL19, MRPL3, MRPL32, MRPL35, MRPL36, MRPL45, MRPL48, MRPL50, MRPL51, MRPS10, MRPS16, MRPS17, MRPS18A, MRPS18B, MRPS18C, MRPS21, MRPS24, MRPS31, MRPS33, MRPS36, MRPS5, MRRF, MRS2, MRTO4, MS4A4A, MS4A4E, MS4A6A, MS4A6E, MSANTD2, MSANTD3, MSANTD3-TMEFF1, MSH5, MSL3, MSN, MST1, MSTO1, MSX2, MT1A, MT1B, MT1E, MT1F, MT1G, MT1H, MT1M, MT1X, MT2A, MTAP, MTCH1, MTFR1, MTHFD1, MTHFD1L, MTHFD2, MTIF2, MTIF3, MTMR12, MTMR9, MTRF1L, MTRNR2L1, MTRNR2L5, MTRNR2L6, MTRNR2L8, MTX1, MUC12, MUC16, MUC19, MUC20, MUC21, MUC22, MUC5B, MUC6, MX1, MX2, MXRA5, MXRA7, MYADM, MYEOV2, MYH1, MYH11, MYH13, MYH2, MYH3, MYH4, MYH6, MYH7, MYH8, MYH9, MYL12A, MYL12B, MYL6, MYL6B, MYLK, MYO5B, MZT1, MZT2A, MZT2B, NAA40, NAALAD2, NAB1, NACA, NACA2, NA CAD, NACC2, NAGK, NAIP, NAMPT, NANOG, NANOGNB, NANP, NAP1L1, NAP1L4, NAPEPLD, NAPSA, NARG2, NARS, NASP, NAT1, NAT2, NAT8, NAT8B, NBAS, NBEA, NBEAL1, NBPF1, NBPF10, NBPF11, NBPF14, NBPF15, NBPF16, NBPF4, NBPF6, NBPF7, NBPF9, NBR1, NCAPD2, NCF1, NCOA4, NCOA6, NCOR1, NCR3, NDEL1, NDST3, NDST4, NDUFA4, NDUFA5, NDUFA9, NDUFAF2, NDUFAF4, NDUFB1, NDUFB3, NDUFB4, NDUFB6, NDUFB8, NDUFB9, NDUFS5, NDUFV2, NEB, NEDD8, NEDD8-MDP1, NEFH, NEFM, NEIL2, NEK2, NETO2, NEU1, NEUROD1, NEUROD2, NF1, NFE2L3, NFIC, NFIX, NFKBIL1, NFYB, NFYC, NHLH1, NHLH2, NHP2, NHP2L1, NICN1, NIF3L1, NIP7, NIPA2, NIPAL1, NIPSNAP3A, NIPSNAP3B, NKAP, NKX1-2, NLGN4X, NLGN4Y, NLRP2, NLRP5, NLRP7, NLRP9, NMD3, NME2, NMNAT1, NOB1, NOC2L, NOL11, NOLC1, NOMO1, NOMO2, NOMO3, NONO, NOP10, NOP56, NOS2, NOTCH2, NOTCH2NL, NOTCH4, NOX4, NPAP1, NPEPPS, NPIP, NPIPL3, NPM1, NPSR1, NR2F1, NR2F2, NR3C1, NRBF2, NREP, NRM, NSA2, NSF, NSFL1C, NSMAF, NSRP1, NSUN5, NT5C3, NT5DC1, NTM, NTPCR, NUBP1, NUDC, NUDT10, NUDT11, NUDT15, NUDT16, NUDT19, NUDT4, NUDT5, NUFIP1, NUP210, NUP35, NUP50, NUS1, NUTF2, NXF2, NXF2B, NXF3, NXF5, NXPE1, NXPE2, NXT1, OAT, OBP2A, OBP2B, OBSCN, OCLN, OCM, OCM2, ODC1, OFD1, OGDH, OGDHL, OGFOD1, OGFR, OLA1, ONECUT1, ONECUT2, ONECUT3, OPCML, OPN1LW, OPN1MW, OPN1MW2, OR10A2, OR10A3, OR10A5, OR10A6, OR10C1, OR10G2, OR10G3, OR10G4, OR10G7, OR10G8, OR10G9, OR1OH1, OR1OH2, OR1OH3, OR1OH4, OR1OH5, OR10J3, OR10J5, OR10K1, OR10K2, OR10Q1, OR11A1, OR11G2, OR11H1, OR11H12, OR11H2, OR12D2, OR12D3, OR13C2, OR13C4, OR13C5, OR13C9, OR13D1, OR14J1, OR1A1, OR1A2, OR1D2, OR1D5, OR1E1, OR1E2, OR1F1, OR1J1, OR1J2, OR1J4, OR1L4, OR1L6, OR1M1, OR1S1, OR1S2, OR2A1, OR2A12, OR2A14, OR2A2, OR2A25, OR2A4, OR2A42, OR2A5, OR2A7, OR2AG1, OR2AG2, OR2B2, OR2B3, OR2B6, OR2F1, OR2F2, OR2H1, OR2H2, OR2J2, OR2J3, OR2L2, OR2L3, OR2L5, OR2L8, OR2M2, OR2M5, OR2M7, OR2S2, OR2T10, OR2T2, OR2T27, OR2T29, OR2T3, OR2T33, OR2T34, OR2T35, OR2T4, OR2T5, OR2T8, OR2V1, OR2V2, OR2W1, OR3A1, OR3A2, OR3A3, OR4A15, OR4A47, OR4C12, OR4C13, OR4C46, OR4D1, OR4D10, OR4D11, OR4D2, OR4D9, OR4F16, OR4F21, OR4F29, OR4F3, OR4K15, OR4M1, OR4M2, OR4N2, OR4N4, OR4N5, OR4P4, OR4Q3, OR51A2, OR51A4, OR52E2, OR52E6, OR52E8, OR52H1, OR5211, OR52I2, OR52J3, OR52K1, OR52K2, OR52L1, OR56A1, OR56A3, OR56A4, OR56A5, OR56B4, OR5AK2, OR5B2, OR5B3, OR5D16, OR5F1, OR5H14, OR5H2, OR5H6, OR5J2, OR5L1, OR5L2, OR5M1, OR5M10, OR5M3, OR5M8, OR5P3, OR5T1, OR5T2, OR5T3, OR5V1, OR6B2, OR6B3, OR6C6, OR7A10, OR7A5, OR7C1, OR7C2, OR7G3, OR8A1, OR8B12, OR8B2, OR8B3, OR8B8, OR8G2, OR8G5, OR8H1, OR8H2, OR8H3, OR8J1, OR8J3, OR9A2, OR9A4, OR9G1, ORC3, ORM1, ORM2, OSTC, OSTCP2, OTOA, OTOP1, OTUD4, OTUD7A, OTX2, OVOS, OXCT2, OXR1, OXT, P2RX6, P2RX7, P2RY8, PA2G4, PAAF1, PABPC1, PABPC1L2A, PABPC1L2B, PABPC3, PABPC4, PABPN1, PAEP, PAFAH1B1, PAFAH1B2, PAGE1, PAGE2, PAGE2B, PAGES, PAICS, PAIP1, PAK2, PAM, PANK3, PARG, PARL, PARN, PARP1, PARP4, PARP8, PATL1, PBX1, PBX2, PCBD2, PCBP1, PCBP2, PCDH11X, PCDH11Y, PCDH8, PCDHA1, PCDHA11, PCDHA12, PCDHA13, PCDHA2, PCDHA3, PCDHAS, PCDHA6, PCDHA7, PCDHA8, PCDHA9, PCDHB10, PCDHB11, PCDHB12, PCDHB13, PCDHB15, PCDHB16, PCDHB4, PCDHB8, PCDHGA1, PCDHGA11, PCDHGA12, PCDHGA2, PCDHGA3, PCDHGA4, PCDHGA5, PCDHGA7, PCDHGA8, PCDHGA9, PCDHGB1, PCDHGB2, PCDHGB3, PCDHGB5, PCDHGB7, PCGF6, PCMTD1, PCNA, PCNP, PCNT, PCSK5, PCSK7, PDAP1, PDCD2, PDCD5, PDCD6, PDCD6IP, PDCL2, PDCL3, PDE4DIP, PDIA3, PDLIM1, PDPK1, PDPR, PDSS1, PDXDC1, PDZD11, PDZK1, PEBP1, PEF1, PEPD, PERP, PEX12, PEX2, PF4, PF4V1, PFDN1, PFDN4, PFDN6, PFKFB1, PFN1, PGA3, PGA4, PGA5, PGAM1, PGAM4, PGBD3, PGBD4, PGD, PGGT1B, PGK1, PGK2, PGM5, PHAX, PHB, PHC1, PHF1, PHF10, PHF2, PHFSA, PHKA1, PHLPP2, PHOSPH01, PI3, PI4K2A, PI4KA, PIEZO2, PIGA, PIGF, PIGH, PIGN, PIGY, PIK3CA, PIK3CD, PILRA, PIN1, PIN4, PIP5K1A, PITPNB, PKD1, PKM, PKP2, PKP4, PLA2G10, PLA2G12A, PLA2G4C, PLACE, PLAC9, PLAGL2, PLD5, PLEC, PLEKHA3, PLEKHA8, PLE- KHM1, PLG, PLGLB1, PLGLB2, PLIN2, PLIN4, PLK1, PLLP, PLSCR1, PLSCR2, PLXNA1, PLXNA2, PLXNA3, PLXNA4, PM20D1, PMCH, PMM2, PMPCA, PMS2, PNKD, PNLIP, PNLIPRP2, PNMA6A, PNMA6B, PNMA6C, PNMA6D, PN01, PNPLA4, PNPT1, POLD2, POLE3, POLH, POLR2E, POLR2J, POLR2J2, POLR2J3, POLR2M, POLR3D, POLR3G, POLR3K, POLRMT, POM121, POM121C, POMZP3, PO TEA, POTEC, POTED, PO TEE, POTEF, POTEH, POTEI, POTEJ, POTEM, POU3F1, POU3F2, POU3F3, POU3F4, POU4F2, POU4F3, POU5F1, PPA1, PPAT, PPBP, PPCS, PPEF2, PPFIBP1, PPIA, PPIAL4C, PPIAL4D, PPIAL4E, PPIAL4F, PPIE, PPIG, PPIL1, PPIP5K1, PPIP5K2, PPM1A, PPP1R11, PPP1R12B, PPP1R14B, PPP1R18, PPP1R2, PPP1R26, PPP1R8, PPP2CA, PPP2CB, PPP2R2D, PPP2R3B, PPP2R5C, PPP2R5E, PPP4R2, PPP5C, PPP5D1, PPP6R2, PPP6R3, PPT2, PPY, PRADC1, PRAMEF1, PRAMEF10, PRAMEF11, PRAMEF12, PRAMEF13, PRAMEF14, PRAMEF15, PRAMEF16, PRAMEF17, PRAMEF18, PRAMEF19, PRAMEF20, PRAMEF21, PRAMEF22, PRAMEF23, PRAMEF25, PRAMEF3, PRAMEF4, PRAMEF5, PRAMEF6, PRAMEF7, PRAMEF8, PRAMEF9, PRB1, PRB2, PRB3, PRB4, PRDM7, PRDM9, PRDX1, PRDX2, PRDX3, PRDX6, PRELID1, PRG4, PRH1, PRH2, PRKAR1A, PRKCI, PRKRA, PRKRIR, PRKX, PRMT1, PRMT5, PRODH, PROKR1, PROKR2, PROS 1, PRPF3, PRPF38A, PRPF4B, PRPS1, PRR12, PRR13, PRR20A, PRR20B, PRR20C, PRR20D, PRR20E, PRR21, PRR23A, PRR23B, PRR23C, PRR3, PRR5-ARHGAP8, PRRC2A, PRRC2C, PRRT1, PRSS1, PRSS21, PRSS3, PRSS41, PRSS42, PRSS48, PRUNE, PRY, PRY2, PSAT1, PSG1, PSG11, PSG2, PSG3, PSG4, PSG5, PSG6, PSG8, PSG9, PSIP1, PSMA6, PSMB3, PSMB5, PSMB8, PSMB9, PSMC1, PSMC2, PSMC3, PSMC5, PSMC6, PSMD10, PSMD12, PSMD2, PSMD4, PSMD7, PSMD8, PSME2, PSORS1C1, PSORS1C2, PSPH, PTBP1, PTCD2, PTCH1, PTCHD3, PTCHD4, PTEN, PTGES3, PTGES3L-AARSD1, PTGR1, PTMA, PTMS, PTOV1, PTP4A1, PTP4A2, PTPN11, PTPN2, PTPN20A, PTPN20B, PTPRD, PTPRH, PTPRM, PTPRN2, PTPRU, PTTG1, PTTG2, PVRIG, PVRL2, PWWP2A, PYGB, PYGL, PYHIN1, PYROXD1, PYURF, PYY, PZP, QRSL1, R3HDM2, RAB11A, RAB11FIP1, RAB13, RAB18, RAB1A, RAB1B, RAB28, RAB31, RAB40AL, RAB40B, RAB42, RAB43, RAB5A, RAB5C, RAB6A, RAB6C, RAB9A, RABGEF1, RABGGTB, RABL2A, RABL2B, RABL6, RAC1, RACGAP1, RAD1, RAD17, RAD21, RAD23B, RAD51AP1, RAD54L2, RAET1G, RAET1L, RALA, RALBP1, RALGAPA1, RAN, RANBP1, RANBP17, RANBP2, RANBP6, RAP1A, RAP1B, RAP1GDS1, RAP2A, RAP2B, RARS, RASA4, RASA4B, RASGRP2, RBAK, RBAK-LOC389458, RBBP4, RBBP6, RBM14-RBM4, RBM15, RBM17, RBM39, RBM4, RBM43, RBM48, RBM48, RBM7, RBM8A, RBMS1, RBMS2, RBMX, RBMX2, RBMXL1, RBMXL2, RBMY1A1, RBMY1B, RBMY1D, RBMY1E, RBMY1F, RBMY1J, RBPJ, RCBTB1, RCBTB2, RCC2, RCN1, RCOR2, RDBP, RDH16, RDM1, RDX, RECQL, REG1A, REG1B, REG3A, REG3G, RELA, RERE, RETSAT, REV1, REXO4, RFC3, RFESD, RFK, RFPL1, RFPL2, RFPL3, RFPL4A, RFTN1, RFWD2, RGL2, RGPD1, RGPD2, RGPD3, RGPD4, RGPD5, RGPD6, RGPD8, RGS17, RGS19, RGS9, RHBDF1, RHCE, RHD, RHEB, RHOQ, RHOT1, RHOXF2, RHOXF2B, RHPN2, RIMBP3, RIMBP3B, RIMBP3C, RIMKLB, RING1, RLIM, RLN1, RLN2, RLTPR, RMND1, RMND5A, RNASE2, RNASE3, RNASE7, RNASE8, RNASEH1, RNASET2, RNF11, RNF123, RNF126, RNF13, RNF138, RNF14, RNF141, RNF145, RNF152, RNF181, RNF2, RNF216, RNF39, RNF4, RNF5, RNF6, RNFT1, RNMTL1, RNPC3, RNPS1, ROBO2, ROCK1, ROPN1, ROPN1B, RORA, RP9, RPA2, RPA3, RPAP2, RPE, RPF2, RPGR, RPL10, RPL10A, RPL10L, RPL12, RPL13, RPL14, RPL15, RPL17, RPL17-C180RF32, RPL18A, RPL19, RPL21, RPL22, RPL23, RPL23A, RPL24, RPL26, RPL26L1, RPL27, RPL27A, RPL29, RPL3, RPL30, RPL31, RPL32, RPL35, RPL35A, RPL36, RPL36A, RPL36A-HNRNPH2, RPL36AL, RPL37, RPL37A, RPL39, RPL4, RPL41, RPL5, RPL6, RPL7, RPL7A, RPL7L1, RPL8, RPL9, RPLP0, RPLP1, RPP21, RPS10, RPS10-NUDT3, RPS11, RPS13, RPS14, RPS15, RPS15A, RPS16, RPS17, RPS17L, RPS18, RPS19, RPS2, RPS20, RPS23, RPS24, RPS25, RPS26, RPS27, RPS27A, RPS28, RPS3, RPS3A, RPS4X, RPS4Y1, RPS4Y2, RPS5, RPS6, RPS6KB1, RPS7, RPS8, RPS9, RPSA, RPTN, RRAGA, RRAGB, RRAS2, RRM2, RRN3, RRP7A, RSL24D1, RSPH10B, RSPH10B2, RSPO2, RSRC1, RSU1, RTEL1, RTN3, RTN4IP1, RTN4R, RTP1, RTP2, RUFY3, RUNDC1, RUVBL2, RWDD1, RWDD4, RXRB, RYK, S100A11, S100A7L2, SAA1, SAA2, SAA2-SAA4, SAE1, SAFB, SAFB2, SAGE1, SALL1, SALL4, SAMD1, SAMD9, SAMD9L, SAP18, SAP25, SAP30, SAPCD1, SAPCD2, SAR1A, SATL1, SAV1, SAYSD1, SBDS, SBF1, SCAMPI, SCAND3, SCD, SCGB1D1, SCGB1D2, SCGB1D4, SCGB2A1, SCGB2A2, SCGB2B2, SCN10A, SCN1A, SCN2A, SCN3A, SCN4A, SCN5A, SCN9A, SCOC, SCXA, SCXB, SCYL2, SDAD1, SDCBP, SDCCAG3, SDHA, SDHB, SDHC, SDHD, SDR42E1, SEC11A, SEC14L1, SEC14L4, SEC14L6, SEC61B, SEC63, SELT, SEMA3E, SEMG1, SEMG2, SEPHS1, SEPHS2, SEPT14, SEPT7, SERBP1, SERF1A, SERF1B, SERF2, SERHL2, SERPINB3, SERPINB4, SERPINH1, SET, SETD8, SF3A2, SF3A3, SF3B14, SF3B4, SFR 1, SFRP4, SFTA2, SFTPA1, SFTPA2, SH2D1B, SH3BGRL3, SH3GL1, SHANK2, SHC1, SHCBP1, SHFM1, SHH, SHISA5, SHMT1, SHOX, SHQ 1, SHROOM2, SIGLEC10, SIGLEC11, SIGLEC12, SIGLEC14, SIGLEC5, SIGLEC6, SIGLEC7, SIGLEC8, SIGLEC9, SIMC1, SIN3A, SIRPA, SIRPB1, SIRPG, SIX1, SIX2, SKA2, SKIV2L, SKOR2, SKP1, SKP2, SLAIN2, SLAMF6, SLC10A5, SLC16A14, SLC16A6, SLC19A3, SLC22A10, SLC22A11, SLC22A12, SLC22A24, SLC22A25, SLC22A3, SLC22A4, SLC22A5, SLC22A9, SLC25A13, SLC25A14, SLC25A15, SLC25A20, SLC25A29, SLC25A3, SLC25A33, SLC25A38, SLC25A47, SLC25A5, SLC25A52, SLC25A53, SLC25A6, SLC29A4, SLC2A13, SLC2A14, SLC2A3, SLC31A1, SLC33A1, SLC35A4, SLC35E1, SLC35E2, SLC35E2B, SLC35G3, SLC35G4, SLC35G5, SLC35G6, SLC36A1, SLC36A2, SLC39A1, SLC39A7, SLC44A4, SLC4A1AP, SLC52A1, SLC52A2, SLC5A6, SLC5A8, SLC6A14, SLC6A6, SLC6A8, SLC7A5, SLC8A2, SLC8A3, SLC9A2, SLC9A4, SLC9A7, SLCO1B1, SLCO1B3, SLCO1B7, SLFN11, SLFN12, SLFN12L, SLFN13, SLFN5, SLIRP, SLMO2, SLX1A, SLX1B, SMARCE1, SMC3, SMC5, SMEK2, SMG1, SMN1, SMN2, SMR3A, SMR3B, SMS, SMU1, SMURF2, SNAI1, SNAPC4, SNAPC5, SNF8, SNRNP200, SNRPA1, SNRPB2, SNRPC, SNRPD1, SNRPD2, SNRPE, SNRPG, SNRPN, SNW1, SNX19, SNX25, SNX29, SNX5, SNX6, SOCS5, SOCS6, SOGA1, SOGA2, SON, SOX1, SOX10, SOX14, SOX2, SOX30, SOX5, SOX9, SP100, SP140, SP140L, SP3, SPS, SP8, SP9, SPACA5, SPACA5B, SPACA7, SPAG11A, SPAG11B, SPANXA1, SPANX81, SPANXD, SPANXN2, SPANXN5, SPATA16, SPATA20, SPATA31A1, SPATA31A2, SPA TA31A3, SPATA31A4, SPA TA31A5, SPATA31A6, SPA TA31A7, SPATA31C1, SPATA31C2, SPATA31D1, SPATA31D3, SPATA31D4, SPATA31E1, SPCS2, SPDYE1, SPDYE2, SPDYE2L, SPDYE3, SPDYE4, SPDYE5, SPDYE6, SPECC1, SPECC1L, SPHAR, SPIC, SPIN1, SPIN2A, SPIN2B, SPOPL, SPPL2A, SPPL2C, SPR, SPRR1A, SPRR1B, SPRR2A, SPRR2B, SPRR2D, SPRR2E, SPRR2F, SPRY3, SPRYD4, SPTLC1, SRD5A1, SRD5A3, SREK1IP1, SRGAP2, SRP14, SRP19, SRP68, SRP72, SRP9, SRPK1, SRPK2, SRRM1, SRSF1, SRSF10, SRSF11, SRSF3, SRSF6, SRSF9, SRXN1, SS18L2, SSB, SSBP2, SSBP3, SSBP4, SSNA1, SSR3, SSX1, SSX2, SSX2B, SSX3, SSX4, SSX4B, SSX5, SSX7, ST13, ST3GAL1, STAG3, STAR, STAT5A, STAT5B, STAU1, STAU2, STBD1, STEAP1, STEAP1B, STH, STIP1, STK19, STK24, STK32A, STMN1, STMN2, STMN3, STRADB, STRAP, STRC, STRN, STS, STUB1, STX18, SUB1, SUCLA2, SUCLG2, SUDS3, SUGP1, SUGT1, SULT1A1, SULT1A2, SULT1A3, SULT1A4, SUMF2, SUMO1, SUMO2, SUPT16H, SUPT4H1, SUSD2, SUZ12, SVIL, SWI5, SYCE2, SYNCRIP, SYNGAP1, SYNGR2, SYT14, SYT15, SYT2, SYT3, SZRD1, TAAR6, TAAR8, TACC1, TADA1, TAF1, TAF15, TAF1L, TAF4B, TAF5L, TAF9, TAF9B, TAGLN2, TALDO1, TANC2, TAP1, TAP2, TAPBP, TARBP2, TARDBP, TARP, TAS2R19, TAS2R20, TAS2R30, TAS2R39, TAS2R40, TAS2R43, TAS2R46, TAS2R50, TASP1, TATDN1, TATDN2, TBC1D26, TBC1D27, TBC1D28, TBC1D29, TBC1D2B, TBC1D3, TBC1D3B, TBC1D3C, TBC1D3F, TBC1D3G, TBC1D3H, TBCA, TBCCD1, TBL1X, TBL1XR1, TBL1Y, TBPL1, TBX20, TC2N, TCEA1, TCEAL2, TCEAL3, TCEAL5, TCEB1, TCEB2, TCEB3B, TCEB3C, TCEB3CL, TCEB3CL2, TCERG1L, TCF19, TCF3, TCHH, TCL1B, TCOF1, TCP1, TCP10, TCP10L, TCP10L2, TDG, TDGF1, TDRD1, TEAD1, TEC, TECR, TEKT4, TERF1, TERF2IP, TET1, TEX13A, TEX13B, TEX28, TF, TFB2M, TFDP3, TFG, TGIF1, TGIF2, TGIF2LX, TGIF2LY, THAP3, THAP5, THEM4, THOC3, THRAP3, THSD1, THUMPD1, TIMM17B, TIMM23B, TIMM8A, TIMM8B, TIMP4, TIPIN, TJAP1, TJP3, TLE1, TLE4, TLK1, TLK2, TLL1, TLR1, TLR6, TMA16, TMA7, TMC6, TMCC1, TMED10, TMED2, TMEM126A, TMEM128, TMEM132B, TMEM132C, TMEM14B, TMEM14C, TMEM161B, TMEM167A, TMEM183A, TMEM183B, TMEM185A, TMEM185B, TMEM189-UBE2V1, TMEM191B, TMEM191C, TMEM230, TMEM231, TMEM236, TMEM242, TMEM251, TMEM254, TMEM30B, TMEM47, TMEM69, TMEM80, TMEM92, TMEM97, TMEM98, TMLHE, TMPRSS11E, TMSB10, TMSB15A, TMSB15B, TMSB4X, TMSB4Y, TMTC1, TMTC4, TMX1, TMX2, TNC, TNF, TNFRSF10A, TNFRSF10B, TNFRSF10C, TNFRSF10D, TNFRSF13B, TNFRSF14, TNIP2, TNN, TNPO1, TNRC18, TNXB, TOB2, TOE1, TOMM20, TOMM40, TOMM6, TOMM7, TOP1, TOP3B, TOR1B, TOR3A, TOX4, TP53TG3, TP53TG3B, TP53TG3C, TPD52L2, TPI1, TPM3, TPM4, TPMT, TPRKB, TPRX1, TPSAB1, TPSB2, TPSD1, TPT1, TPTE, TPTE2, TRA2A, TRAF6, TRAPPC2, TRAPPC2L, TREH, TREML2, TREML4, TRIM10, TRIM15, TRIM16, TRIM16L, TRIM26, TRIM27, TRIM31, TRIM38, TRIM39, TRIM39-RPP21, TRIM40, TRIM43, TRIM43B, TRIM48, TRIM49, TRIM49B, TRIM49C, TRIM49DP, TRIM49L1, TRIM50, TRIM51, TRIM51GP, TRIM60, TRIM61, TRIM64, TRIM64B, TRIM64C, TRIM73, TRIM74, TRIM77P, TRIP11, TRMT1, TRMT11, TRMT112, TRMT2B, TRNT1, TRO, TRPA1, TRPC6, TRPV5, TRPV6, TSC22D3, TSEN15, TSEN2, TSPAN11, TSPY1, TSPY10, TSPY2, TSPY3, TSPY4, TSPY8, TSPYL1, TSPYL6, TSR 1, TSSK1B, TSSK2, TTC28, TTC3, TTC30A, TTC30B, TTC4, TTL, TTLL12, TTLL2, TTN, TUBA1A, TUBA1B, TUBA1C, TUBA3C, TUBA3D, TUBA3E, TUBA4A, TUBAE, TUBB, TUBB2A, TUBB2B, TUBB3, TUBB4A, TUBB4B, TUBB6, TUBB8, TUBE1, TUBG1, TUBG2, TUBGCP3, TUBGCP6, TUFM, TWF1, TWIST2, TXLNG, TXN2, TXNDC2, TXNDC9, TYR, TYRO3, TYW1, TYW1B, U2AF1, UAP1, UBA2, UBA5, UBD, UBE2C, UBE2D2, UBE2D3, UBE2D4, UBE2E3, UBE2F, UBE2H, UBE2L3, UBE2M, UBE2N, UBE2Q2, UBE2S, UBE2V1, UBE2V2, UBE2W, UBE3A, UBFD1, UBQLN1, UBQLN4, UBTFL1, UBXN2B, UFD1L, UFM1, UGT1A10, UGT1A3, UGT1A4, UGT1A5, UGT1A7, UGT1A8, UGT1A9, UGT2A1, UGT2A2, UGT2A3, UGT2B10, UGT2B11, UGT2B15, UGT2B17, UGT2B28, UGT2B4, UGT2B7, UGT3A2, UHRF1, UHRF2, ULBP1, ULBP2, ULBP3, ULK4, UNC93A, UNC93B1, UPF3A, UPK3B, UPK3BL, UQCR10, UQCRB, UQCRFS1, UQCRH, UQCRQ, USP10, USP12, USP13, USP17L10, USP17L11, USP17L12, USP17L13, USP17L15, USP17L17, USP17L18, USP17L19, USP17L1P, USP17L2, USP17L20, USP17L21, USP17L22, USP17L24, USP17L25, USP17L26, USP17L27, USP17L28, USP17L29, USP17L3, USP17L30, USP17L4, USP17L5, USP17L7, USP17L8, USP18, USP22, USP32, USP34, USP6, USPS, USP9X, USP9Y, UTP14A, UTP14C, UTP18, UTP6, VAMPS, VAMP7, VAPA, VARS, VARS2, VCX, VCX2, VCX3A, VCX3B, VCY, VCY1B, VDAC1, VDAC2, VDAC3, VENTX, VEZF1, VKORC1, VKORC1L1, VMA21, VN1R4, VNN1, VOPP1, VPS26A, VPS35, VPS37A, VPS51, VPS52, VSIG10, VTCN1, VTI1B, VWA5B2, VWA7, VWA8, VWF, WARS, WASF2, WASF3, WASH1, WBP1, WBP11, WBP1L, WBSCR16, WDR12, WDR45, WDR45L, WDR46, WDR49, WDR59, WDR70, WDR82, WDR89, WFDC10A, WFDC10B, WHAMM, WHSC1L1, WIPI2, WIZ, WNT3, WNT3A, WNT5A, WNT5B, WNT9B, WRN, WTAP, WWC2, WWC3, WWP1, XAGE1A, XAGE1B, XAGE1C, XAGE1D, XAGE1E, XAGE2, XAGE3, XAGE5, XBP1, XCL1, XCL2, XG, XIAP, XKR3, XKR8, XKRY, XKRY2, XPO6, XPOT, XRCC6, YAP1, YBX1, YBX2, YES1, YME1L1, YPEL5, YTHDC1, YTHDF1, YTHDF2, YWHAB, YWHAE, YWHAQ, YWHAZ, YY1, YY1AP1, ZAN, ZBED1, ZBTB10, ZBTB12, ZBTB22, ZBTB44, ZBTB45, ZBTB8OS, ZBTB9, ZC3H11A, ZC3H12A, ZCCHC10, ZCCHC12, ZCCHC17, ZCCHC18, ZCCHC2, ZCCHC7, ZCCHC9, ZCRB1, ZDHHC11, ZDHHC20, ZDHHC3, ZDHHC8, ZEB2, ZFAND5, ZFAND6, ZFP106, ZFP112, ZFP14, ZFP57, ZFP64, ZFP82, ZFR, ZFX, ZFY, ZFYVE1, ZFYVE9, ZIC1, ZIC2, ZIC3, ZIC4, ZIK1, ZKSCAN3, ZKSCAN4, ZMIZ1, ZMIZ2, ZMYM2, ZMYM5, ZNF100, ZNF101, ZNF107, ZNF114, ZNF117, ZNF12, ZNF124, ZNF131, ZNF135, ZNF14, ZNF140, ZNF141, ZNF146, ZNF155, ZNF160, ZNF167, ZNF17, ZNF181, ZNF185, ZNF20, ZNF207, ZNF208, ZNF212, ZNF221, ZNF222, ZNF223, ZNF224, ZNF225, ZNF226, ZNF229, ZNF230, ZNF233, ZNF234, ZNF235, ZNF248, ZNF253, ZNF254, ZNF257, ZNF259, ZNF26, ZNF264, ZNF266, ZNF267, ZNF280A, ZNF280B, ZNF282, ZNF283, ZNF284, ZNF285, ZNF286A, ZNF286B, ZNF300, ZNF302, ZNF311, ZNF317, ZNF320, ZNF322, ZNF323, ZNF324, ZNF324B, ZNF33A, ZNF33B, ZNF341, ZNF347, ZNF35, ZNF350, ZNF354A, ZNF354B, ZNF354C, ZNF366, ZNF37A, ZNF383, ZNF396, ZNF41, ZNF415, ZNF416, ZNF417, ZNF418, ZNF419, ZNF426, ZNF429, ZNF43, ZNF430, ZNF431, ZNF433, ZNF439, ZNF44, ZNF440, ZNF441, ZNF442, ZNF443, ZNF444, ZNF451, ZNF460, ZNF468, ZNF470, ZNF479, ZNF480, ZNF484, ZNF486, ZNF491, ZNF492, ZNF506, ZNF528, ZNF532, ZNF534, ZNF543, ZNF546, ZNF547, ZNF548, ZNF552, ZNF555, ZNF557, ZNF558, ZNF561, ZNF562, ZNF563, ZNF564, ZNF57, ZNF570, ZNF578, ZNF583, ZNF585A, ZNF585B, ZNF586, ZNF587, ZNF587B, ZNF589, ZNF592, ZNF594, ZNF595, ZNF598, ZNF605, ZNF607, ZNF610, ZNF613, ZNF614, ZNF615, ZNF616, ZNF620, ZNF621, ZNF622, ZNF625, ZNF626, ZNF627, ZNF628, ZNF646, ZNF649, ZNF652, ZNF655, ZNF658, ZNF665, ZNF673, ZNF674, ZNF675, ZNF676, ZNF678, ZNF679, ZNF680, ZNF681, ZNF682, ZNF69, ZNF700, ZNF701, ZNF705A, ZNF705B, ZNF705D, ZNF705E, ZNF705G, ZNF706, ZNF708, ZNF709, ZNF710, ZNF714, ZNF716, ZNF717, ZNF718, ZNF720, ZNF721, ZNF726, ZNF727, ZNF728, ZNF729, ZNF732, ZNF735, ZNF736, ZNF737, ZNF746, ZNF747, ZNF749, ZNF75A, ZNF75D, ZNF761, ZNF763, ZNF764, ZNF765, ZNF766, ZNF770, ZNF773, ZNF775, ZNF776, ZNF777, ZNF780A, ZNF780B, ZNF782, ZNF783, ZNF791, ZNF792, ZNF799, ZNF805, ZNF806, ZNF808, ZNF812, ZNF813, ZNF814, ZNF816, ZNF816-ZNF321P, ZNF823, ZNF829, ZNF83, ZNF836, ZNF84, ZNF841, ZNF844, ZNF845, ZNF850, ZNF852, ZNF878, ZNF879, ZNF880, ZNF90, ZNF91, ZNF92, ZNF93, ZNF98, ZNF99, ZNRD1, ZNRF2, ZP3, ZRSR2, ZSCAN5A, ZSCAN5B, ZSCAN5D, ZSWIM5, ZXDA, ZXDB, and ZXDC.

E1. A computer-implemented method for determining a likelihood of a presence or absence of a genetic variation in a gene of interest having at least one counterpart gene, the method comprising:

(a) mapping sequence reads to a modified reference genome, wherein 1) the modified reference genome comprises a nucleic acid sequence of the gene of interest and a nucleic acid sequence of the at least one counterpart gene, wherein the nucleic acid sequence of the at least one counterpart gene in the modified reference genome is substantially altered, 2) the sequence reads comprise reads obtained from one or more subjects using a massively parallel sequencing method, and 3) sequence reads derived from the at least one counterpart gene map to the nucleic acid sequence of the gene of interest of the modified reference genome, thereby providing mapped reads; and (b) determining the likelihood of the presence or absence of the genetic variation in the gene of interest of the one or more subjects according to the mapped reads.

E1.2. The method of embodiment E1, wherein at least 30% of the nucleotides of the nucleic acid sequence of the at least one counterpart gene in the modified reference genome are substituted with ambiguous nucleotide markers.

E2. The method of embodiment E1 or E1.2, wherein the one or more subjects are diploid.

E2.1. The method of any one of embodiments E1 to E2, wherein the mapping is performed by a mapping module.

E2.2. The method of E2.1, comprising instructing the mapping module to expect a ploidy of at least 4.

E3. The method of embodiment E2.2, wherein the ploidy is 4 and the gene of interest has 1 counterpart gene.

E3.1. The method of embodiment E2.2, wherein the ploidy is 6 and the gene of interest has 2 counterpart genes.

E3.2. The method of embodiment E2.2, wherein the ploidy is equal to the sum of (i) two times the number of the at least one counterpart gene and (ii) 2.

E4. The method of any one of embodiments E1 to E3.2, wherein the at least one counterpart gene of the one or more subjects is at least one pseudogene of the gene of interest.

E5. The method of any one of embodiments E1 to E4, wherein one or more nucleotides of the nucleic acid sequence of the at least one counterpart gene of the modified reference genome are deleted.

E6. The method of any one of embodiments E1 to E8, wherein the gene of interest of the subject is selected from PMS2, NEB, HBA1, HBG1, HBB, SBSD, VWF, CYP2D6, CYP21A2, PKD1 and PRSS1.

E7. The method of any one of embodiments E1 to E6, further comprising confirming the presence or absence of the genetic variation.

E8. The method of embodiment E7, wherein the presence or absence of the genetic variation is confirmed by a method comprising re-sequencing the gene of interest.

E9. The method of any one of embodiments E1 to E8, wherein the one or more subjects comprises at least 100 subjects.

E10. The method of any one of embodiments E1 to E8, wherein the one or more subjects comprises at least 1000 subjects.

E11. The method of embodiment E9 or E10, wherein the determining the likelihood of the presence or absence of the genetic variation comprises determining the likelihood of the presence of a genetic variation in a subet of the one or more subjects.

E12. The method of embodiment E11, wherein the presence of the genetic variation in one or more subjects of the subet is confirmed by a process comprising sequencing the gene of interest in the one or more subjects.

E13. The method of embodiment E11, wherein the presence of the genetic variation in one or more subjects of the subet is confirmed by a process comprising sequencing the gene of interest in the one or more subjects.

E14. The method of any one of embodiments E1 to E13, wherein the genetic variation is a single nucleotide polymorphism.

E15. The method of any one of embodiments E1 to E15, wherein the sequence reads are provided in the form of a non-transitory computer readable medium.

The examples set forth above illustrate certain embodiments and do not limit the technology.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A computer-implemented method for determining a likelihood of a presence or absence of a genetic variation in a gene of interest for a subject where the subject's genome also contains at least one counterpart gene to the gene of interest such that the at least one counterpart gene is at least 80% identical to the gene of interest, comprising the steps of:
   (a) providing a modified reference genome comprising (i) the gene of interest and (ii) one or more counterpart genes to the gene of interest that are substantially altered, wherein at least 30% of nucleotides of the one or more counterpart genes of the modified reference genome are substituted with different nucleotides such that sequence reads obtained from the gene of interest of the subject or the at least one counterpart gene of the subject map to the gene of interest of the modified reference genome instead of to the one or more counterpart genes of the reference genome;
   (b) mapping sequence reads obtained from the subject to the modified reference genome, wherein (i) the sequence reads are obtained from a sample obtained from a diploid subject using a massively parallel sequencing method, and (ii) the sequence reads obtained from the gene of interest and the at least one counterpart gene of the subject map to the gene of interest of the modified reference genome and not to the one or more counterpart genes of the modified reference genome, thereby providing sequence reads mapped to the gene of interest of the modified reference genome; and
   (c) determining the likelihood of a presence or absence of a genetic variation in the gene of interest of the subject according to the sequence reads mapped to the gene of interest of the modified reference genome.

2. The method of claim 1, wherein the mapping comprises an expectation that at least 4 alleles of the gene of interest of the subject map to the gene of interest of the modified reference genome.

3. The method of claim 1, wherein a ploidy of at least 4 is expected for the gene of interest of the subject.

4. The method of claim 1, wherein the at least one counterpart gene of the subject is at least 90% identical to the gene of interest of the subject.

5. The method of claim 1, wherein the at least one counterpart gene of the subject is at least 95% identical to the gene of interest of the subject.

6. The method of claim 1, wherein the at least one counterpart gene of the subject is a pseudogene of the gene of interest of the subject.

7. The method of claim 1, wherein the at least one counterpart gene of the subject is 1 to 5 counterpart genes.

8. The method of claim 7, wherein the at least one counterpart gene of the subject is 1 counterpart gene.

9. The method of claim 7, wherein the at least one counterpart gene of the subject is 2 to 5 counterpart genes.

10. The method of claim 1, wherein each of the at least one counterpart genes of the subject comprise two alleles.

11. The method of claim 1, wherein the gene of interest of the subject comprises two alleles.

12. The method of claim 1, wherein at least 50% of nucleotides of the one or more counterpart genes of the modified reference genome are substituted with different nucleotides.

13. The method of claim 1, wherein the nucleotides of the one or more counterpart genes of the modified reference genome are substituted with ambiguous nucleotide markers.

14. The method of claim 13, wherein the ambiguous nucleotide markers comprise an N.

15. The method of claim 1, wherein one or more nucleotides of the one or more counterpart genes of the modified reference genome are deleted.

16. The method of claim 1, wherein one or more nucleotides are inserted into the one or more counterpart genes of the modified reference genome.

17. The method of claim 1, wherein the sequence reads are obtained for an entire genome.

18. The method of claim 1, wherein the sequence reads are obtained by a chromosome-specific method or a gene-specific method.

19. The method of claim 1, wherein the sequence reads are obtained by a method comprising paired-end sequencing.

20. The method of claim 1, wherein the sequence reads are 100-200 bp in length.

21. The method of claim 1, wherein the sequence reads represent at least 20-fold coverage of the gene of interest of the subject.

22. The method of claim 1, wherein the sequence reads represent at least 50-fold coverage of the gene of interest of the subject.

23. The method of claim 1, wherein the gene of interest of the subject is selected from PMS2, HBA1, HBG1, HBB, SBSD, and VWF.

24. The method of claim 23, wherein the gene of interest of the subject is PMS2 and the at least one counterpart gene of the subject is PMS2CL.

25. The method of claim 23, wherein the gene of interest of the subject is HBA1 and the at least one counterpart gene of the subject is HBA2.

26. The method of claim 23, wherein the gene of interest of the subject is HBG1 and the at least one counterpart gene of the subject is HBG2.

27. The method of claim 23, wherein the gene of interest of the subject is HBB and the at least one counterpart gene of the subject is HBD.

28. The method of claim 23, wherein the gene of interest of the subject is SBDS and the at least one counterpart gene of the subject is SBDSP1.

29. The method of claim 1, wherein the gene of interest of the subject is selected from CYP2D6, CYP21A2, PKD1 and PRSS1.

30. The method of claim 1, where the determining of (c) comprises determining the presence or absence of the genetic variation in the gene of interest of the subject.

31. The method of claim 30, wherein the presence or absence of the genetic variation is determined by a method comprising LR-PCR and re-sequencing.

32. The method of claim 1, wherein the absence of the genetic variation in both the gene of interest of the subject and the at least one counterpart gene of the subject is determined in (c).

33. The method of claim 1, wherein the likelihood of the presence of the genetic variation in either or both of the gene of interest of the subject and the at least one counterpart gene of the subject is determined in (c).

34. The method of claim 1, wherein a presence of the genetic variation in the gene of interest of the subject or the at least one counterpart gene of the subject is determined after (c).

35. The method of claim 34, wherein the presence of the genetic variation in the gene of interest of the subject is determined after (c) by sequencing the gene of interest of the subject.

\* \* \* \* \*